(12) United States Patent
Teng et al.

(10) Patent No.: US 10,414,735 B2
(45) Date of Patent: Sep. 17, 2019

(54) SUBSTITUTED HYDROXYPYRIMIDINONES FOR TREATING BACTERIAL INFECTIONS

(71) Applicant: FORGE THERAPEUTICS, INC., San Diego, CA (US)

(72) Inventors: Min Teng, San Diego, CA (US); Baskar Nammalwar, San Diego, CA (US); Konstantin Taganov, San Diego, CA (US); David T. Puerta, San Diego, CA (US)

(73) Assignee: FORGE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/773,975

(22) PCT Filed: Nov. 9, 2016

(86) PCT No.: PCT/US2016/061195
§ 371 (c)(1),
(2) Date: May 4, 2018

(87) PCT Pub. No.: WO2017/083431
PCT Pub. Date: May 18, 2017

(65) Prior Publication Data
US 2018/0327365 A1    Nov. 15, 2018

Related U.S. Application Data

(60) Provisional application No. 62/252,795, filed on Nov. 9, 2015.

(51) Int. Cl.
*A61K 31/505* (2006.01)
*C07D 239/54* (2006.01)
*C07D 239/545* (2006.01)
*C07D 403/12* (2006.01)
*C07D 401/12* (2006.01)
*C07D 213/69* (2006.01)
*A61P 31/04* (2006.01)
*C07D 413/10* (2006.01)
*C07D 413/12* (2006.01)

(52) U.S. Cl.
CPC .......... *C07D 239/545* (2013.01); *A61P 31/04* (2018.01); *C07D 213/69* (2013.01); *C07D 239/54* (2013.01); *C07D 401/12* (2013.01); *C07D 403/12* (2013.01); *C07D 413/10* (2013.01); *C07D 413/12* (2013.01)

(58) Field of Classification Search
CPC .......................... A61K 31/505; C07D 239/54
USPC .......................................... 514/269; 544/319
See application file for complete search history.

(56) References Cited

U.S. PATENT DOCUMENTS

| | | |
|---|---|---|
| 2003/0181472 A1 | 9/2003 | Clark et al. |
| 2007/0149556 A1 | 6/2007 | Mikamiyama et al. |
| 2012/0041032 A1 | 2/2012 | Puerta et al. |
| 2012/0329741 A1 | 12/2012 | Oyelere et al. |
| 2014/0038990 A1 | 2/2014 | Buschmann et al. |
| 2014/0079666 A1 | 3/2014 | Webb et al. |
| 2015/0202208 A1 | 7/2015 | Kiyama et al. |
| 2017/0088532 A1 | 3/2017 | Cohen et al. |
| 2018/0319761 A1 | 11/2018 | Teng et al. |

FOREIGN PATENT DOCUMENTS

| | | |
|---|---|---|
| WO | WO-2006028523 A2 | 3/2006 |
| WO | WO-2008027466 A1 | 3/2008 |
| WO | WO-2008045668 A1 | 4/2008 |
| WO | WO-2008154642 A2 | 12/2008 |
| WO | WO-2010059838 A2 | 5/2010 |
| WO | WO-2014160649 A1 | 10/2014 |
| WO | WO-2015085238 A1 | 6/2015 |
| WO | WO-2015099107 A1 | 7/2015 |
| WO | WO-2017083431 A2 | 5/2017 |
| WO | WO-2017083434 A1 | 5/2017 |
| WO | WO-2018208985 A2 | 11/2018 |
| WO | WO-2018208987 A2 | 11/2018 |

OTHER PUBLICATIONS

Ding et al. Design, synthesis and biological evaluation of LpxC inhibitors with novel hydrophilic terminus. Chinese Chemical Letters 26(6):763-767 (2015).
PCT/US2016/061195 International Search Report and Written Opinion dated Jul. 31, 2017.
PCT/US2016/061198 International Search Report and Written Opinion dated Feb. 15, 2017.
Ravin. Chapter 76: Preformulation. Remington's Pharmaceutical Sciences, 17th ed., Mack Publishing Company, Easton, Pa. (pp. 1409-1423) (1985).

(Continued)

*Primary Examiner* — Douglas M Willis
(74) *Attorney, Agent, or Firm* — Wilson Sonsini Goodrich & Rosati

(57) ABSTRACT

The present teachings relate to hydroxypyrimidinone derivatives of Formula IV, pharmaceutical compositions thereof, and methods of using such compounds to treat bacterial infections.

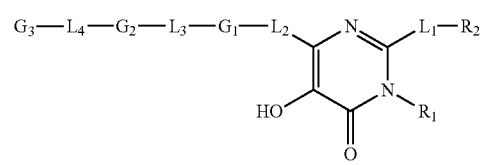

Formula IV

19 Claims, 15 Drawing Sheets

(56) References Cited

OTHER PUBLICATIONS

Yan et al. Synthesis of hydroxypyrone- and hydroxythiopyrone-based matrix metalloproteinase inhibitors: Developing a structure-activity relationship. Bioorg. Med. Chem. Lett. 19(7):1970-1976 (2009).
Bingi et al. One-pot catalyst free synthesis of novel kojic acid tagged 2-aryl/alkyl substituted-4H-chromenes and evaluation of their antimicrobial and anti-biofilm activities. Bioorganic & Medicinal Chemistry Letters25(9):1915-1919 (2015).
PCT/US2015/061198 Preliminary Report on Patentability dated May 24, 2018.
PCT/US2016/061195 International Preliminary Report on Patentability dated May 24, 2018.
PCT/US2018/031896 International Search Report and Written Opinion dated Nov. 7, 2018.
PCT/US2018/031898 International Search Report and Written Opinion dated Nov. 7, 2018.
Aytemir et al. Synthesis and Evaluation of Anticonvulsant and Antimicrobial Activities of 3-Hydroxy-6-methyl-2-substituted 4H-Pyran-4-one Derivatives. Archiv Der Pharmazie 337(5):281-288 (2004).
Emami et al. Mannich bases of 7-piperazinylquinolones and kojic acid derivatives: Synthesis, in vitroantibacterial activity and in silicostudy. EP J Med Chem 68:185-191 (2010).
US et al. 4H-Pyran-4-one derivatives:; leading molecule for preparation of compounds with antimycobacterial potential. Turkish Journal of Chemistry 30:803-812 (2009).
US et al. Mannich base derivatives of 3-hydroxy-6- methyl-4H-pyran-4-one with antimicrobial activity. Turkish Journal of Chemistry 33:447-456 (2010).

SUBSTITUTED HYDROXYPYRIMIDINONES FOR TREATING BACTERIAL INFECTIONS

CROSS-REFERENCE TO RELATED APPLICATIONS

This application is filed pursuant to 35 U.S.C. § 371 as a United States National Phase Application of International Application No. PCT/US2016/061195, filed Nov. 9, 2016; which claims the benefit of U.S. Provisional Patent Application No. 62/252,795, filed Nov. 9, 2015, all of which are incorporated herein by reference in their entirety.

BACKGROUND OF THE INVENTION

Metalloproteins influence a vast diversity of biological systems, biological processes, and diseases. For example, UDP-{3-O-[(R)-3-hydroxymyristoyl]}-N-acetylglucosamine deacetylase (LpxC) is an essential enzyme involved in the first committed step in lipid A biosynthesis for gram-negative bacteria. Lipid A is an essential component of the outer membrane of Gram-negative bacteria. LpxC is a zinc(II)-dependent metalloenzyme, with two histidines and an aspartic acid residue bound to the zinc(II) ion. Structures of LpxC show the zinc(II) ion is bound to two water molecules, both of which have been implicated in the mechanism of the enzyme. LpxC is highly conserved across strains of Gram-negative bacteria. This makes LpxC an attractive target to treat Gram-negative infections.

Many LpxC inhibitors developed to date have issues including lack of cell permeability, off-target toxicity, and efflux.

In recent years, there has been an increase in resistant and multi-drug resistant strains of bacteria. Thus, there is a need for new antibiotics, especially with new mechanisms of action. There remains a need for metalloprotein modulators of LpxC useful in the field of therapeutics, diagnostics, and research.

SUMMARY OF THE INVENTION

Some embodiments provided herein describe compounds and compositions useful for treating bacterial infections.

In one aspect, provided herein are compounds having the structure of Formula II:

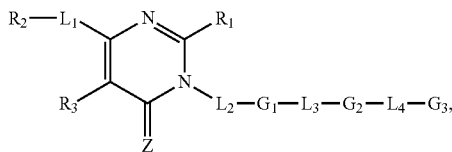

or a pharmaceutically acceptable salt thereof,
wherein:
$R_1$ is H, $C_{1-6}$ alkyl, or $C_{1-6}$ alkoxy;
$R_2$ is H, —$OR^a$, —$N(R^a)_2$, $C_{1-6}$ alkyl, or $C_{1-6}$ alkoxy;
$R_3$ is —OH, —$NH_2$, or SH;
Z is O or S;
$L_1$ is a bivalent radical selected from a bond, —C(=O)—, —C(=O)O—, —C(=O)$NR^b$—, —$N(R^b)$C(=O)—, —($C_{1-4}$ alkylene)-O—, —($C_{1-4}$ alkylene)-N($R^b$)—, —($C_{1-4}$ alkylene)-S—, or —($C_{1-4}$ alkylene)-S(=O)$_2$—;

$L_2$ is a bivalent radical selected from —$(C(R_4)(R_5))_n$—$(C_{0-3}$ alkylene)-, —$(C(R_4)(R_5))_n$—$C_{0-3}$ alkylene)-(C—$OR^c$)—, —$(C(R_4)(R_5))_n$—$(C_{0-3}$ alkylene)-C(=O)—, —$(C(R_4)(R_5))_n$—$(C_{0-3}$ alkylene)-C(=N—OH)—, —$(C(R_4)(R_5))_n$—$(C_{0-3}$ alkylene)-(C(=O)$NR_5$)—, —$(C(R_4)(R_5))_n$—$(C_{0-3}$ alkylene)-$N(R_5)C$(=O)—, —$(C(R_4)(R_5))_n$—$(C_{0-3}$ alkylene)-O—, —$(C(R_4)(R_5))_n$—$(C_{0-3}$ alkylene)-$N(R_5)$—, —$(C(R_4)(R_5))_n$—$(C_{0-3}$ alkylene)-S(=O)$_2$—, —$(C(R_4)(R_5))_n$—$(C_{0-3}$ alkylene)-S(=O)$_2N(R_5)$—, or —$(C(R_4)(R_5))_n$—$(C_{0-3}$ alkylene)-$N(R_5)S$(=O)$_2$—;
wherein each $R_4$ is H or optionally substituted $C_{1-6}$ alkyl; and
each $R_5$ is independently H, an optionally substituted $C_{1-6}$ alkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene)-$OR^f$, —$(C_{0-4}$ alkylene)-$(C_{1-4}$ alkene), —$(C_{0-4}$ alkylene)-$(C_{1-4}$ alkyne), $C_2$-$C_7$ heterocycle, —$(C_{0-4}$ alkylene)-C(=O)—$(C_1$-$C_6$ alkyl), —$(C_{0-4}$ alkylene)-C(=O)H, —$(C_{0-4}$ alkylene)-C(=O)$OR^f$, —$(C_{0-4}$ alkylene)-CN, —$(C_{0-4}$ alkylene)-halo, —$(C_{0-4}$ alkylene)-$NO_2$, —$(C_{0-4}$ alkylene)-$N(R^f)_2$, —$(C_{0-4}$ alkylene)-S(=O)$_2$—$(R^f)$, —$(C_{0-4}$ alkylene)-$(C_{6-14}$ aryl), —$(C_{1-4}$ alkylene)-(5- to 14-membered heteroaryl), —$(C_{0-4}$ alkylene)- C(=O)$NR^bR^f$ or —$(C_{0-4}$ alkylene)-$NR^bC$(=O)$R^f$;
wherein each $R^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
$L_3$ is a bivalent radical selected from —$(C_{2-6}$ alkenylene)- or —$(C_{2-6}$ alkynylene)-;
$L_4$ is a bivalent radical selected from —C(=O)—, —C(=O)O—, —C(=O)$NR^e$—, —$N(R^e)C$(=O)—, or —$(C_{1-4}$ alkylene)-;
$G_1$ and $G_2$ are each independently, at each occurrence, a bivalent radical selected from —$(C_{6-14}$ arylene)- or -(5- to 14-membered heteroarylene)-;
$G_3$ is H, $C_{3-7}$ cycloalkyl, $C_{3-10}$ heterocycloalkyl, $C_{6-14}$ aryl, 5- to 14-membered heteroarylene, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
$R^a$, $R^b$, $R^c$, $R^d$, and $R^e$ are each independently, at each occurrence, H or $C_{1-6}$ alkyl; and
n is 1 or 2.
In one embodiment,
$R_1$ is H or $C_{1-6}$ alkyl;
$R_2$ is H, —$OR^a$, $C_{1-6}$ alkyl, or $C_{1-6}$ alkoxy;
$R_3$ is —OH;
Z is O
$L_1$ is a bivalent radical selected from a bond, —C(=O)—, —C(=O)O—, —C(=O)$NR^b$—, —$N(R^b)$C(=O)—, —($C_{1-4}$ alkylene)-N($R^b$)—, or —($C_{1-4}$ alkylene)-S(=O)$_2$—;
$L_2$ is a bivalent radical selected from —$(C(R_4)(R_5))_n$—$(C_{0-3}$ alkylene)-, —$(C(R_4)(R_5))_n$—$C_{0-3}$ alkylene)-(C—

OR$^c$)—, —(C(R$_4$)(R$_5$))$_n$—(C$_{0-3}$ alkylene)-C(=O)—,
—(C(R$_4$)(R$_5$))$_n$—(C$_{0-3}$ alkylene)-C(=N—OH)—,
—(C(R$_4$)(R$_5$))$_n$—(C$_{0-3}$ alkylene)-(C(=O)NR$_5$)—,
—(C(R$_4$)(R$_5$))$_n$—(C$_{0-3}$ alkylene)-N(R$_5$)C(=O)—,
—(C(R$_4$)(R$_5$))$_n$—(C$_{0-3}$ alkylene)-O—, or —(C(R$_4$)(R$_5$))$_n$—(C$_{0-3}$ alkylene)-N(R$_5$)-;

wherein each R$_4$ is H or C$_{1-6}$ alkyl; and
each R$_5$ is independently H, C$_{1-6}$ alkyl, —(C$_{1-4}$ alkylene)-OR$^d$, —(C$_{1-4}$ alkylene)-N(R$^d$)$_2$, or —(C$_{1-4}$ alkylene)-S(=O)$_2$—(R$^d$);

L$_3$ is a bivalent radical —(C$_{1-6}$ alkynylene)-;
L$_4$ is a bivalent radical selected from —C(=O)—, —(C(=O)O)—, —(C(=O)NR$^e$)—, —N(R$^e$)C(=O)—, or —(C$_{1-4}$ alkylene)-;

G$_1$ and G$_2$ are each independently, at each occurrence, a bivalent radical selected from —(C$_6$ arylene)- or -(5- to 6-membered heteroarylene)-;

G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

R$^a$, R$^b$, R$^c$, R$^d$, and R$^e$ are each independently, at each occurrence, H or C$_{1-6}$ alkyl; and
n is 1 or 2.

In another embodiment,
R$_1$ is H or C$_{1-6}$ alkyl;
R$_2$ is H or C$_{1-6}$ alkyl;
R$_3$ is —OH;
Z is O;
L$_1$ is a bivalent radical selected from a bond, —C(=O)—, —(C(=O)O)—, —(C(=O)NR$^b$)—, or —N(R$^b$)C(=O)—;
L$_2$ is a bivalent radical —(C(R$_4$)(R$_5$))$_n$—(C$_{0-3}$ alkylene)-;
wherein each R$_4$ is H or C$_{1-6}$ alkyl; and
each R$_5$ independently is H, or C$_{1-6}$ alkyl;
L$_3$ is a bivalent radical —(C$_{1-6}$ alkynylene)-;
L$_4$ is a bivalent radical selected from —C(=O)— or —(C$_{1-4}$ alkylene)-;

G$_1$ and G$_2$ are each independently, at each occurrence, a bivalent radical selected from —(C$_6$ arylene)- or -(5- to 6-membered heteroarylene)-;

G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

R$^b$ is H or C$_{1-6}$ alkyl; and
n is 1.

In another embodiment,
L$_1$ bivalent radical selected from a bond, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—;
R$_2$ is H, —OR$^a$, —N(R$^a$)$_2$, C$_{1-6}$ alkyl, or C$_{1-6}$ alkoxy; and
R$^b$ is H or C$_{1-6}$ alkyl.

In another embodiment, R$_5$ is —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl).

In another aspect, one embodiment provided herein describes compounds having the structure of Formula IV:

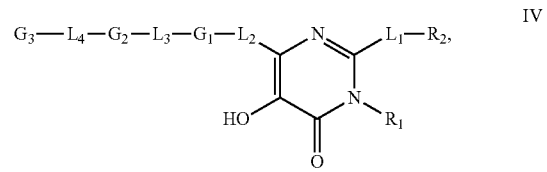

or a pharmaceutically acceptable salt thereof,
wherein:
R$_1$ is H or C$_{1-6}$ alkyl;
R$_2$ is H, —OR$^a$, —N(R$^a$)$_2$, C$_{1-6}$ alkyl, or C$_{1-6}$ alkoxy;
L$_1$ is a bivalent radical selected from a bond, —C(=O)—, —(C(=O)O)—, —OC(=O)—, —(C(=O)NR$^b$)—, —N(R$^b$)C(=O)—, —N(R$^b$)—, —S(=O)$_2$—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—;

L$_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-(C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;

wherein each R$_4$ is H or optionally substituted C$_{1-6}$ alkyl; and
each R$_5$ is independently H, an optionally substituted C$_{1-6}$ alkyl, an optionally substituted C$_{1-6}$ heteroalkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C (=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene) -N(R$^f$)$_2$, —(C$_{0-4}$ alkylene)-S(=O)$_2$-(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

L$_3$ is a bivalent radical selected from —(C$_{2-6}$ alkenylene)- or —(C$_{2-6}$ alkynylene)-;

L$_4$ is a bivalent radical selected from —C(=O)—, —(C(=O)O)—, —(C(=O)NR$^e$)—, —N(R$^e$)C(=O)—, or —(C$_{1-4}$ alkylene)-;

G$_1$ and G$_2$ are each independently, at each occurrence, a bivalent radical selected from —(C$_{6-14}$ arylene)- or -(5- to 14-membered heteroarylene)-;

G$_3$ is H, C$_{3-7}$ cycloalkyl, C$_{3-10}$ heterocycloalkyl, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy; and R$^a$, R$^b$, R$^c$, R$^d$, and R$^e$ are each independently, at each occurrence, H or C$_{1-6}$ alkyl; and n is 1 or 2.

In one embodiment,

R$_1$ is H or C$_{1-6}$ alkyl;

R$_2$ is H or C$_{1-6}$ alkyl;

L$_1$ is a bivalent radical selected from a bond, —C(=O)O—, —C(=O)NR$^b$—, —N(R$^b$)C(=O)—, a bond, —(C$_{1-4}$ alkylene)-O—, —(C$_{1-4}$ alkylene)-N(R$^b$)—, or —(C$_{1-4}$ alkylene)-S(=O)$_2$—;

L$_2$ is a bivalent radical is selected from —(C(R$_4$)(R$_5$))$_n$— (C$_{0-3}$ alkylene), or —(C(R$_4$)(R$_5$))$_n$—(C$_{0-3}$ alkylene)-N(R$_5$)—;

wherein each R$_4$ is H or an optionally substituted C$_{1-6}$ alkyl; and each R$_5$ is H or C$_{1-6}$ alkyl, —C(=O)NR$^b$R$^f$ or —(C$_{1-4}$ alkylene)-NR$^b$C(=O)R$^f$;

wherein R$^f$ is H, an optionally substituted C$_{1-6}$ alkyl, an optionally substituted C$_{1-6}$ heteroalkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl;

L$_4$ is a bivalent radical selected from —C(=O)—, —C(=O)O—, —C(=O)NR$^e$—, —N(R$^e$)C(=O)—, or —(C$_{1-4}$ alkylene)-;

G$_1$ and G$_2$ are each independently, at each occurrence, a bivalent radical selected from —(C$_{6-14}$ arylene)- or -(5- to 14-membered heteroarylene)-;

G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, or an optionally substituted alkoxy; and R$^b$ and R$^e$ are each independently, at each occurrence, H or C$_{1-6}$ alkyl; and n is 1 or 2.

In another embodiment, L$_1$ bivalent radical selected from a bond, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—; R$_2$ is H, —OR$^a$, —N(R$^a$)$_2$, C$_{1-6}$ alkyl, or C$_{1-6}$ alkoxy; and R$^b$ is H or C$_{1-6}$ alkyl.

In another embodiment, each R$_5$ is independently —(C$_{1-4}$ alkylene)-OR$^d$, —(C$_{1-4}$ alkylene)-N(R$^d$)$_2$, —(C$_{1-4}$ alkylene)-S(=O)$_2$-(R$^d$), —(C$_{1-4}$ alkylene)-(C$_{6-14}$ aryl), —(C$_{1-4}$ alkylene)-(5-to 14-membered heteroaryl), —C(=O)NR$^b$R$^f$ or —(C$_{1-4}$ alkylene)-NR$^b$C(=O)R$^f$;

wherein R$^f$ is H, an optionally substituted alkyl, an optionally substituted heteroalkyl, an optionally substituted cycloalkyl or an optionally substituted heterocyclyl.

Another embodiment provided herein describes a compound having the structure of Formula IVA:

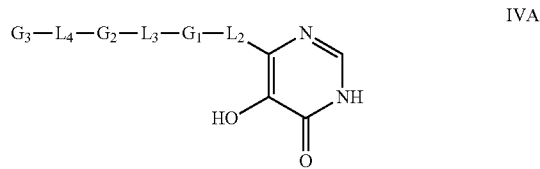

or a pharmaceutically acceptable salt thereof.

In one embodiment,

L$_2$ is a bivalent radical selected from —(C(R$_4$)(R$_5$))$_n$—(C$_{0-3}$ alkylene)-, —(C(R$_4$)(R$_5$))$_n$-C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—;

wherein each R$_4$ is H or optionally substituted C$_{1-6}$ alkyl; and each R$_5$ is independently H, an optionally substituted C$_{1-6}$ alkyl, an optionally substituted C$_{1-6}$ heteroalkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)-(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$-(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$;

wherein each R$^f$ is independently H, an optionally substituted alkyl, an optionally substituted cycloalkyl, an optionally substituted heterocyclyl, or an optionally substituted alkoxy;

L$_3$ is —(C$_{2-6}$ alkynylene)-;

L$_4$ is a bivalent radical selected from —C(=O)—, —(C(=O)O)—, —(C(=O)NR$^e$)—, —N(R$^e$)C(=O)—, or —(C$_{1-4}$ alkylene)-;

G$_1$ and G$_2$ are each independently, at each occurrence, —(C$_{6-14}$ arylene)-;

G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, or an optionally substituted alkoxy; and R$^a$, R$^b$, R$^c$, R$^d$, and R$^e$ are each independently, at each occurrence, H or C$_{1-6}$ alkyl; and n is 1 or 2.

In another embodiment,

L$_2$ is —(C(R$_4$)(R$_5$))$_n$—(C$_{0-3}$ alkylene)-, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—;

wherein each R$_4$ is H or optionally substituted C$_{1-6}$ alkyl; and each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene$)$-$OR^f$, —$(C_{0-4}$ alkylene$)$-$(C_{1-4}$ alkene), —$(C_{0-4}$ alkylene$)$-$(C_{1-4}$ alkyne), $C_2$-$C_7$ heterocycle, —$(C_{0-4}$ alkylene$)$-C$(=O)$—$(C_1$-$C_6$ alkyl), —$(C_{0-4}$ alkylene$)$-C$(=O)$H, —$(C_{0-4}$ alkylene$)$—C$(=O)OR^f$, —$(C_{0-4}$ alkylene$)$-CN, —$(C_{0-4}$ alkylene$)$-halo, —$(C_{0-4}$ alkylene$)$-$NO_2$, —$(C_{0-4}$ alkylene$)$—$N(R^f)_2$, —$(C_{0-4}$ alkylene$)$-S$(=O)_2$—$(R^f)$, —$(C_{0-4}$ alkylene$)$-$(C_{6-14}$ aryl), —$(C_{1-4}$ alkylene$)$-(5- to 14-membered heteroaryl), —$(C_{0-4}$ alkylene$)$- C$(=O)NR^bR^f$ or —$(C_{0-4}$ alkylene$)$-$NR^bC(=O)R^f$;

wherein each $R^f$ is independently H, an optionally substituted alkyl, an optionally substituted cycloalkyl, an optionally substituted heterocyclyl, or an optionally substituted alkoxy;

$L_3$ is —$(C_{2-6}$ alkynylene$)$-;

$L_4$ is —C$(=O)$—, —$(C(=O)O)$—, —$(C(=O)NR^e)$—, or —$(C_{1-4}$ alkylene$)$-;

$G_1$ and $G_2$ are each independently, at each occurrence, —$(C_{6-14}$ arylene$)$-;

$G_3$ is H, $C_{3-7}$ cycloalkyl, $C_{3-10}$ heterocycloalkyl, $C_{6-14}$ aryl, 5- to 14-membered heteroarylene, $(C_{1-4}$ alkylene$)$-$(C_{1-4}$ heteroalkyl), $(C_{1-4}$ alkylene$)$-$(C_{1-4}$ heterocycloalkyl), $(C_{3-10}$ heterocycloalkylene$)$-$(C_{1-4}$ alkyl), $(C_{3-10}$ heterocycloalkylene$)$-$(C_{1-4}$ heteroalkyl), $(C_{3-10}$ heterocycloalkylene$)$-$(C_{3-10}$ heterocycloalkyl), $C_{1-6}$ alkyl, or $(C_{3-10}$ heterocycloalkylene$)$-hydroxy; and $R^a$, $R^b$, $R^c$, $R^d$, and $R^e$ are each independently, at each occurrence, H or $C_{1-6}$ alkyl; and n is 1 or 2.

In yet another embodiment, $G_3$ is H, $C_{3-10}$ heterocycloalkyl, $(C_{1-4}$ alkylene$)$-$(C_{1-4}$ heteroalkyl), $(C_{1-4}$ alkylene$)$-$(C_{1-4}$ heterocycloalkyl), $(C_{3-10}$ heterocycloalkylene$)$-$(C_{1-4}$ heteroalkyl), $(C_{3-10}$ heterocycloalkylene$)$-$(C_{3-10}$ heterocycloalkyl), $C_{1-6}$ alkyl, $(C_{3-10}$ heterocycloalkylene$)$-hydroxy, or tetrazolyl.

Also provided herein in one embodiment is a compound having the structure of Formula IVB:

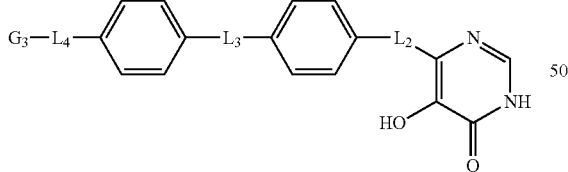

IVB or a pharmaceutically acceptable salt thereof.

In another embodiment, $L_2$ is a bivalent radical selected from —$(C(R_4)(R_5))_n$—$(C_{0-3}$ alkylene$)$-, —$(C(R_4)(R_5))_n$—$C_{0-3}$ alkylene$)$-$(C$—$OR^c)$—, —$(C(R_4)(R_5))_n$—$(C_{0-3}$ alkylene$)$-C$(=O)$—, —$(C(R_4)(R_5))_n$—$(C_{0-3}$ alkylene$)$-O—, —$(C(R_4)(R_5))_n$—$(C_{0-3}$ alkylene$)$-$N(R_5)$—, —$(C(R_4)(R_5))_n$—$(C_{0-3}$ alkylene$)$-S$(=O)_2$—;

wherein each $R_4$ is H or optionally substituted $C_{1-6}$ alkyl; and each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene$)$-$OR^f$, —$(C_{0-4}$ alkylene$)$-$(C_{1-4}$ alkene), —$(C_{0-4}$ alkylene$)$-$(C_{1-4}$ alkyne), $C_2$-$C_7$ heterocycle, —$(C_{0-4}$ alkylene$)$-C$(=O)$—$(C_1$-$C_6$ alkyl), —$(C_{0-4}$ alkylene$)$-C$(=O)$H, —$(C_{0-4}$ alkylene$)$-C$(=O)OR^f$, —$(C_{0-4}$ alkylene$)$-CN, —$(C_{0-4}$ alkylene$)$-halo, —$(C_{0-4}$ alkylene$)$-$NO_2$, —$(C_{0-4}$ alkylene$)$-$N(R^f)_2$, —$(C_{0-4}$ alkylene$)$-S$(=O)_2$—$(R^f)$, —$(C_{0-4}$ alkylene$)$-$(C_{6-14}$ aryl), —$(C_{1-4}$ alkylene$)$-(5- to 14-membered heteroaryl), —$(C_{0-4}$ alkylene$)$- C$(=O)NR^bR^f$ or —$(C_{0-4}$ alkylene$)$-$NR^bC(=O)R^f$;

wherein each $R^f$ is independently H, an optionally substituted alkyl, an optionally substituted cycloalkyl, an optionally substituted heterocyclyl, or an optionally substituted alkoxy;

$L_3$ is —$(C_{2-6}$ alkynylene$)$-;

$L_4$ is a bivalent radical selected from —C$(=O)$—, —$(C(=O)O)$—, —$(C(=O)NR^e)$—, —$N(R)C(=O)$—, or —$(C_{1-4}$ alkylene$)$-;

$G_3$ is H, $C_{3-7}$ cycloalkyl, $C_{3-10}$ heterocycloalkyl, $C_{6-14}$ aryl, 5- to 14-membered heteroarylene, $(C_{1-4}$ alkylene$)$-$(C_{1-4}$ heteroalkyl), $(C_{3-10}$ heterocycloalkylene$)$-$(C_{1-4}$ alkyl), $(C_{3-10}$ heterocycloalkylene$)$-$(C_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, or an optionally substituted alkoxy; and $R^a$, $R^b$, $R^c$, $R^d$, and $R^e$ are each independently, at each occurrence, H or $C_{1-6}$ alkyl; and n is 1 or 2.

In another embodiment, $L_2$ is —$(C(R_4)(R_5))_n$—$(C_{0-3}$ alkylene$)$-, —$(C(R_4)(R_5))_n$—$(C_{0-3}$ alkylene$)$-$N(R_5)$—, —$(C(R_4)(R_5))_n$—$(C_{0-3}$ alkylene$)$-S$(=O)_2$—;

wherein each $R_4$ is H or optionally substituted $C_{1-6}$ alkyl; and each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene$)$-$OR^f$, —$(C_{0-4}$ alkylene$)$-$(C_{1-4}$ alkene), —$(C_{0-4}$ alkylene$)$-$(C_{1-4}$ alkyne), $C_2$-$C_7$ heterocycle, —$(C_{0-4}$ alkylene$)$-C$(=O)$—$(C_1$-$C_6$ alkyl), —$(C_{0-4}$ alkylene$)$-C$(=O)$H, —$(C_{0-4}$ alkylene$)$-C$(=O)OR^f$, —$(C_{0-4}$ alkylene$)$-CN, —$(C_{0-4}$ alkylene$)$-halo, —$(C_{0-4}$ alkylene$)$-$NO_2$, —$(C_{0-4}$ alkylene$)$-$N(R^f)_2$, —$(C_{0-4}$ alkylene$)$-S$(=O)_2$—$(R^f)$, —$(C_{0-4}$ alkylene$)$-$(C_{6-14}$ aryl), —$(C_{1-4}$ alkylene$)$-(5- to 14-membered heteroaryl), —$(C_{0-4}$ alkylene$)$- C$(=O)NR^bR^f$ or —$(C_{0-4}$ alkylene$)$-$NR^bC(=O)R^f$;

wherein each $R^f$ is independently H, an optionally substituted alkyl, an optionally substituted cycloalkyl, an optionally substituted heterocyclyl, or an optionally substituted alkoxy;

$L_3$ is —$(C_{2-6}$ alkynylene$)$-;

$L_4$ is —C$(=O)$—, —$(C(=O)O)$—, —$(C(=O)NR^e)$—, or —$(C_{1-4}$ alkylene$)$-;

$G_3$ is H, $C_{3-7}$ cycloalkyl, $C_{3-10}$ heterocycloalkyl, $C_{6-14}$ aryl, 5- to 14-membered heteroarylene, $(C_{1-4}$ alkylene$)$-$(C_{1-4}$ heteroalkyl), $(C_{1-4}$ alkylene$)$-$(C_{1-4}$ heterocycloalkyl), $(C_{3-10}$ heterocycloalkylene$)$-$(C_{1-4}$ alkyl), $(C_{3}$-

10 heterocycloalkylene)-($C_{1-4}$ heteroalkyl), ($C_{3-10}$ heterocycloalkylene)-($C_{3-10}$ heterocycloalkyl), $C_{1-6}$ alkyl, or ($C_{3-10}$ heterocycloalkylene)-hydroxy; and $R^a$, $R^b$, $R^c$, $R^d$, and $R^e$ are each independently, at each occurrence, H or $C_{1-6}$ alkyl; and n is 1 or 2.

In another embodiment, $G_3$ is H, $C_{3-10}$ heterocycloalkyl, ($C_{1-4}$ alkylene)-($C_{1-4}$ heteroalkyl), ($C_{1-4}$ alkylene)-($C_{1-4}$ heterocycloalkyl), ($C_{3-10}$ heterocycloalkylene)-($C_{1-4}$ heteroalkyl), ($C_{3-10}$ heterocycloalkylene)-($C_{3-10}$ heterocycloalkyl), $C_{1-6}$ alkyl, ($C_{3-10}$ heterocycloalkylene)-hydroxy, or tetrazolyl.

In another aspect, the present disclosure provides compounds having the structure of Formula V:

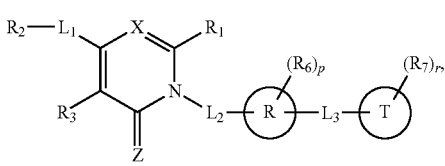

V or a pharmaceutically acceptable salt thereof,
wherein:
$R_1$ is H, —OH, —$NH_2$, or SH;
$R_2$ is H, —$OR^a$, —$N(R^a)_2$, $C_{1-6}$ alkyl, or $C_{1-6}$ alkoxy;
$R_3$ is H, —OH, —$NH_2$, or SH;
$R_6$ and $R_7$ are each independently, at each occurrence, —OH, —$NH_2$, —CN, —$NO_2$, —C(=O)$OR^b$, —C(=O) N($R^b$)$_2$, —N($R^b$)C(=O)$OR^b$, halo, $C_{1-6}$ alkyl, $C_{1-6}$ alkoxy, =O, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
ring R is $C_{3-7}$ cycloalkyl, $C_{3-10}$ heterocycloalkyl, $C_{6-14}$ aryl, or a 5- to 14-membered heteroaryl;
ring T is $C_{3-7}$ cycloalkyl, $C_{3-10}$ heterocycloalkyl, $C_{6-14}$ aryl, or a 5- to 14-membered heteroaryl;
X is CH, S, or N;
Z is O or S;
$L_1$ is a bivalent radical selected from a bond, —C(=O)—, —(C(=O)O)—, —OC(=O)—, —C(=O)$NR^c$—, —$N(R^c)$C(=O)—, —$N(R^c)$—, —$S(=O)_2$—, —($C_{1-4}$ alkylene)-, —($C_{1-4}$ alkylene)-O—, —($C_{1-4}$ alkylene)-N($R^c$)—, —($C_{1-4}$ alkylene)-S—, or —($C_{1-4}$ alkylene)-S(=O)$_2$—;
$L_2$ is a bivalent radical selected from —(C($R_4$)($R_5$))$_n$($C_{0-3}$ alkylene)-, —(C($R_4$)($R_5$))$_n$—$C_{0-3}$ alkylene)-(C=$OR^c$)—, —(C($R_4$)($R_5$))$_n$—($C_{0-3}$ alkylene)-C(=O)—, —(C($R_4$)($R_5$))$_n$—($C_{0-3}$ alkylene)-C(=N—OH)—, —(C($R_4$)($R_5$))$_n$—($C_{0-3}$ alkylene)-C(=O)N$R_5$)—, —(C($R_4$)($R_5$))$_n$—($C_{0-3}$ alkylene)-N($R_5$)C(=O)—, —(C($R_4$)($R_5$))$_n$—($C_{0-3}$ alkylene)-O—, —(C($R_4$)($R_5$))$_n$—($C_{0-3}$ alkylene)-N($R_5$)—, —(C($R_4$)($R_5$))$_n$—($C_{0-3}$ alkylene)-S(=O)$_2$—, —(C($R_4$)($R_5$))$_n$—($C_{0-3}$ alkylene)-S(=O)$_2$N($R_5$)—, or —(C($R_4$)($R_5$))$_n$—($C_{0-3}$ alkylene)-N($R_5$)S(=O)$_2$—;
wherein each $R_4$ is H or optionally substituted $C_{1-6}$ alkyl; and
each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —($C_{0-4}$ alkylene)-$OR^f$, —($C_{0-4}$ alkylene)-($C_{1-4}$ alkene), —($C_{0-4}$ alkylene)-($C_{1-4}$ alkyne), $C_2$-$C_7$ heterocycle, —($C_{0-4}$ alkylene)-C(=O)—($C_1$-$C_6$ alkyl), —($C_{0-4}$ alkylene)-C(=O)H, —($C_{0-4}$ alkylene)-C(=O)$OR^f$, —($C_{0-4}$ alkylene)-CN, —($C_{0-4}$ alkylene)-halo, —($C_{0-4}$ alkylene)-$NO_2$, —($C_{0-4}$ alkylene)-N($R^f$)$_2$, —($C_{0-4}$ alkylene)-S(=O)$_2$—($R^f$), —($C_{0-4}$ alkylene)-($C_{6-14}$ aryl), —($C_{1-4}$ alkylene)-(5- to 14-membered heteroaryl), —($C_{0-4}$ alkylene)- C(=O)N$R^b R^f$ or —($C_{0-4}$ alkylene)-N$R^b$C(=O)$R^f$;
wherein each $R^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
$L_3$ is a bivalent radical selected from a bond, —($C_{1-6}$ alkylene)-, —($C_{2-6}$ alkenylene)-, or —($C_{2-6}$ alkynylene)-, —($C_{3-10}$ heterocycloalkylene)-, —($C_{6-14}$ arylene)-, -(5- to 14-membered heteroarylene)-;
$R^a$, $R^b$, $R^c$, $R^d$, and $R^e$ are each independently, at each occurrence, H or $C_{1-6}$ alkyl;
n is 1 or 2;
p is 0, 1, 2, or 3; and
r is 0, 1, 2, or 3.

In one embodiment, $R_5$ is —($C_{1-4}$ alkylene)-$OR^d$, —($C_{1-4}$ alkylene)-N($R^d$)$_2$, —($C_{1-4}$ alkylene)-S(=O)$_2$—($R^d$), —($C_{1-4}$ alkylene)-($C_{6-14}$ aryl), or —($C_{1-4}$ alkylene)-(5- to 14-membered heteroaryl).

In another embodiment, p is 1, and $R_6$ is =O.

In yet another aspect, the present disclosure provides compounds having the structure of Formula VI:

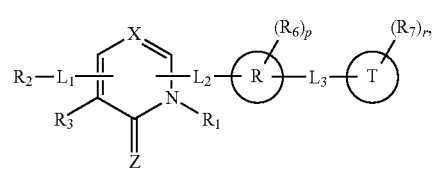

VI or a pharmaceutically acceptable salt thereof,
wherein:
$R_1$ is H, $C_{1-6}$ alkyl, —OH, —$NH_2$, or SH;
$R_2$ is H, —$OR^a$, —$N(R^a)_2$, $C_{1-6}$ alkyl, or $C_{1-6}$ alkoxy;
$R_3$ is H, $C_{1-6}$ alkyl, —OH, —$NH_2$, or SH;
$R_6$ and $R_7$ are each independently, at each occurrence, —OH, —$NH_2$, —CN, —$NO_2$, —C(=O)$OR^b$, —C(=O) N($R^b$)$_2$, —N($R^b$)C(=O)$OR^b$, halo, $C_{1-6}$ alkyl, $C_{1-6}$ alkoxy, =O, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
ring R is $C_{3-7}$ cycloalkyl, $C_{3-10}$ heterocycloalkyl, $C_{6-14}$ aryl, or a 5- to 14-membered heteroaryl;
ring T is $C_{3-7}$ cycloalkyl, $C_{3-10}$ heterocycloalkyl, $C_{6-14}$ aryl, or a 5- to 14-membered heteroaryl;
X is C(H), S, or N;
Z is O or S;

$L_1$ is a bivalent radical selected from a bond, —C(=O)—, —(C(=O)O)—, —OC(=O)—, —(C(=O)NR$^b$)—, —N(R$^b$)C(=O)—, —N(R$^b$)—, —S(=O)$_2$—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, or —(C$_{1-4}$ alkyl ene)-S(=O)$_2$—;

$L_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$^5$)S(=O)$_2$—;

wherein each $R_4$ is H or optionally substituted $C_{1-6}$ alkyl; and each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —(C$_{0-4}$ alkylene)OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from a bond, —(C$_{1-6}$ alkylene)-, —(C$_{2-6}$ alkenylene)-, or —(C$_{2-6}$ alkynylene)-, —(C$_{3-10}$ heterocycloalkylene)-, —(C$_{6-14}$ arylene)-, -(5- to 14-membered heteroarylene)-;

R$^a$ R$^b$, R$^c$, R$^e$, R$^d$, and R$^e$ are each independently, at each occurrence, H or C$_{1-6}$ alkyl;

n is 1 or 2;

p is 0, 1, 2, or 3; and r is 0, 1, 2, or 3.

In one embodiment, $R_5$ is —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl).

In another embodiment, p is 1, and $R_6$ is =O.

One embodiment provided herein describes a method of modulating the activity of UDP-{3-O—[(R)-3-hydroxymyristoyl]}-N-acetylglucosamine deacetylase in a subject in need thereof comprising administering a therapeutically effective amount of a compound described herein, or a pharmaceutically acceptable salt thereof.

Also provided herein is a method of treating a gram-negative bacterial infection in a subject comprising administering to the subject a pharmaceutical composition comprising a compound described herein, or a pharmaceutically acceptable salt thereof.

Another embodiment provided herein describes a pharmaceutical composition comprising a therapeutically effective amount of a compound described herein and a pharmaceutically acceptable excipient.

DETAILED DESCRIPTION OF THE INVENTION

Definitions

Figure 1:
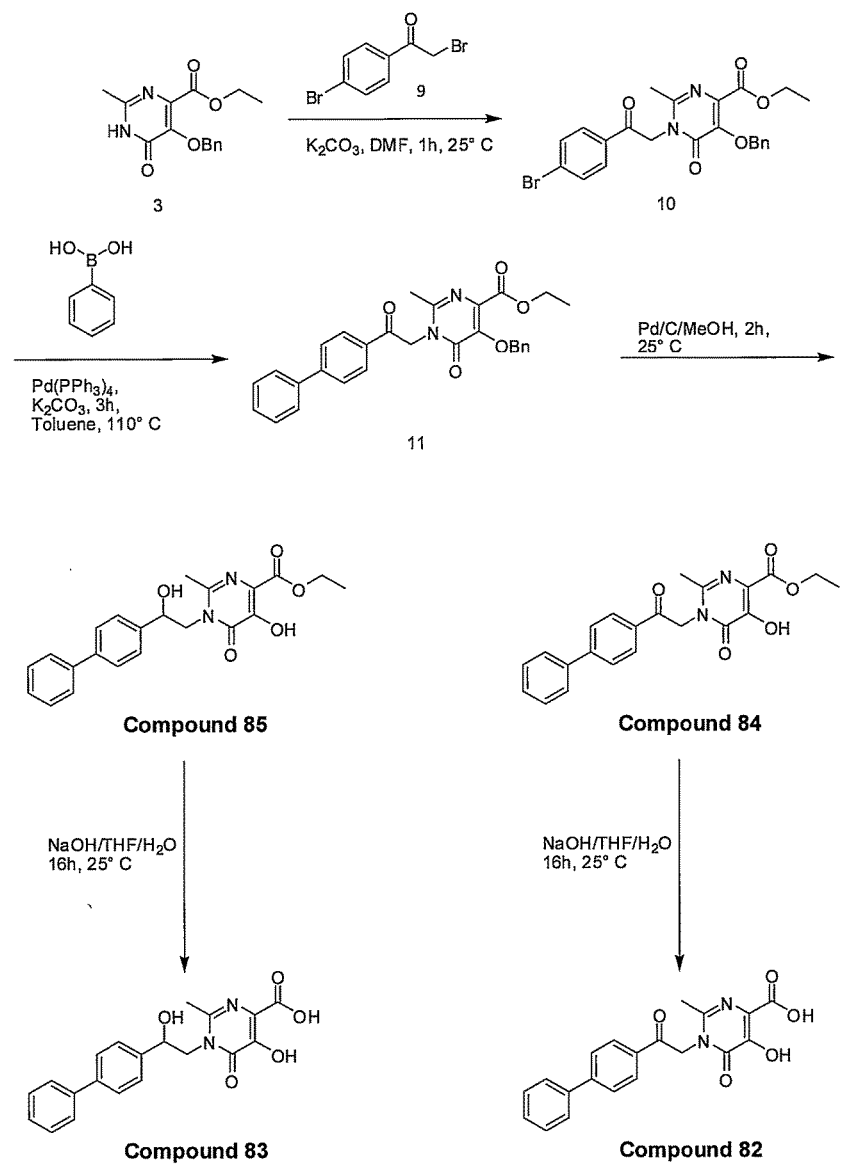
FIG. 1 shows a synthetic scheme to prepare compounds 82, 83, 84 and 85.

As used herein, "treatment," "treating," "treat and the like refer generally to obtaining a desired pharmacological or physiological effect. The treatment may be therapeutic in terms of partial or complete stabilization or cure of a disease or adverse effects caused by the disease. "Treatment" as used herein covers any treatment of a disease in a subject, including: (a) inhibiting the symptoms of a disease, i.e., arresting its development; or (b) relieving the symptoms of a disease, i.e., causing regression of the disease or symptoms.

The phrase "therapeutically effective amount" as used herein means that amount of a compound, material, or composition comprising a compound of the present teachings that is effective for producing a desired therapeutic effect. Accordingly, a therapeutically effective amount treats a disease or a disorder, e.g., ameliorates at least one sign or symptom of the disorder. In various embodiments, the disease or disorder is a bacterial infection.

The term "alkyl" or "alkylene" as used herein refers to a fully saturated straight or branched hydrocarbon. Preferably the alkyl comprises 1-22 carbon atoms, more preferably 1-16 carbon atoms, 1-8 carbon atoms, 1-6 carbon atoms, or 1-4 carbon atoms. Exemplary alkyl groups include, but are not limited to, methyl, ethyl, n-propyl, iso-propyl, n-butyl, sec-butyl, iso-butyl, tent-butyl, n-pentyl, isopentyl, neopentyl, n-hexyl, 3-methylhexyl, 2,2- dimethylpentyl, 2,3-dimethylpentyl, n-heptyl, n-octyl, n-nonyl, n-decyl. Furthermore, the expression "C$_x$-C$_y$-alkyl", wherein x is 1-5 and y is 2-10 indicates a particular alkyl group (straight- or branched-chain) of a particular range of carbons. For example, the expression C$_1$-C$_4$-alkyl includes, but is not limited to, methyl, ethyl, propyl, butyl, isopropyl, tert-butyl and isobutyl. Alkyl groups may be substituted with one or more substituents, each of which is independently selected from, e.g., (a) oxo (=O), fluoro (—F), chloro bromo (—Br), iodo (—I), cyano (—CN), and nitro (—NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or C$_{1-6}$ alkyl.

The term "alkenyl" or "alkenylene," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups include, but are not limited to, ethenyl, 1-propenyl, 2-propenyl, isopropenyl, 1-butenyl, 2-butenyl, 3-butenyl, isobutenyl, 1-cyclopentenyl, 1-cyclohexenyl, and 2,4-hexadiene. Alkenyl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or C$_{1-6}$ alkyl.

The term "alkynyl" or "alkynylene" alone or in combination refers to a straight-chain, cyclic or branched hydrocarbon residue comprising at least one carbon-carbon triple bond and the indicated number of carbon atoms. The alkynyl may contain one, two, or three carbon-carbon triple bonds. Preferred alkynyl groups have up to 8, preferably up to 6, particularly preferred up to 4 carbon atoms. Examples of alkynyl groups include, but are not limited to, ethyne (or acetylene), 1-propyne, 2-propyne, 1-butyne, 2-butyne, 3-butyne, isobutyne, 1-cyclopentynyl, 1-cyclohexynyl, and 2,4-hexadiyne. Alkynyl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$_a$C(O)R$^d$, —NR$^a$C(O)OR$^d$, —NR$^a$C(O)NR$^b$R$^c$, —NR$^a$C (=NR$^d$)NR$^b$R$^c$, —NR$^a$S(O)R$^d$, —NR$^a$S(O)$^2$R$^d$, —NR$^a$S(O)NR$^b$R$^c$, —NR$^a$S(O)$^2$NR$^b$R$^c$, —P(O)R$^a$R$^d$, —P(O)(OR$^a$)R$^d$, —P(O)(OR)$^a$(OR$^d$), —SR$^a$, —S(O)R$^a$, —S(O)$_2$R$^a$, —S(O)$^2$R$^a$, —S(O)NR$^b$R$^c$, and —S(O)$_2$NR$^b$R$^d$, wherein each R$^a$, R$^b$, R$^c$, R$^d$, and R$^e$ are each independently, at each occurrence, H or C$_{1-6}$ alkyl.

The term "alkoxy" represents a chemical substituent of formula —OR, where R is a C$_{1-20}$ alkyl group (e.g., C$_{1-6}$ or C$_{1-10}$ alkyl), unless otherwise specified. An alkoxy group refers to those alkyl groups, having from 1 to 20 carbon atoms, attached to the remainder of the molecule via an oxygen atom. Exemplary alkoxy groups include methoxy, ethoxy, propoxy (e.g., n-propoxy and isopropoxy), t-butoxy, and the like. In some embodiments, the alkyl group can be further substituted with 1, 2, 3, or 4 substituent groups as defined herein (e.g., hydroxy or alkoxy).

The term "cycloalkyl" or "carbocyclic" as used herein refers to a saturated or unsaturated monocyclic, bicyclic, tricyclic, other multicyclic, or bridged cyclic hydrocarbon group. A cycloalkyl group can have 3-22 ring carbon atoms, 3-12 ring carbon atoms, or 3-7 ring carbon atoms, referred to herein as C$_3$-C$_{22}$ cycloalkyl, C$_3$-C$_{12}$ cycloalkyl, or C$_3$-C$_7$ cycloalkyl, respectively. A cycloalkyl group can also have one or more carbon-carbon double bond or carbon-carbon triple bond. Cycloalkyl groups may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or C$_{1-6}$ alkyl.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like. Cycloalkyl groups can be fused to other cycloalkyl saturated or unsaturated, aryl, or heterocyclyl groups.

The term "aryl" or "arylene" as used herein refers to a mono-, bi-, or other multi-carbocyclic aromatic ring system.

The aryl can have 6-14 carbon atoms, or 6-10 carbon atoms, referred to herein as $C_6$-$C_{14}$ aryl, or $C_6$-$C_{10}$ aryl, respectively. The aryl group can optionally be fused to one or more rings selected from aryls and cycloalkyls. The ring systems may be partially saturated. The term "biaryl" as used herein refers to an aryl group fused or bridged to another aromatic or non-aromatic carbocyclic. The aryl may be $C_{6\text{-}20}$ biaryl. Exemplary aryl groups include, but are not limited to, phenyl, biphenyl, tolyl, anthracenyl, xylyl, anthryl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$C_6$ aryl" or phenyl. The phenyl group can also be fused to a cyclohexane or cyclopentane ring to form a biaryl. Aryl groups may be substituted with one or more substituents, each of which is independently selected from, e.g., (a) oxo (=O), fluoro (—F), chloro (—CO, bromo (—Br), iodo (—I), cyano (—CN), and nitro (—$NO_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —P(O)$R^aR^d$, —P(O)(O$R^a$)$R^d$, —P(O)(O$R^a$)(O$R^d$), —S$R^a$, —S(O)$R^a$, —S(O)$_2R^a$, —S(O)N$R^bR^c$, and —S(O)$_2$N$R^bR^c$, wherein each $R^a$, $R^b$, $R^c$, $R^d$, and $R^e$ are each independently, at each occurrence, H or $C_{1-6}$ alkyl.

The term "heterocycle" or "heterocyclyl" refers to a fully saturated or partially unsaturated nonaromatic monocyclic, bicyclic, tricyclic, other multicyclic, or bridged heterocyclic group containing at least one heteroatom such as nitrogen, oxygen, or sulfur. In some cases, the heterocycle can be 3- to 22-membered rings, 4- to 13-membered ring structures or 3- to 7-membered rings, whose ring structures include one to four heteroatoms. The heterocycle may also be referred to as $C_{3-10}$ heterocycloalkyl comprising 3 to 10 carbon atoms and 1 to 3 heteroatoms to form a 4- to 13-membered heterocycloalkyl. Nonlimiting examples include piperidinyl, morpholinyl, piperazinyl, pyrrolidinyl or pirazinyl. In some case, the heterocycle is a nitrogen heterocycle, wherein at least one ring comprises at least one nitrogen ring atom. The heterocycles may be fused to other rings to form a polycyclic heterocycloalkyl. Thus, heterocycloalkyls also include bicyclic, tricyclic, and tetracyclic groups in which any of the above heterocyclic rings is fused to one or two rings independently selected from cycloalkyls, and heterocycles. The heterocycle may also be fused to a spirocyclic group. Heterocycle groups may be substituted with one or more substituents, each of which is independently selected from, e.g., (a) oxo (=O), fluoro (—F), chloro (—Cl), bromo (—Br), iodo (—I), cyano (—CN), and nitro (—$NO_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)$R^a$, —C(O)O$R^a$, —C (O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —P(O)$R^aR^d$, —P(O)(O$R^a$)$R^d$, —P(O)(O$R^a$)(O$R^d$), —S$R^a$, —S(O)$R^a$, —S(O)$_2R^a$, —S (O)N$R^bR^c$, and —S(O)$_2$N$R^bR^c$, wherein each $R^a$, $R^b$, $R^c$, $R^d$, and $R^e$ are each independently, at each occurrence, H or $C_{1-6}$ alkyl.

Heterocycle groups within the scope of this definition include but are not limited to imidazolyl, isothiazolyl, thiazolyl, triazinyl, triazolyl, pyrolidinyl, pyrrolinyl, piperidinyl, morpholinyl, piperazinyl, thiomorpholinyl, pyranyl and pyrazlonyl.

The term "heteroaromatic," "heteroaryl," or "heteroarylene" as used herein refers to a mono-, bi-, tricyclic, or multi-cyclic aromatic ring system containing one or more heteroatoms, for example 1-4 heteroatoms, such as nitrogen, oxygen, and sulfur. For example, a bicyclic aromatic ring system containing one or more heteroatoms includes, but is not limited to, phenylpyridine, triazolylpyridine, oxazolylpyridine, thiazolylpyridine, and imidazolylpyridine. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or a stable 12- to 14-membered fused tricyclic heterocyclic ring system, or a stable 5- to 14-membered heteroarylene, which contains an aromatic ring that contains at least one heteroatom selected from the group consisting of nitrogen, oxygen, and sulfur. In some embodiments, at least one nitrogen atom is in the aromatic ring. Heteroaryl groups may be substituted with one or more substituents, each of which is independently selected from, e.g., (a) oxo (=O), fluoro (—F), chloro (—Cl), bromo (—Br), iodo (—I), cyano (—CN), and nitro (—$NO_2$); (b) substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-10}$ cycloalkyl, substituted or unsubstituted $C_{6-14}$ aryl, substituted or unsubstituted $C_{7-15}$ aralkyl, substituted or unsubstituted heteroaryl, and substituted or unsubstituted heterocyclyl; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —P(O)$R^aR^d$, —P(O)(O$R^a$)$R^d$, —P(O)(O$R^a$)(O$R^d$), —S$R^a$, —S(O)$R^a$, S(O)$_2R^a$, S(O)N$R^bR^c$, and —S(O)$_2$N$R^bR^c$, wherein each $R^a$, $R^b$, $R^c$, $R^d$, and $R^e$ are each independently, at each occurrence, H or $C_{1-6}$ alkyl.

The terms "heterobiaryl" and "heterobicycloalkyl" as used herein refers to a heteroaryl group fused to another aromatic or non-aromatic carbocyclic or heterocyclic ring. Exemplary heterobiaryls and heterobicycloalkyls include, but are not limited to 5,6- or 6,6-fused systems, wherein one or both rings contain heteroatoms. The term heterobiaryl or heterobicycloalkyl also encompasses reduced or partly reduced forms of fused aromatic system wherein one or both rings contain ring heteroatoms. The ring system may contain up to four heteroatoms, independently selected from oxygen, nitrogen, and sulfur. These groups may also be referred to as "$C_{8-11}$ heterobiaryl," "fused 5- to 12-membered heterobicycloalkyl," and fused 8- to 11-membered heterobiaryl. Heterobiaryl groups may be substituted with one or more substituents, each of which is independently selected from, e.g., (a) oxo (=O), fluoro (—F), chloro (—Cl), bromo (—Br), iodo (—I), cyano (—CN), and nitro (NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or C$_{1-6}$ alkyl.

Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline.

The terms "halo" or "halogen," by themselves or as part of another substituent, mean, unless otherwise stated, a fluorine, chlorine, bromine, or iodine atom.

The terms "hydroxy" and "hydroxyl" as used herein refers to —OH.

The term "nitro" as used herein refers to —NO$_2$.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)-or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

The term "optionally substituted" is intended to mean that a group or substituent, such as an alkyl, alkylene, heteroalkylene, alkenyl, alkenylene, heteroalkenylene, alkynyl, cycloalkyl, cycloalkenyl, aryl, aralkyl, heteroaryl, heteroaryl-C$_{1-6}$ alkyl, and heterocyclyl group, may be substituted with one or more substituents, each of which is independently selected from, e.g., (a) oxo (=O), fluoro (—F), chloro (—Cl), bromo (—Br), iodo (—I), cyano (—CN), and nitro (—NO$_2$); (b) substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-10}$ cycloalkyl, substituted or unsubstituted C$_{6-14}$ aryl, substituted or unsubstituted C$_{7-15}$ aralkyl, substituted or unsubstituted heteroaryl, and substituted or unsubstituted heterocyclyl; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, R$^d$, and R$^e$ are each independently, at each occurrence, H or C$_{1-6}$ alkyl.

The term "metal" as used herein refers to metals in elemental form, metal atoms, and metal ions interchangeably. The term "metal" also encompasses metal radioisotopes.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Compounds of the Disclosure

The present disclosure provides hydroxypyridinone and hydroxypyrimidinone derivatives, pharmaceutical compositions thereof, and methods of using such compounds to treat or alleviate a disease or condition. Provided herein are compounds and compositions thereof useful to treat bacterial infections.

In one aspect, the disclosure provides a metal-binding compound comprising a hydroxypyridinone or a hydroxypyrimidinone derivative. In some embodiments, the metal-binding compound has the following structural formula with the positional numbering below:

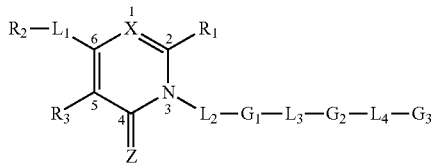

In another embodiment, a compound of the disclosure has the following structural formula:

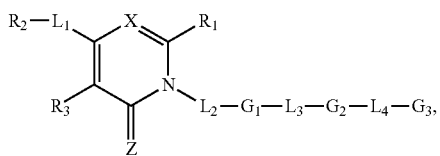

I or a pharmaceutically acceptable salt thereof,
wherein:
$R_1$ is H, $C_{1-6}$ alkyl, or $C_{1-6}$ alkoxy;
$R_2$ is H, —$OR^a$, —$N(R^a)_2$, $C_{1-6}$ alkyl, or $C_{1-6}$ alkoxy;
$R_3$ is —OH, —$NH_2$, or SH;
X is CH, S, or N;
Z is O or S;
$L_1$ is a bivalent radical selected from a bond, —C(=O)—, —(C(=O)O)—, —OC(=O)—, —(C(=O)$NR^b$)—, —$N(R^b)$C(=O)—, —$N(R^b)$—, —S(=O)$_2$—, —($C_{1-4}$ alkylene)-, —($C_{1-4}$ alkylene)-O—, —($C_{1-4}$ alkylene)-$N(R^b)$—, —($C^{1-4}$ alkylene)-S—, or —($C_{1-4}$alkylene)-S(=O)$_2$—;
$L_2$ is a bivalent radical selected from —C($R_4$)($R_5$)$_n$—($C_{0-3}$ alkylene)-, —(C($R_4$)($R_5$))$_n$—$C_{0-3}$ alkylene)-(C—$OR^c$)—, —(C($R_4$)($R_5$))$_n$—($C_{0-3}$ alkylene)-C(=O)—, —(C($R_4$)($R_5$))$_n$—($C_{0-3}$ alkylene)-C(=N—OH)—, —(C($R_4$)($R_5$))$_n$—($C_{0-3}$ alkylene)-(C(=O)$NR_5$)—, —(C($R_4$)($R_5$))$_n$—($C_{0-3}$ alkylene)-$N(R_5)$C(=O)—, —(C($R_4$)($R_5$))$_n$—($C_{0-3}$ alkylene)-O—, —(C($R_4$)($R_5$))$_n$—($C_{0-3}$ alkylene)-$N(R_5)$—, —(C($R_4$)($R_5$))$_n$—($C_{0-3}$ alkylene)-S(=O)$_2$—, —(C($R_4$)($R_5$))$_n$—($C_{0-3}$ alkylene)-S(=O)$_2$$N(R_5)$—, or —(C($R_4$)($R_5$))$_n$—($C_{0-3}$ alkylene)-$N(R_5)$S(=O)$_2$—;
wherein each $R_4$ is H or $C_{1-6}$ alkyl; and
each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —($C_{0-4}$ alkylene)-$OR^f$, —($C_{0-4}$ alkylene)-($C_{1-4}$ alkene), —($C_{0-4}$ alkylene)-($C_{1-4}$ alkyne), $C_2$-$C_7$ heterocycle, —($C_{0-4}$ alkylene)-C(=O)—($C_{1-6}$ alkyl), —($C_{0-4}$ alkylene)-C(=O)H, —($C_{0-4}$ alkylene)-C(=O)$OR^f$, —($C_{0-4}$ alkylene)-CN, —($C_{0-4}$ alkylene)-halo, —($C_{0-4}$ alkylene)-$NO_2$, —($C_{0-4}$ alkylene)-$N(R^f)_2$, —($C_{0-4}$ alkylene)-S(=O)$_2$—($R^f$), —($C_{0-4}$ alkylene)-($C_{6-14}$ aryl), —($C_{1-4}$ alkylene)-(5- to 14-membered heteroaryl), —($C_{0-4}$ alkylene)- C(=O)$NR^b R^f$ or —($C_{0-4}$ alkylene)-$NR^b C$(=O)$R^f$;
wherein each $R^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from a bond, —($C_{1-6}$ alkylene)-, —($C_{2-6}$ alkenylene)-, —($C_{2-6}$ alkynylene)-, —($C_{3-10}$ heterocycloalkylene)-, —($C_{6-14}$ arylene)-, or -(5- to 14-membered heteroarylene)-;
$L_4$ is a bivalent radical selected from a bond, —C(=O)—, —(C(=O)O)—, —OC(=O)—, —(C(=O)$NR^e$)—, —$N(R^e)$C(=O)—, —$N(R^e)$—, —S(=O)$_2$—, or —($C_{1-4}$ alkylene)-;
$G_1$ and $G_2$ are each independently, at each occurrence, a bivalent radical selected from —($C_{6-14}$ arylene)- or -(5- to 14-membered heteroarylene)-;
$G_3$ is H, CN, $C_{1-6}$ alkyl, $C_{3-7}$ cycloalkyl, $C_{3-10}$ heterocycloalkyl, $C_{6-14}$ aryl, 5- to 14-membered heteroarylene, fused 5- to 12-membered heterobicycloalkyl, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl), (5- to 14-membered heteroarylene)-($C_{1-4}$ heteroalkyl), (fused 5- to 12-membered heterobicycloalkyl)-($C_{1-4}$ heteroalkyl), or (fused 8- to 11-membered heterobiaryl)-($C_{1-4}$ heteroalkyl);
and
$R^a$, $R^b$, $R^c$, $R^d$, and $R^e$ are each independently, at each occurrence, H or $C_{1-6}$ alkyl; and
n is 1 or 2.
In some embodiments, $L_2$ is substituted or unsubstituted $C_{1-3}$ alkylene, substituted or unsubstituted $C_{0-3}$ alkylene-(C—$OR^c$)—, substituted or unsubstituted $C_{0-3}$ alkylene-C(=O)—, substituted or unsubstituted $C_{0-3}$ alkylene-C(=N—OH)—, substituted or unsubstituted $C_{0-3}$ alkylene-(C(=O)$NR_5$)—, substituted or unsubstituted $C_{0-3}$ alkylene-$N(R_5)$C(=O)—, substituted or unsubstituted $C_{0-3}$ alkylene-O—, substituted or unsubstituted $C_{0-3}$ alkylene-$N(R_5)$—, substituted or unsubstituted $C_{0-3}$ alkylene-S(=O)$_2$—, substituted or unsubstituted $C_{0-3}$ alkylene-S(=O)$_2$$N(R_5)$—, or substituted or unsubstituted $C_{0-3}$ alkylene-$N(R_5)$S(=O)$_2$—.
In some embodiments, $L_2$ is substituted or unsubstituted $C_{1-3}$ alkylene, substituted or unsubstituted $C_{0-3}$ alkylene-(C—$OR^c$)—, substituted or unsubstituted $C_{0-3}$ alkylene-C(=O)—, substituted or unsubstituted $C_{0-3}$ alkylene-(C(=O)$NR_5$)—, substituted or unsubstituted $C_{0-3}$ alkylene-$N(R_5)$C(=O)—, substituted or unsubstituted $C_{0-3}$ alkylene-O—, substituted or unsubstituted $C_{0-3}$ alkylene-$N(R_5)$—, substituted or unsubstituted $C_{0-3}$ alkylene-S(=O)$_2$—, substituted or unsubstituted $C_{0-3}$ alkylene-S(=O)$_2$$N(R_5)$—, or substituted or unsubstituted $C_{0-3}$ alkylene-$N(R_5)$S(=O)$_2$—. In some embodiments, $L_2$ is substituted or unsubstituted $C_{1-3}$ alkylene, substituted or unsubstituted $C_{0-3}$ alkylene-(C—$OR^c$)—, substituted or unsubstituted $C_{0-3}$ alkylene-C(=O)—, substituted or unsubstituted $C_{0-3}$ alkylene-(C(=O)$NR_5$)—, substituted or unsubstituted $C_{0-3}$ alkylene-$N(R_5)$C(=O)—, substituted or unsubstituted $C_{0-3}$ alkylene-O—, substituted or unsubstituted $C_{0-3}$ alkylene-$N(R_5)$—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, substituted or unsubstituted $C_{0-3}$ alkylene-$N(R_5)$—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, or substituted or unsubstituted $C_{0-3}$ alkylene-$N(R_5)$—. In some embodiments, $L_2$ is substituted or unsubstituted $C_{1-3}$ alkylene or substituted or unsubstituted $C_{0-3}$ alkylene-$N(R_5)$—.
In some embodiments, $L_2$ is substituted or unsubstituted $C_{0-3}$ alkylene-(C—$OR^c$)—, substituted or unsubstituted $C_{0-3}$ alkylene-C(=O)—, substituted or unsubstituted $C_{0-3}$ alkylene-(C(=O)$NR_5$)—, substituted or unsubstituted $C_{0-3}$ alkylene-$N(R_5)$C(=O)—, substituted or unsubstituted $C_{0-3}$ alkylene-O—, substituted or unsubstituted $C_{0-3}$ alkylene-N ($R_5$)—, or substituted or unsubstituted $C_{0-3}$ alkylene-S(=O)$_2$—. In some embodiments, $L_2$ is substituted or unsubstituted $C_{0-3}$ alkylene-(C—OR$^c$)— or substituted or unsubstituted $C_{0-3}$ alkylene-C(=O)—. In some embodiments, $L_2$ is substituted or unsubstituted $C_{0-3}$ alkylene-(C(=O)NR$_5$)—, substituted or unsubstituted $C_{0-3}$ alkylene-N($R_5$)C(=O)—.

In some embodiments of Formula I, Z is O. In another embodiment of Formula I, Z is S. In still another embodiment, X is N. In yet another embodiment, $L_1$ bivalent radical selected from a bond, —($C_{1-4}$ alkylene)-O—, —($C_{1-4}$ alkylene)-N(R$^b$)—, —($C_{1-4}$ alkylene)-S—, or —($C_{1-4}$ alkylene)-S(=O)$_2$—; $R_2$ is H, —OR$^a$, —N(R)$^a$)$_2$, $C_{1-6}$ alkyl, or $C_{1-6}$ alkoxy; and R$^b$ is H or $C_{1-6}$ alkyl. In one embodiment, $R_5$ is not hydrogen. In another embodiment, $R_5$ is —($C_{1-4}$ alkylene)-OR$^d$, —($C_{1-4}$ alkylene)-N(R$^d$)$_2$, —($C_{1-4}$ alkylene)-S(=O)$_2$—(R$^d$), —($C_{1-4}$ alkylene)-($C_{6-14}$ aryl), or —($C_{1-4}$ alkylene)-(5- to 14-membered heteroaryl). In certain embodiments, $R_5$ is —($C_{1-4}$ alkylene)-OR$^d$, —($C_{1-4}$ alkylene)-N(R$^d$)$_2$, or —($C_{1-4}$ alkylene)-S(=O)$_2$—(R$^d$).

In yet another embodiment, $L_3$ is a bivalent radical selected from —($C_{2-6}$ alkenylene)-, —($C_{2-6}$ alkynylene)-, —($C_{3-10}$ heterocycloalkylene)-, —($C_{6-14}$ arylene)-, or -(5- to 14-membered heteroarylene)-. In still another embodiment, $L_3$ is a bond.

In some embodiments, each $R_4$ is H. In other embodiments, $R_4$ is H or optionally substituted alkyl. In certain embodiments, $R_4$ is optionally substituted $C_{1-6}$ alkyl. In some embodiments, each $R_4$ is H or halo$C_{1-6}$alkyl.

In another embodiment of Formula I, $R_5$ is H, $C_{1-6}$ alkyl, —($C_{1-4}$ alkylene)-OR$^d$, —($C_{1-4}$ alkylene)-N(R$^d$)$_2$, —($C_{1-4}$ alkylene)-S(=O)$_2$—(R$^d$), —($C_{1-4}$ alkylene)-($C_{6-14}$ aryl), or —($C_{1-4}$ alkylene)-(5- to 14-membered heteroaryl). In some embodiments, each $R_5$ is H, optionally substituted $C_{1-6}$ alkyl, —($C_{1-4}$ alkylene)-OR$^d$, —($C_{1-4}$ alkylene)-N(R$^d$)$_2$, —($C_{1-4}$ alkylene)-S(=O)$_2$—(R$^d$), —($C_{1-4}$ alkylene)-($C_{6-14}$ aryl), —($C_{1-4}$ alkylene)-(5- to 14-membered heteroaryl), —($C_{1-4}$ alkylene)-C(=O)NR$^b$R$^f$ or —($C_{1-4}$ alkylene)-NR$^b$C(=O)R$^f$. In another embodiment, each $R_5$ is H, $C_{1-6}$ alkyl, —($C_{1-4}$ alkylene)-OR$^d$, —($C_{1-4}$ alkylene)-N(R$^d$)$_2$, —($C_{1-4}$ alkylene)-S(=O)$_2$—(R$^d$), —($C_{1-4}$ alkylene)-($C_{6-14}$ aryl), or —($C_{1-4}$ alkylene)-(5- to 14-membered heteroaryl). In some embodiments, each $R_5$ is H, —($C_{1-4}$ alkylene)-OR$^d$, —($C_{1-4}$ alkylene)-N(R$^d$)$_2$, —($C_{1-4}$ alkylene)-C(=O)NR$^b$R$^f$ or —($C_{1-4}$ alkylene)-NR$^b$C(=O)R$^f$. In some embodiments, each $R_5$ is H, substituted $C_{1-6}$ alkyl, —($C_{1-4}$ alkylene)-OR$^d$, —($C_{1-4}$ alkylene)-N(R$^d$)$_2$, —($C_{1-4}$ alkylene)-C(=O)NR$^b$R$^f$ or —($C_{1-4}$ alkylene)-NR$^b$C(=O)R$^f$. In certain embodiments, each $R_5$ is H, substituted $C_{1-6}$ alkyl, or —($C_{1-4}$ alkylene)-OR$^d$.

In some embodiments, R$^f$ is H, optionally substituted alkyl, optionally substituted heteroalkyl, optionally substituted alkenyl, optionally substituted alkynyl, optionally substituted cycloalkyl, optionally substituted heterocyclyl, or optionally substituted heteroaryl. In some embodiments, R$^f$ is H, alkyl, heteroalkyl, alkenyl, alkynyl, cycloalkyl, heterocyclyl, or heteroaryl. In some embodiments, R$^f$ is H, alkyl, heteroalkyl, cycloalkyl, or heterocyclyl.

In other embodiments of Formula I, the compound has the following structural formula:

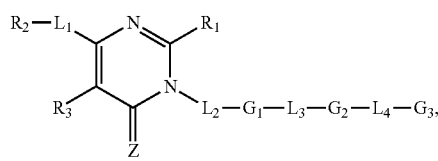

II or a pharmaceutically acceptable salt thereof, wherein:
$R_1$ is H, $C_{1-6}$ alkyl, or $C_{1-6}$ alkoxy;
$R_2$ is H, —OR$^a$, —N(R$^a$)$_2$, $C_{1-6}$ alkyl, or $C_{1-6}$ alkoxy;
$R_3$ is —OH, —NH$_2$, or SH;
Z is O or S;
$L_1$ is a bivalent radical selected from a bond, —C(=O)—, —(C(=O)O)—, —(C(=O)NR$^b$)—, —N(R$^b$)C(=O)—, —($C_{1-4}$ alkylene)-O—, —($C_{1-4}$ alkylene)-N(R$^b$)—, —($C_{1-4}$ alkylene)-S—, or —($C_{1-4}$ alkylene)-S(=O)$_2$—;
$L_2$ is a bivalent radical selected from —(C($R_4$)($R_5$))$_n$—($C_{0-3}$ alkylene)-, —(C($R_4$)($R_5$))$_n$—$C_{0-3}$ alkylene)-(C—OR$^c$)—, —(C($R_4$)($R_5$))$_n$—($C_{0-3}$ alkylene)-C(=O)—, —(C($R_4$)($R_5$))$_n$—($C_{0-3}$ alkylene)-C(=N—OH)—, —(C($R_4$)($R_5$))$_n$—($C_{0-3}$ alkylene)-C(=O)NR$_5$)—, —(C($R_4$)($R_5$))$_n$—($C_{0-3}$ alkylene)-N($R_5$)C(=O)—, —(C($R_4$)($R_5$))$_n$—($C_{0-3}$ alkylene)-O—, —(C($R_4$)($R_5$))$_n$—($C_{0-3}$ alkylene)-N($R_5$)—, —(C($R_4$)($R_5$))$_n$—($C_{0-3}$ alkylene)-S(=O)$_2$—, —(C($R_4$)($R_5$))$_n$—($C_{0-3}$ alkylene)-S(=O)$_2$N($R_5$)—, or —(C($R_4$)($R_5$))$_n$—($C_{0-3}$ alkylene)-N($R_5$)S(=O)$_2$—;

wherein each $R_4$ is H or optionally substituted $C_{1-6}$ alkyl; and
each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —($C_{0-4}$ alkylene)-OR$^f$, —($C_{0-4}$ alkylene)-($C_{1-4}$ alkene), —($C_{0-4}$ alkylene)-($C_{1-4}$ alkyne), $C_2$-$C_7$ heterocycle, —($C_{0-4}$ alkylene)-C(=O)—($C_1$-$C_6$ alkyl), —($C_{0-4}$ alkylene)-C(=O)H, —($C_{0-4}$ alkylene)-C(=O)OR$^f$, —($C_{0-4}$ alkylene)-CN, —($C_{0-4}$ alkylene)-halo, —($C_{0-4}$ alkylene)-NO$_2$, —($C_{0-4}$ alkylene)-N(R$^f$)$_2$, —($C_{0-4}$ alkylene)-S(=O)$_2$—(R$^f$), —($C_{0-4}$ alkylene)-($C_{6-14}$ aryl), —($C_{1-4}$ alkylene)-(5- to 14-membered heteroaryl), —($C_{0-4}$ alkylene)- C(=O)NR$^b$R$^f$ or —($C_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from —($C_{2-6}$ alkenylene)- or —($C_{2-6}$ alkynylene)-;
$L_4$ is a bivalent radical selected from —C(=O)—, —(C(=O)O)—, —(C(=O)NR$^e$)—, —N(R$^e$)C(=O)—, or —($C_{1-4}$ alkylene)-;

$G_1$ and $G_2$ are each independently, at each occurrence, a bivalent radical selected from —($C_{6-14}$ arylene)- or -(5- to 14-membered heteroarylene)-;

$G_3$ is H, $C_{3-7}$ cycloalkyl, $C_{3-10}$ heterocycloalkyl, $C_{6-14}$ aryl, 5- to 14-membered heteroarylene, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

R$^a$, R$^b$, R$^c$, R$^d$, and R$^e$ are each independently, at each occurrence, H or $C_{1-6}$ alkyl; and
n is 1 or 2.

In some embodiments, $L_2$ is substituted or unsubstituted $C_{1-3}$ alkylene, substituted or unsubstituted $C_{0-3}$ alkylene-(C—OR$^e$)-, substituted or unsubstituted $C_{0-3}$ alkylene-C (=O)—, substituted or unsubstituted $C_{0-3}$ alkylene-C(=N—OH)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, substituted or unsubstituted $C_{0-3}$ alkylene-S(=O)$_2$—, substituted or unsubstituted $C_{0-3}$ alkylene-S(=O)$_2$N(R$_5$)—, or substituted or unsubstituted $C_{0-3}$ alkylene-N(R$_5$)S(=O)$_2$—. In some embodiments, L$_2$ is substituted or unsubstituted $C_{1-3}$ alkylene, substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, substituted or unsubstituted $C_{0-3}$ alkylene-S(=O)$_2$—, substituted or unsubstituted $C_{0-3}$ alkylene-S(=O)$_2$N(R$_5$)—, or substituted or unsubstituted $C_{0-3}$ alkylene-N(R$_5$)S(=O)$_2$—. In some embodiments, L$_2$ is substituted or unsubstituted $C_{1-3}$ alkylene, substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, L$_2$ is substituted or unsubstituted $C_{1-3}$ alkylene, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, L$_2$ is substituted or unsubstituted $C_{1-3}$ alkylene, substituted or unsubstituted $C_{0-3}$ alkylene-O—, or substituted or unsubstituted $C_{0-3}$ alkylene-N(R$_5$)—. In some embodiments, L$_2$ is substituted or unsubstituted $C_{1-3}$ alkylene or substituted or unsubstituted $C_{0-3}$ alkylene-N(R$_5$)—. In some embodiments, L$_2$ is substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, L$_2$ is substituted or unsubstituted $C_{0-3}$ alkylene-(C—OR$^c$)— or substituted or unsubstituted $C_{0-3}$ alkylene-C(=O)—. In some embodiments, L$_2$ is substituted or unsubstituted $C_{0-3}$ alkylene-(C(=O)NR$_5$)—, substituted or unsubstituted $C_{0-3}$ alkylene-N(R$_5$)C(=O)—.

In another embodiment of Formula II, L$_3$ is a bivalent radical —(C$_{1-6}$ alkynylene)-. In some embodiments, L$_3$ comprises one or two carbon-carbon triple bonds. In another embodiment of Formula II, R$_1$ is H or C$_{1-6}$ alkyl;
R$_2$ is H, —OR$^a$, C$_{1-6}$ alkyl, or C$_{1-6}$ alkoxy;
R$_3$ is —OH;
Z is O;
L$_1$, is a bivalent radical selected from a bond, —C(=O)—, —(C(=O)O)—, —(C(=O)NR$^b$)—, —N(R$^b$)C(=O)—, —(C$_{1-4}$ alkylene)-N(R$^b$)—, or —(C$_{1-4}$ alkylene)-S(=O)$_2$—;
L$_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-(C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, or —(C(R$_4$)(R$_5$))$_n$—(C$_{0-3}$ alkylene)-N(R$_5$)—;

wherein each R$_4$ is H or C$_{1-6}$ alkyl; and
each R$_5$ is independently H, C$_{1-6}$ alkyl, —(C$_{1-4}$ alkylene)-OR$^f$, —(C$_{1-4}$ alkylene)-N(R$^f$)$_2$, or —(C$_{1-4}$ alkylene)-S(=O)$_2$—(R$^f$);
L$_3$ is a bivalent radical —(C$_{1-6}$ alkynylene)-;
L$_4$ is a bivalent radical selected from —C(=O)—, —(C(=O)O)—, —(C(=O)NR$^e$)—, —N(R$^e$)C(=O)—, or —(C$_{1-4}$ alkylene)-;
G$_1$ and G$_2$ are each independently, at each occurrence, a bivalent radical selected from —(C$_6$ arylene)- or -(5- to 6-membered heteroarylene)-;
G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
R$^a$, R$^b$, R$^c$, R$^d$, and R$^e$ are each independently, at each occurrence, H or C$_{1-6}$ alkyl; and n is 1 or 2.

In yet another embodiment of Formula II, L$_4$ is a bivalent radical selected from —C(=O)— or —(C$_{1-4}$ alkylene)-. In still another embodiment of Formula II, R$_1$ is H or C$_{1-6}$ alkyl;
R$_2$ is H or C$_{1-6}$ alkyl;
R$_3$ is —OH;
Z is O;
L$_1$ is a bivalent radical selected from a bond, —C(=O)—, —(C(=O)O)—, —(C(=O)NR$^b$)—, or —N(R$^b$)C(=O)—;
L$_2$ is a bivalent radical —(C(R$_4$)(R$_5$))$_n$—(C$_{0-3}$ alkylene)-;
wherein each R$_4$ is H or C$_{1-6}$ alkyl; and
each R$_5$ is independently H, or C$_{1-6}$ alkyl;
L$_3$ is a bivalent radical —(C$_{1-6}$ alkynylene)-;
L$_4$ is a bivalent radical selected from —C(=O)— or —(C$_{1-4}$ alkylene)-;
G$_1$ and G$_2$ are each independently, at each occurrence, a bivalent radical selected from —(C$_6$ arylene)- or -(5- to 6-membered heteroarylene)-;
G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
R$^b$ is H or C$_{1-6}$ alkyl; and
n is 1.

In some embodiments, each R$_4$ is H. In other embodiments, R$_4$ is H or optionally substituted alkyl. In certain embodiments, R$_4$ is optionally substituted C$_{1-6}$ alkyl. In some embodiments, each R$_4$ is H or haloC$_{1-6}$alkyl.

In another embodiment of Formula II, R$_5$ is H, C$_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl). In some embodiments, each R$_5$ is H, optionally substituted C$_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), —(C$_{1-4}$ alkylene)-(5- to 14-membered heteroaryl), —(C$_{1-4}$ alkylene)-C(=O)NR$^b$R$^f$ or —(C$_{1-4}$ alkylene)-NR$^b$C(=O)R$^f$. In another embodiment, each R$_5$ is H, C$_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl). In some embodiments, each R$_5$ is H, —(C$_{1-4}$ alkylene)-OR$^d$, —(C$_{1-4}$ alkylene)-N(R$^d$)$_2$, —(C$_{1-4}$ alkylene)-C(=O)NR$^b$R$^f$ or —(C$_{1-4}$ alkylene)-NR$^b$C(=O)R$^f$. In some embodiments, each R$_5$ is H, substituted C$_{1-6}$ alkyl, —(C$_{1-4}$ alkylene)-OR$^d$, —(C$_{1-4}$ alkylene)-N(R$^d$)$_2$, —(C$_{1-4}$ alkylene)- C(=O)NR$^b$R$^f$ or —(C$_{1-4}$ alkylene)-NR$^b$C(=O)R$^f$. In certain embodiments, each R$_5$ is H, substituted C$_{1-6}$ alkyl, or —(C$_{1-4}$ alkylene)-OR$^d$.

In some embodiments, R$^f$ is H, optionally substituted alkyl, optionally substituted heteroalkyl, optionally substituted alkenyl, optionally substituted alkynyl, optionally substituted cycloalkyl, optionally substituted heterocyclyl, or optionally substituted heteroaryl. In some embodiments, R$^f$ is H, alkyl, heteroalkyl, alkenyl, alkynyl, cycloalkyl, heterocyclyl, or heteroaryl. In some embodiments, R$^f$ is H, alkyl, heteroalkyl, cycloalkyl, or heterocyclyl.

In another aspect, a backbone of a compound is not attached to a ring nitrogen atom. In some embodiments, a compound of the disclosure has the following structural formula:

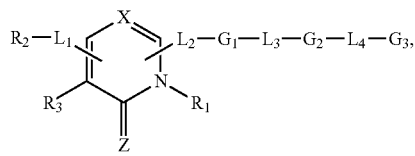

III or a pharmaceutically acceptable salt thereof,
wherein:
R$_1$ is H or C$_{1-6}$ alkyl;
R$_2$ is H, —OR$^a$, —N(R$^a$)$_2$, C$_{1-6}$ alkyl, or C$_{1-6}$ alkoxy;
R$_3$ is H, C$_{1-6}$ alkyl, —OH, —NH$_2$, or SH;
X is CH, S, or N;
Z is O
L$_1$ is a bivalent radical selected from a bond, —C(=O)—, —(C(=O)O)—, —OC(=O)—, —(C(=O)NR$^b$)—, —N(R$^b$)C(=O)—, —N(R$^b$)—, —S(=O)$_2$—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—;
L$_2$ is a bivalent radical selected from —(C(R$_4$)(R$_5$))$_n$—(C$_{0-3}$ alkylene)-, —(C(R$_4$)(R$_5$))$_n$-C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;
wherein each R$_4$ is H or C$_{1-6}$ alkyl; and
each R$_5$ is independently H, an optionally substituted C$_{1-6}$ alkyl, an optionally substituted C$_{1-6}$ heteroalkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$;
wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
L$_3$ is a bivalent radical selected from a bond, —(C$_{1-6}$ alkylene)-, —(C$_{2-6}$ alkenylene)-, —(C$_{2-6}$ alkynylene)-, –(C$_{3-10}$ heterocycloalkylene)-, —(C$_{6-14}$ arylene)-, or -(5- to 14-membered heteroarylene)-;
L$_4$ is a bivalent radical selected from a bond, —C(=O)—, —(C(=O)O)—, —OC(=O)—, —(C(=O)NR$^e$)—, —N(R$^e$)C(=O)—, —N(R$^e$)—, —S(=O)$_2$—, or —(C$_{1-4}$ alkylene)-;
G$_1$ and G$_2$ are each independently, at each occurrence, a bivalent radical selected from —(C$_{6-14}$ arylene)- or -(5- to 14-membered heteroarylene)-;
G$_3$ is H, CN, C$_{1-6}$ alkyl, C$_{3-7}$ cycloalkyl, C$_{3-10}$ heterocycloalkyl, C$_{6-14}$ aryl, 5- to 14-membered heteroarylene, fused 5- to 12-membered heterobicycloalkyl, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), (5- to 14-membered heteroarylene)-(C$_{1-4}$ heteroalkyl), (fused 5- to 12-membered heterobicycloalkyl)-(C$_{1-4}$ heteroalkyl), or (fused 8- to 11-membered heterobiaryl)-(C$_{1-4}$ heteroalkyl); and
R$^a$, R$^b$, R$^c$, R$^d$, and R$^e$ are each independently, at each occurrence, H or C$_{1-6}$ alkyl; and
n is 1 or 2,
provided that R$_1$ or R$_3$ is —OH, —NH$_2$, or SH.

In some embodiments, L$_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-C(=N—OH)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, substituted or unsubstituted C$_{0-3}$ alkylene-S(=O)$_2$—, substituted or unsubstituted C$_{0-3}$ alkylene-S(=O)$_2$N(R$_5$)—, or substituted or unsubstituted C$_{0-3}$ alkylene-N(R$_5$)S(=O)$_2$—. In some embodiments, L$_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, substituted or unsubstituted C$_{0-3}$ alkylene-S(=O)$_2$—, substituted or unsubstituted C$_{0-3}$ alkylene-S(=O)$_2$N(R$_5$)—, or substituted or unsubstituted C$_{0-3}$ alkylene-N(R$_5$)S(=O)$_2$—. In some embodiments, L$_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-(C(=O)NR$_5$)—, substituted or unsubstituted C$_{0-3}$ alkylene-N(R$_5$)C(=O)-, substituted or unsubstituted C$_{0-3}$ alkylene-O-, substituted or unsubstituted C$_{0-3}$ alkylene-N(R$_5$)—, or substituted or unsubstituted C$_{0-3}$ alkylene-S(=O)$_2$—. In some embodiments, L$_2$ is substituted or unsubstituted C$_{1-3}$ alkylene, substituted or unsubstituted C$_{0-3}$ alkylene-O—, substituted or unsubstituted C$_{0-3}$ alkylene-N(R$_5$)—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, or substituted or unsubstituted $C_{0-3}$ alkylene-N(R$_5$)—. In some embodiments, $L_2$ is substituted or unsubstituted $C_{1-3}$ alkylene or substituted or unsubstituted $C_{0-3}$ alkylene-N(R$_5$)—. In some embodiments, $L_2$ is substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, $L_2$ is substituted or unsubstituted $C_{0-3}$ alkylene-(C—OR$^c$)— or substituted or unsubstituted $C_{0-3}$ alkylene-C(=O)—. In some embodiments, $L_2$ is substituted or unsubstituted $C_{0-3}$ alkylene-(C(=O)NR$_5$)—, substituted or unsubstituted $C_{0-3}$ alkylene-N(R$_5$)C(=O)—.

In some embodiments of Formula III, Z is O. In another embodiment of Formula III, Z is S. In still another embodiment, X is N. In yet another embodiment, $L_1$ bivalent radical selected from a bond, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—; $R_2$ is H, —OR$^a$, —N(R$^a$)$_2$, $C_{1-6}$ alkyl, or $C_{1-6}$ alkoxy; and R$^b$ is H or $C_{1-6}$ alkyl. In one embodiment, $R_5$ is not hydrogen. In another embodiment, $R_5$ is —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl). In certain embodiments, $R_5$ is —(C$_{1-4}$ alkylene)-OR$^d$, —(C$_{1-4}$ alkylene)-N(R$^d$)$_2$, or —(C$_{1-4}$ alkylene)-S(=O)$_2$-(R$^d$). In yet another embodiment, $L_3$ is a bivalent radical selected from —(C$_{2-6}$ alkenylene)-, —(C$_{2-6}$ alkynylene)-, —(C$_{3-10}$ heterocycloalkylene)-, —(C$_{6-14}$ arylene)-, or -(5- to 14-membered heteroarylene)-. In still another embodiment, $L_3$ is a bond.

In some embodiments, each $R_4$ is H. In other embodiments, $R_4$ is H or optionally substituted alkyl. In certain embodiments, $R_4$ is optionally substituted $C_{1-6}$ alkyl. In some embodiments, each $R_4$ is H or haloC$_{1-6}$alkyl.

In another embodiment of Formula III, $R_5$ is H, $C_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl). In some embodiments, each $R_5$ is H, optionally substituted $C_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), —(C$_{1-4}$ alkylene)-(5- to 14-membered heteroaryl), —(C$_{1-4}$ alkylene)-C(=O)NR$^b$R$^f$ or —(C$_{1-4}$ alkylene)-NR$^b$C(=O)R$^f$. In another embodiment, each $R_5$ is H, $C_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl). In some embodiments, each $R_5$ is H, —(C$_{1-4}$ alkylene)-OR$^d$, —(C$_{1-4}$ alkylene)-N(R$^d$)$_2$, —(C$_{1-4}$ alkylene)-C(=O)NR$^b$R$^f$ or —(C$_{1-4}$ alkylene)-NR$^b$C(=O)R$^f$. In some embodiments, each $R_5$ is H, substituted $C_{1-6}$ alkyl, —(C$_{1-4}$ alkylene)-OR$^d$, —(C$_{1-4}$ alkylene)-N(R$^d$)$_2$, —(C$_{1-4}$ alkylene)- C(=O)NR$^b$R$^f$ or —(C$_{1-4}$ alkylene)-NR$^b$C(=O)R$^f$. In certain embodiments, each $R_5$ is H, substituted $C_{1-6}$ alkyl, or —(C$_{1-4}$ alkylene)-OR$^d$.

In some embodiments, R$^f$ is H, optionally substituted alkyl, optionally substituted heteroalkyl, optionally substituted alkenyl, optionally substituted alkynyl, optionally substituted cycloalkyl, optionally substituted heterocyclyl, or optionally substituted heteroaryl. In some embodiments, R$^f$ is H, alkyl, heteroalkyl, alkenyl, alkynyl, cycloalkyl, heterocyclyl, or heteroaryl. In some embodiments, R$^f$ is H, alkyl, heteroalkyl, cycloalkyl, or heterocyclyl.

In other embodiments of Formula III, the compound has the following structural formula:

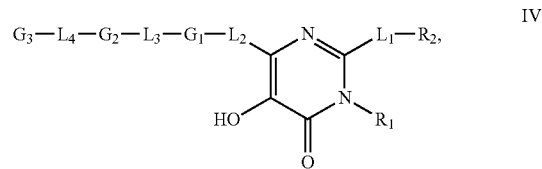

IV or a pharmaceutically acceptable salt thereof,
wherein:
$R_1$ is H or $C_{1-6}$ alkyl;
$R_2$ is H, —OR$^a$, —N(R$^a$)$_2$, $C_{1-6}$ alkyl, or $C_{1-6}$ alkoxy;
$L_1$ a bivalent radical selected from a bond, —C(=O)—, —(C(=O)O)—, -OC(=O)—, —(C(=O)NR$^b$)—, —N(R$^b$)C(=O)—, —N(R$^b$)—, —S(=O)$_2$—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—;
$L_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;
wherein each R$_4$ is H or optionally substituted $C_{1-6}$ alkyl; and
each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —(C$_{0-4}$ alkylene)OR$^f$, —(C$_{0-4}$ alkylene)-(C$_{1-4}$ alkene), —(C$_{0-4}$ alkylene)-(C$_{1-4}$ alkyne), $C_2$-$C_7$ heterocycle, —(C$_{0-4}$ alkylene)-C(=O)—(C$_1$-$C_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$;
wherein R$^f$ is H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;
$L_3$ is a bivalent radical selected from —(C$_{2-6}$ alkenylene)- or —(C$_{2-6}$ alkynylene)-;
$L_4$ is a bivalent radical selected from —C(=O)—, —(C(=O)O)—, —(C(=O)NR$^e$)—, —N(R$^e$)C(=O)—, or —(C$_{1-4}$ alkylene)-;
$G_1$ and $G_2$ are each independently, at each occurrence, a bivalent radical selected from —(C$_{6-14}$ arylene)- or -(5- to 14-membered heteroarylene)-;
$G_3$ is H, $C_{3-7}$ cycloalkyl, $C_{3-10}$ heterocycloalkyl, $C_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-($C_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy; and $R^a$, $R^b$, $R^c$, $R^d$, and $R^e$ are each independently, at each occurrence, H or $C_{1-6}$ alkyl; and n is 1 or 2.

In some embodiments, $L_2$ is substituted or unsubstituted $C_{1-3}$ alkylene, substituted or unsubstituted $C_{0-3}$ alkylene-(C—$OR^c$)—, substituted or unsubstituted $C_{0-3}$ alkylene-C(=O)—, substituted or unsubstituted $C_{0-3}$ alkylene-C(=N—OH)—, substituted or unsubstituted $C_{0-3}$ alkylene-(C(=O)$NR_5$)—, substituted or unsubstituted $C_{0-3}$ alkylene-N($R_5$)C(=O)—, substituted or unsubstituted $C_{0-3}$ alkylene-O—, substituted or unsubstituted $C_{0-3}$ alkylene-N($R_5$)—, substituted or unsubstituted $C_{0-3}$ alkylene-S(=O)$_2$—, substituted or unsubstituted $C_{0-3}$ alkylene-S(=O)$_2$N($R_5$)—, or substituted or unsubstituted $C_{0-3}$ alkylene-N($R_5$)S(=O)$_2$—. In some embodiments, $L_2$ is substituted or unsubstituted $C_{1-3}$ alkylene, substituted or unsubstituted $C_{0-3}$ alkylene-(C—$OR^c$)—, substituted or unsubstituted $C_{0-3}$ alkylene-C(=O)—, substituted or unsubstituted $C_{0-3}$ alkylene-(C(=O)$NR_5$)—, substituted or unsubstituted $C_{0-3}$ alkylene-N($R_5$)C(=O)—, substituted or unsubstituted $C_{0-3}$ alkylene-O—, substituted or unsubstituted $C_{0-3}$ alkylene-N($R_5$)—, substituted or unsubstituted $C_{0-3}$ alkylene-S(=O)$_2$—, substituted or unsubstituted $C_{0-3}$ alkylene-S(=O)$_2$N($R_5$)—, or substituted or unsubstituted $C_{0-3}$ alkylene-N($R_5$)S(=O)$_2$—. In some embodiments, $L_2$ is substituted or unsubstituted $C_{1-3}$ alkylene, substituted or unsubstituted $C_{0-3}$ alkylene-(C—$OR^c$)—, substituted or unsubstituted $C_{0-3}$ alkylene-C(=O)—, substituted or unsubstituted $C_{0-3}$ alkylene-(C(=O)$NR_5$)—, substituted or unsubstituted $C_{0-3}$ alkylene-N($R_5$)C(=O)—, substituted or unsubstituted $C_{0-3}$ alkylene-O—, substituted or unsubstituted $C_{0-3}$ alkylene-N($R_5$)—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, substituted or unsubstituted $C_{0-3}$ alkylene-N($R_5$)—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, or substituted or unsubstituted $C_{0-3}$ alkylene-N($R_5$)—. In some embodiments, $L_2$ is substituted or unsubstituted $C_{1-3}$ alkylene or substituted or unsubstituted $C_{0-3}$ alkylene-N($R_5$)—. In some embodiments, $L_2$ is substituted or unsubstituted $C_{0-3}$ alkylene-(C—$OR^c$)—, substituted or unsubstituted $C_{0-3}$ alkylene-C(=O)—, substituted or unsubstituted $C_{0-3}$ alkylene-(C(=O)$NR_5$)—, substituted or unsubstituted $C_{0-3}$ alkylene-N($R_5$)C(=O)—, substituted or unsubstituted $C_{0-3}$ alkylene-O—, substituted or unsubstituted $C_{0-3}$ alkylene-N($R_5$)—, or substituted or unsubstituted $C_{0-3}$ alkylene-S(=O)$_2$—. In some embodiments, $L_2$ is substituted or unsubstituted $C_{0-3}$ alkylene-(C—$OR^c$)— or substituted or unsubstituted $C_{0-3}$ alkylene-C(=O)—. In some embodiments, $L_2$ is substituted or unsubstituted $C_{0-3}$ alkylene-(C(=O)$NR_5$)—, substituted or unsubstituted $C_{0-3}$ alkylene-N($R_5$)C(=O)—.

In some embodiments of Formula IV, $R_1$ is H or $C_{1-6}$ alkyl;

$R_2$ is H or $C_{1-6}$ alkyl;

$L_1$ is a bivalent radical selected from a bond, —C(=O)O—, —C(=O)$NR^b$—, —N($R^b$)C(=O)—, a bond, —($C_{1-4}$ alkylene)-O—, —($C_{1-4}$ alkylene)-N($R^b$)—, or —($C_{1-4}$ alkylene)-S(=O)$_2$—;

$L_2$ is a bivalent radical is selected from —(C($R_4$)($R_5$))$_n$—($C_{0-3}$ alkylene) or —(C($R_4$)($R_5$))$_n$—($C_{0-3}$ alkylene)-N($R_5$)—;

wherein each $R_4$ is H or $C_{1-6}$ alkyl; and each $R_5$ is independently H or $C_{1-6}$ alkyl, —C(=O)$NR^bR^f$ or —($C_{1-4}$ alkylene)-$NR^bC$(=O)$R^f$;

wherein each $R^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_4$ is a bivalent radical selected from —C(=O)—, —C(=O)O—, —(C(=O)$NR^c$)—, —N($R^c$)C(=O)—, or —($C_{1-4}$ alkylene)-;

$G_1$ and $G_2$ are each independently, at each occurrence, a bivalent radical selected from —($C_{6-14}$ arylene)- or -(5- to 14-membered heteroarylene)-;

$G_3$ is H, $C_{3-7}$ cycloalkyl, $C_{3-10}$ heterocycloalkyl, $C_{6-14}$ aryl, 5- to 14-membered heteroarylene, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy; and $R^b$ and $R^e$ are each independently, at each occurrence, H or $C_{1-6}$ alkyl; and n is 1 or 2.

In some embodiments, $L_1$ is a bond, —($C_{1-4}$ alkylene)-O—, —($C_{1-4}$ alkylene)-N($R^b$)—, —($C_{1-4}$ alkylene)-S—, or —($C_{1-4}$ alkylene)-S(=O)$_2$—; $R_2$ is H, —$OR^a$, —N($R^a$)$_2$, $C_{1-6}$ alkyl, or $C_{1-6}$ alkoxy; and $R^b$ is H or $C_{1-6}$ alkyl. In some embodiments, $L_1$ is a bond, —($C_{1-4}$ alkylene)-O—, —($C_{1-4}$ alkylene)-N($R^b$)—; $R_2$ is H, $C_{1-6}$ alkyl, or $C_{1-6}$ alkoxy; and $R^b$ is H or $C_{1-6}$ alkyl. In some embodiments, $L_1$ is a bond; $R_2$ is H, $C_{1-6}$ alkyl. In some embodiments, $L_1$ is a bond; $R_2$ is H.

In some embodiments, $L_2$ is —(C($R_4$)($R_5$))$_n$—($C_{0-3}$ alkylene)-, —(C($R_4$)($R_5$))$_n$—$C_{0-3}$ alkylene)-(C—$OR^c$)—, —(C($R_4$)($R_5$))$_n$—($C_{0-3}$ alkylene)-O—, or —(C($R_4$)($R_5$))$_n$—($C_{0-3}$ alkylene)-N($R_5$)—. In certain embodiments, $L_2$ is —(C($R_4$)($R_5$))$_n$—($C_{0-3}$ alkylene)-, —(C($R_4$)($R_5$))$_n$—($C_{0-3}$ alkylene)-O—, or —(C($R_4$)($R_5$))$_n$—($C_{0-3}$ alkylene)-N($R_5$)—. In some embodiments, $L_2$ is —(C($R_4$)($R_5$))$_n$—($C_{0-3}$ alkylene)- or —(C($R_4$)($R_5$))$_n$—($C_{0-3}$ alkylene)-N($R_5$)—.

In some embodiments, each $R_4$ is H. In other embodiments, $R_4$ is H or optionally substituted alkyl. In certain embodiments, $R_4$ is optionally substituted $C_{1-6}$ alkyl. In some embodiments, each $R_4$ is H or halo$C_{1-6}$alkyl.

In some embodiments, each $R_5$ is H, optionally substituted $C_{1-6}$ alkyl, —($C_{1-4}$ alkylene)-$OR^d$, —($C_{1-4}$ alkylene)-N($R^d$)$_2$, —($C_{1-4}$ alkylene)-S(=O)$_2$—($R^d$), —($C_{1-4}$ alkylene)-($C_{6-14}$ aryl), —($C_{1-4}$ alkylene)-(5- to 14-membered heteroaryl), —($C_{1-4}$ alkylene)- C(=O)$NR^bR^f$ or —($C_{1-4}$ alkylene)-$NR^bC$(=O)$R^f$. In another embodiment, each $R_5$ is H, $C_{1-6}$ alkyl, —($C_{1-4}$ alkylene)-$OR^d$, —($C_{1-4}$ alkylene)-N($R^d$)$_2$, —($C_{1-4}$ alkylene)-S(=O)$_2$—($R^d$), —($C_{1-4}$ alkylene)-($C_{6-14}$ aryl), or —($C_{1-4}$ alkylene)-(5- to 14-membered heteroaryl). In some embodiments, each $R_5$ is H, —($C_{1-4}$ alkylene)-$OR^d$, —($C_{1-4}$ alkylene)-N($R^d$)$_2$, —($C_{1-4}$ alkylene)-C(=O)$NR^bR^f$ or —($C_{1-4}$ alkylene)-$NR^bC$(=O)$R^f$. In some embodiments, each $R_5$ is H, substituted $C_{1-6}$ alkyl, —($C_{1-4}$ alkylene)-$OR^d$, —($C_{1-4}$ alkylene)-N($R^d$)$_2$, —($C_{1-4}$ alkylene)-C(=O)NR$^b$R$^f$ or —(C$_{1-4}$ alkylene)-NR$^b$C(=O)R$^f$. In certain embodiments, each R$_5$ is H, substituted C$_{1-6}$ alkyl, or —(C$_{1-4}$ alkylene)-OR$^d$.

In some embodiments, R$^f$ is H, optionally substituted alkyl, optionally substituted heteroalkyl, optionally substituted alkenyl, optionally substituted alkynyl, optionally substituted cycloalkyl, optionally substituted heterocyclyl, or optionally substituted heteroaryl. In some embodiments, R$^f$ is H, alkyl, heteroalkyl, alkenyl, alkynyl, cycloalkyl, heterocyclyl, or heteroaryl. In some embodiments, R$^f$ is H, alkyl, heteroalkyl, cycloalkyl, or heterocyclyl.

In some embodiments, each R$_5$ is —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), —(C$_{1-4}$ alkylene)-(5- to 14-membered heteroaryl), —C(=O)NR$^b$R$^f$ or —(C$_{1-4}$ alkylene)-NR$^b$C(=O)R$^f$; wherein R$^f$ is H, an optionally substituted alkyl, an optionally substituted heteroalkyl, an optionally substituted cycloalkyl or an optionally substituted heterocyclyl.

In some embodiments, L$_4$ is —C(=O)—. In some embodiments, L$_4$ is —(C(=O)O)—. In some embodiments, L$_4$ is —(C(=O)NR$^e$)—. In some embodiments, L$_4$ is —N(R$^e$)C(=O)— In some embodiments, L$_4$ is —(C$_{1-4}$ alkylene)-.

In some embodiments, G$_1$ and G$_2$ are —(C$_{6-14}$ arylene)-. In other embodiments, G$_1$ and G$_2$ are -(5- to 14-membered heteroarylene)-.

In some embodiments, G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkynyl, an optionally substituted cycloalkyl, an optionally substituted heterocyclyl, or an optionally substituted alkoxy. In some embodiments, G$_3$ is C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, or an optionally substituted heteroalkyl. In some embodiments, G$_3$ is C$_{3-7}$ cycloalkyl, C$_{3-10}$ heterocycloalkyl, (C$_{1-4}$ alkylene)-(C$_{1-4}$ heteroalkyl), (C$_{3-10}$ heterocycloalkylene)-(C$_{1-4}$ alkyl), or (C$_{3-10}$ heterocycloalkylene)-(C$_{1-4}$ heteroalkyl). In some embodiments, G$_3$ is C$_{3-7}$ cycloalkyl. In some embodiments, G$_3$ is C$_{3-10}$ heterocycloalkyl. In some embodiments, G$_3$ is (C$_{1-4}$ alkylene)-(C$_{1-4}$ heteroalkyl). In some embodiments, G$_3$ is (C$_{3-10}$ heterocycloalkylene)-(C$_{1-4}$ alkyl). In some embodiments, G$_3$ is (C$_{3-10}$ heterocycloalkylene)-(C$_{1-4}$ heteroalkyl).

In another embodiment, a compound of the disclosure has the following structural formula:

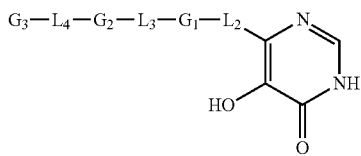

IVA or a pharmaceutically acceptable salt thereof, wherein;

L$_2$ is —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, or —(C(R$_4$)(R$_5$))$_n$—(C$_{0-3}$ alkylene)-S(=O)$_2$—;

wherein each R$_4$ is H or optionally substituted C$_{1-6}$ alkyl; and each R$_5$ is independently H, an optionally substituted C$_{1-6}$ alkyl, an optionally substituted C$_{1-6}$ heteroalkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)-C(=O)NR$^b$R$^f$ or —(C$_{0-4}$ alkylene)-NR$^b$C(=O)R$^f$;

wherein each R$^f$ is independently H, an optionally substituted alkyl, an optionally substituted cycloalkyl, an optionally substituted heterocyclyl, or an optionally substituted alkoxy;

L$_3$ is —(C$_{2-6}$ alkynylene)-;

L$_4$ is —C(=O)—, —(C(=O)O)—, —(C(=O)NR$^e$)—, —N(R$^e$)C(=O)—, or —(C$_{1-4}$ alkylene)-;

G$_1$ and G$_2$ are each independently, at each occurrence, —(C$_{6-14}$ arylene)-;

G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, or an optionally substituted alkoxy; and R$^a$, R$^b$, R$^c$, R$^d$, and R$^e$ are each independently, at each occurrence, H or C$_{1-6}$ alkyl; and n is 1 or 2.

In some embodiments, L$_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-C(=N—OH)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, substituted or unsubstituted C$_{0-3}$ alkylene-S(=O)$_2$—, substituted or unsubstituted C$_{0-3}$ alkylene-S(=O)$_2$N(R$_5$)—, or substituted or unsubstituted C$_{0-3}$ alkylene-N(R$_5$)S(=O)$_2$—. In some embodiments, L$_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, substituted or unsubstituted C$_{0-3}$ alkylene-S(=O)$_2$—, substituted or unsubstituted C$_{0-3}$ alkylene-S(=O)$_2$N(R$_5$)—, or substituted or unsubstituted C$_{0-3}$ alkylene-N(R$_5$)S(=O)$_2$—. In some embodiments, L$_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-(C(=O)

NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, or substituted or unsubstituted C$_{0-3}$ alkylene-S(=O)$_2$—. In some embodiments, L$_2$ is substituted or unsubstituted C$_{1-3}$ alkylene, substituted or unsubstituted C$_{0-3}$ alkylene-O—, substituted or unsubstituted C$_{0-3}$ alkylene-N(R$_5$)—, or substituted or unsubstituted C$_{0-3}$ alkylene-S(=O)$_2$—. In some embodiments, L$_2$ is substituted or unsubstituted C$_{1-3}$ alkylene, substituted or unsubstituted C$_{0-3}$ alkylene-O—, or substituted or unsubstituted C$_{0-3}$ alkylene-N(R$_5$)—. In some embodiments, L$_2$ is substituted or unsubstituted C$_{1-3}$ alkylene or substituted or unsubstituted C$_{0-3}$ alkylene-N(R$_5$)—. In some embodiments, L$_2$ is substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, or substituted or unsubstituted C$_{0-3}$ alkylene-S(=O)$_2$—. In some embodiments, L$_2$ is substituted or unsubstituted C$_{0-3}$ alkylene-(C—OR$^c$)- or substituted or unsubstituted C$_{0-3}$ alkylene-C(=O)—. In some embodiments, L$_2$ is substituted or unsubstituted C$_{0-3}$ alkylene-(C(=O)NR$_5$)—, substituted or unsubstituted C$_{0-3}$ alkylene-N(R$_5$)C(=O)—.

Some embodiments provided herein describe a compound of Formula IVA, wherein

L$_2$ is —(C(R$_4$)(R$_5$))$_n$—(C$_{0-3}$ alkylene)-, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—;

wherein each R$_4$ is H or optionally substituted C$_{1-6}$ alkyl; and each R$_5$ is independently H, an optionally substituted C$_{1-6}$ alkyl, an optionally substituted C$_{1-6}$ heteroalkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{1-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_{1-6}$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$;

wherein each R$^f$ is independently H, an optionally substituted alkyl, an optionally substituted cycloalkyl, an optionally substituted heterocyclyl, or an optionally substituted alkoxy;

L$_3$ is —(C$_{2-6}$ alkynylene)-;

L$_4$ is —C(=O)—, —(C(=O)O)—, —(C(=O)NR$^c$)—, or —(C$_{1-4}$ alkylene)-;

G$_1$ and G$_2$ are each independently, at each occurrence, —(C$_{6-14}$ arylene)-;

G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{1-4}$ alkylene)-(C$_{1-4}$ heterocycloalkyl), (C$_{3-10}$ heterocycloalkylene)-(C$_{1-4}$ alkyl), (C$_{3-10}$ heterocycloalkylene)-(C$_{1-4}$ heteroalkyl), (C$_{3-10}$ heterocycloalkylene)-(C$_{3-10}$ heterocycloalkyl), C$_{1-6}$ alkyl, or (C$_{3-10}$ heterocycloalkylene)-hydroxy; and R$^a$, R$^b$, R$^c$, R$^d$, and R$^e$ are each independently, at each occurrence, H or C$_{1-6}$ alkyl; and n is 1 or 2.

In some embodiments, L$_2$ is —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-O—, or —(C(R$_4$)(R$_5$))$_n$—(C$_{0-3}$ alkylene)-N(R$_5$)—.

In certain embodiments, L$_2$ is —(C(R$_4$)(R$_5$))$_n$(C$_{0-3}$ alkylene)-, —(C(R$_4$)(R$_5$))$_n$—(C$_{0-3}$ alkylene)-O—, or —(C(R$_4$)(R$_5$))$_n$—(C$_{0-3}$ alkylene)-N(R$_5$)—. In some embodiments, L$_2$ is —(C(R$_4$)(R$_5$))$_n$(C$_{0-3}$ alkylene)- or —(C(R$_4$)(R$_5$))$_n$—(C$_{0-3}$ alkylene)-N(R$_5$)—.

In some embodiments, each R$_4$ is H. In other embodiments, R$_4$ is H or optionally substituted alkyl. In certain embodiments, R$_4$ is optionally substituted C$_{1-6}$ alkyl. In some embodiments, each R$_4$ is H or haloC$_{1-6}$alkyl.

In some embodiments, each R$_5$ is H, optionally substituted C$_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), —(C$_{1-4}$ alkylene)-(5- to 14-membered heteroaryl), —(C$_{1-4}$ alkylene)- C(=O)NR$^b$R$^f$ or —(C$_{1-4}$ alkylene)-NR$^b$C(=O)R$^f$. In another embodiment, each R$_5$ is H, C$_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), or —(C$_{1-4}$ alkylene)-(5- to 14-membered heteroaryl). In some embodiments, each R$_5$ is H, —(C$_{1-4}$ alkylene)-OR$^d$, —(C$_{1-4}$ alkylene)-N(R$^d$)$_2$, —(C$_{1-4}$ alkylene)-C(=O)NR$^b$R$^f$ or —(C$_{1-4}$ alkylene)-NR$^b$C(=O)R$^f$. In some embodiments, each R$_5$ is H, substituted C$_{1-6}$ alkyl, —(C$_{1-4}$ alkylene)-OR$^d$, (C$_{1-4}$ alkylene)-N(R$^d$)$_2$, —(C$_{1-4}$ alkylene)- C(=O)NR$^b$R$^f$ or —(C$_{1-4}$ alkylene)-NR$^b$C(=O) R$^f$. In certain embodiments, each R$_5$ is H, substituted C$_{1-6}$ alkyl, or —(C$_{1-4}$ alkylene)-OR$^d$.

In some embodiments, R$^f$ is H, optionally substituted alkyl, optionally substituted heteroalkyl, optionally substituted alkenyl, optionally substituted alkynyl, optionally substituted cycloalkyl, optionally substituted heterocyclyl, or optionally substituted heteroaryl. In some embodiments, R$^f$ is H, alkyl, heteroalkyl, alkenyl, alkynyl, cycloalkyl, heterocyclyl, or heteroaryl. In some embodiments, R$^f$ is H, alkyl, heteroalkyl, cycloalkyl, or heterocyclyl.

In some embodiments, each R$_5$ is —(C$_{1-4}$ alkylene)-OR$^d$, —(C$_{1-4}$ alkylene)-N(R$^d$)$_2$, —(C$_{1-4}$ alkylene)-S(=O)$_2$—(R$^d$), —(C$_{1-4}$ alkylene)-(C$_{6-14}$ aryl), —(C$_{1-4}$ alkylene)-(5- to 14-membered heteroaryl), —C(=O)NR$^b$R$^f$ or —(C$_{1-4}$ alkylene)-NR$^b$C(=O)R$^f$; wherein R$^f$ is H, an optionally substituted alkyl, an optionally substituted heteroalkyl, an optionally substituted cycloalkyl or an optionally substituted heterocyclyl.

In some embodiments, L$_4$ is —C(=O)—. In some embodiments, L$_4$ is —(C(=O)O)—. In some embodiments, L$_4$ is —(C(=O)NR$^e$)—. In some embodiments, L$_4$ is —N(R$^e$)C(=O)— In some embodiments, L$_4$ is —(C$_{1-4}$ alkylene)-.

In some embodiments, G$_1$ and G$_2$ are —(C$_{6-14}$ arylene)-. In other embodiments, G$_1$ and G$_2$ are -(5- to 14-membered heteroarylene)-.

In some embodiments, G$_3$ is H, C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkynyl, an optionally substituted cycloalkyl, an optionally substituted heterocyclyl, or an optionally substituted alkoxy. In some embodiments, G$_3$ is C$_{3-7}$ cycloalkyl, C$_{3-10}$ heterocycloalkyl, C$_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl,or an optionally substituted heteroalkyl. In some embodiments, $G_3$ is $C_{3-7}$ cycloalkyl, $C_{3-10}$ heterocycloalkyl, $(C_{1-4}$ alkylene)-$(C_{1-4}$ heteroalkyl), $(C_{3-10}$ heterocycloalkylene)-$(C_{1-4}$ alkyl), or $(C_{3-10}$ heterocycloalkylene)-$(C_{1-4}$ heteroalkyl). In some embodiments, $G_3$ is $C_{3-7}$ cycloalkyl. In some embodiments, $G_3$ is $C_{3-10}$ heterocycloalkyl. In some embodiments, $G_3$ is $(C_{1-4}$ alkylene)-$(C_{1-4}$ heteroalkyl). In some embodiments, $G_3$ is $(C_{3-10}$ heterocycloalkylene)-$(C_{1-4}$ alkyl). In some embodiments, $G_3$ is $(C_{3-10}$ heterocycloalkylene)-$(C_{1-4}$ heteroalkyl).

In some embodiments, $G_3$ is H, $C_{3-10}$ heterocycloalkyl, $(C_{1-4}$ alkylene)-$(C_{1-4}$ heteroalkyl), $(C_{1-4}$ alkylene)-$(C_{1-4}$ heterocycloalkyl), $(C_{3-10}$ heterocycloalkylene)-$(C_{1-4}$ heteroalkyl), $(C_{3-10}$ heterocycloalkylene)-$(C_{3-10}$ heterocycloalkyl), $C_{1-6}$ alkyl, $(C_{3-10}$ heterocycloalkylene)-hydroxy, or tetrazolyl.

In another embodiment, a compound of the disclosure has the following structural formula:

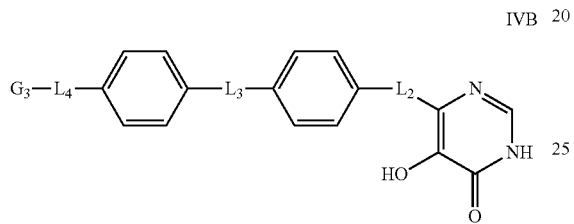

IVB or a pharmaceutically acceptable salt thereof, wherein;
$L_2$ is a bivalent radical selected from —$(C(R_4)(R_5))_n$—$(C_{0-3}$ alkylene)-, —$(C(R_4)(R_5))_n$—$C_{0-3}$ alkylene)-$(C$—$OR^c)$—, —$(C(R_4)(R_5))_n$—$(C_{0-3}$ alkylene)-$C(=O)$—, —$(C(R_4)(R_5))_n$—$(C_{0-3}$ alkylene)-$O$—, —$(C(R_4)(R_5))_n$—$(C_{0-3}$ alkylene)-$N(R_5)$—, —$(C(R_4)(R_5))_n$—$(C_{0-3}$ alkylene)-$S(=O)_2$—;
wherein each $R_4$ is H or optionally substituted $C_{1-6}$ alkyl; and
each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene)-$OR^f$, —$(C_{0-4}$ alkylene)-$(C_{1-4}$ alkene), —$(C_{0-4}$ alkylene)-$(C_{1-4}$ alkyne), $C_2$-$C_7$ heterocycle, —$(C_{0-4}$ alkylene)-$C(=O)$—$(C_1$-$C_6$ alkyl), —$(C_{0-4}$ alkylene)-$C(=O)H$, —$(C_{0-4}$ alkylene)-$C(=O)OR^f$, —$(C_{0-4}$ alkylene)-$CN$, —$(C_{0-4}$ alkylene)-halo, —$(C_{0-4}$ alkylene)-$NO_2$, —$(C_{0-4}$ alkylene)-$N(R^f)_2$, —$(C_{0-4}$ alkylene)-$S(=O)_2$—$(R^f)$, —$(C_{0-4}$ alkylene)-$(C_{6-14}$ aryl), —$(C_{1-4}$ alkylene)-(5- to 14-membered heteroaryl), —$(C_{0-4}$ alkylene)- $C(=O)NR^bR^f$ or —$(C_{0-4}$ alkylene)-$NR^bC(=O)R^f$;
wherein each $R^f$ is independently H, an optionally substituted alkyl, an optionally substituted cycloalkyl, an optionally substituted heterocyclyl, or an optionally substituted alkoxy;
$L_3$ is —$(C_{2-6}$ alkynylene)-;
$L_4$ is a bivalent radical selected from —$C(=O)$—, —$(C(=O)O)$—, —$(C(=O)NR^e)$—, —$N(R^e)C(=O)$—, or —$(C_{1-4}$ alkylene)-;
$G_3$ is H, $C_{3-7}$ cycloalkyl, $C_{3-10}$ heterocycloalkyl, $C_{6-14}$ aryl, 5- to 14-membered heteroarylene, $(C_{1-4}$ alkylene)-$(C_{1-4}$ heteroalkyl), $(C_{1-4}$ alkylene)-$(C_{1-4}$ heterocycloalkyl), $(C_{3-10}$ heterocycloalkylene)-$(C_{1-4}$ alkyl), $(C_{3-10}$ heterocycloalkylene)-$(C_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, or an optionally substituted alkoxy; and
$R^a$, $R^b$, $R^c$, $R^d$, and $R^e$ are each independently, at each occurrence, H or $C_{1-6}$ alkyl; and
n is 1 or 2.

Some embodiments provided herein describe a compound of Formula IVB, $L_2$ is —$(C(R_4)(R_5))_n$—$(C_{0-3}$ alkylene)-, —$(C(R_4)(R_5))_n$—$(C_{0-3}$ alkylene)-$N(R_5)$—, —$(C(R_4)(R_5))_n$—$(C_{0-3}$ alkylene)-$S(=O)_2$—;
wherein each $R_4$ is H or optionally substituted $C_{1-6}$ alkyl; and
each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene)-$OR^f$, —$(C_{0-4}$ alkylene)-$(C_{1-4}$ alkene), —$(C_{0-4}$ alkylene)-$(C_{1-4}$ alkyne), $C_2$-$C_7$ heterocycle, —$(C_{0-4}$ alkylene)-$C(=O)$—$(C_1$-$C_6$ alkyl), —$(C_{0-4}$ alkylene)-$C(=O)H$, —$(C_{0-4}$ alkylene)-$C(=O)OR^f$, —$(C_{0-4}$ alkylene)-$CN$, —$(C_{0-4}$ alkylene)-halo, —$(C_{0-4}$ alkylene)-$NO_2$, —$(C_{0-4}$ alkylene)-$N(R^f)_2$, —$(C_{0-4}$ alkylene)-$S(=O)_2$—$(R^f)$, —$(C_{0-4}$ alkylene)-$(C_{6-14}$ aryl), —$(C_{1-4}$ alkylene)-(5- to 14-membered heteroaryl), —$(C_{0-4}$ alkylene)- $C(=O)NR^bR^f$ or —$(C_{0-4}$ alkylene)-$NR^bC(=O)R^f$;
wherein each $R^f$ is independently H, an optionally substituted alkyl, an optionally substituted cycloalkyl, an optionally substituted heterocyclyl, or an optionally substituted alkoxy;
$L_3$ is —$(C_{2-4}$ alkynylene)-;
$L_4$ is —$C(=O)$—, —$(C(=O)O)$—, —$(C(=O)NR^e)$—, or —$(C_{1-4}$ alkylene)-;
$G_3$ is H, $C_{3-7}$ cycloalkyl, $C_{3-10}$ heterocycloalkyl, $C_{6-14}$ aryl, 5- to 14-membered heteroarylene, $(C_{1-4}$ alkylene)-$(C_{1-4}$ heteroalkyl), $(C_{1-4}$ alkylene)-$(C_{1-4}$ heterocycloalkyl), $(C_{3-10}$ heterocycloalkylene)-$(C_{1-4}$ alkyl), $(C_{3-10}$ heterocycloalkylene)-$(C_{1-4}$ heteroalkyl), $(C_{3-10}$ heterocycloalkylene)-$(C_{3-10}$ heterocycloalkyl), $C_{1-6}$ alkyl, or $(C_{3-10}$ heterocycloalkylene)-hydroxy; and
$R^a$, $R^b$, $R^c$, $R^d$, and $R^e$ are each independently, at each occurrence, H or $C_{1-6}$ alkyl; and
n is 1 or 2.

In some embodiments, $L_2$ is substituted or unsubstituted $C_{1-3}$ alkylene, substituted or unsubstituted $C_{0-3}$ alkylene-$(C$—$OR^c)$—, substituted or unsubstituted $C_{0-3}$ alkylene-$C(=O)$—, substituted or unsubstituted $C_{0-3}$ alkylene-$C(=N$—$OH)$—, substituted or unsubstituted $C_{0-3}$ alkylene-$(C(=O)NR_5)$—, substituted or unsubstituted $C_{0-3}$ alkylene-$N(R_5)C(=O)$—, substituted or unsubstituted $C_{0-3}$ alkylene-$O$—, substituted or unsubstituted $C_{0-3}$ alkylene-$N(R_5)$—, substituted or unsubstituted $C_{0-3}$ alkylene-$S(=O)_2$—, substituted or unsubstituted $C_{0-3}$ alkylene-$S(=O)_2N(R_5)$—, or substituted or unsubstituted $C_{0-3}$ alkylene-$N(R_5)S(=O)_2$—. In some embodiments, $L_2$ is substituted or unsubstituted $C_{1-3}$ alkylene, substituted or unsubstituted $C_{0-3}$ alkylene-$(C$—$OR^c)$—, substituted or unsubstituted $C_{0-3}$ alkylene-$C(=O)$—, substituted or unsubstituted $C_{0-3}$ alkylene-$(C(=O)NR_5)$—, substituted or unsubstituted $C_{0-3}$ alkylene-$N(R_5)C(=O)$—, substituted or unsubstituted $C_{0-3}$ alkylene-$O$—, substituted or unsubstituted $C_{0-3}$ alkylene-$N(R_5)$—, substituted or unsubstituted $C_{0-3}$ alkylene-$S(=O)_2$—, substituted or unsubstituted $C_{0-3}$ alkylene-$S(=O)_2N(R_5)$—, or substituted or unsubstituted $C_{0-3}$ alkylene-$N(R_5)S(=O)_2$—. In some embodiments, $L_2$ is substituted or unsubstituted $C_{1-3}$ alkylene, substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, or substituted or unsubstituted $C_{0-3}$ alkylene-N(R$_5$)—. In some embodiments, $L_2$ is substituted or unsubstituted $C_{1-3}$ alkylene or substituted or unsubstituted $C_{0-3}$ alkylene-N(R$_5$)—. In some embodiments, $L_2$ is substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, $L_2$ is substituted or unsubstituted $C_{0-3}$ alkylene-(C—OR$^c$)— or substituted or unsubstituted $C_{0-3}$ alkylene-C(=O)—. In some embodiments, $L_2$ is substituted or unsubstituted $C_{0-3}$ alkylene-(C(=O)NR$_5$)—, substituted or unsubstituted $C_{0-3}$ alkylene-N(R$_5$)C(=O)—.

In some embodiments, $L_2$ is —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-O—, or —(C(R$_4$)(R$_5$))$_n$—(C$_{0-3}$ alkylene)-N(R$_5$)—. In certain embodiments, $L_2$ is —(C(R$_4$)(R$_5$))$_n$—(C$_{0-3}$ alkylene)-, —(C(R$_4$)(R$_5$))$_n$—(C$_{0-3}$ alkylene)-O—, or —(C(R$_4$)(R$_5$))$_n$—(C$_{0-3}$ alkylene)-N(R$_5$)—. In some embodiments, $L_2$ is —(C(R$_4$)(R$_5$))$_n$—(C$_{0-3}$ alkylene)- or —(C(R$_4$)(R$_5$))$_n$—(C$_{0-3}$ alkylene)-N(R$_5$)—.

In some embodiments, each $R_4$ is H. In other embodiments, $R_4$ is H or optionally substituted alkyl. In certain embodiments, $R_4$ is optionally substituted $C_{1-6}$ alkyl. In some embodiments, each $R_4$ is H or haloC$_{1-6}$alkyl.

In some embodiments, each $R_5$ is H, optionally substituted $C_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$-(R$^d$), —(C$_{1-4}$ alkylene)-(C$_{6-14}$ aryl), —(C$_{1-4}$ alkylene)-(5- to 14-membered heteroaryl), —(C$_{1-4}$ alkylene)- C(=O)NR$^b$R$^f$ or —(C$_{1-4}$ alkylene)-NR$^b$C(=O)R$^f$. In another embodiment, each $R_5$ is H, C$_{1-6}$ alkyl, —(C$_{1-4}$ alkylene)-OR$^d$, —(C$_{1-4}$ alkylene)-N(R$^d$)$_2$, —(C$_{1-4}$ alkylene)-S(=O)$_2$-(R$^d$), —(C$_{1-4}$ alkylene)-(C$_{6-14}$ aryl), or —(C$_{1-4}$ alkylene)-(5- to 14-membered heteroaryl). In some embodiments, each $R_5$ is H, —(C$_{1-4}$ alkylene)-OR$^d$, —(C$_{1-4}$ alkylene)-N(R$^d$)$_2$, —(C$_{1-4}$ alkylene)-C(=O)NR$^b$R$^f$ or —(C$_{1-4}$ alkylene)-NR$^b$C(=O)R$^f$. In some embodiments, each $R_5$ is H, substituted $C_{1-6}$ alkyl, —(C$_{1-4}$ alkylene)-OR$^d$, —(C$_{1-4}$ alkylene)-N(R$_d$)$_2$, —(C$_{1-4}$ alkylene)-C(=O)NR$^b$R$^f$ or —(C$_{1-4}$ alkylene)-NR$^b$C(=O)R$^f$. In certain embodiments, each $R_5$ is H, substituted $C_{1-6}$ alkyl, or —(C$_{1-4}$ alkylene)-OR$^d$.

In some embodiments, R$^f$ is H, optionally substituted alkyl, optionally substituted heteroalkyl, optionally substituted alkenyl, optionally substituted alkynyl, optionally substituted cycloalkyl, optionally substituted heterocyclyl, or optionally substituted heteroaryl. In some embodiments, R$^f$ is H, alkyl, heteroalkyl, alkenyl, alkynyl, cycloalkyl, heterocyclyl, or heteroaryl. In some embodiments, R$^f$ is H, alkyl, heteroalkyl, cycloalkyl, or heterocyclyl.

In some embodiments, each $R_5$ is —(C$_{1-4}$ alkylene)-OR$^d$, —(C$_{1-4}$ alkylene)-N(R$^d$)$_2$, —(C$_{1-4}$ alkylene)-S(=O)$_2$-(R$^d$), —(C$_{1-4}$ alkylene)-(C$_{6-14}$ aryl), —(C$_{1-4}$ alkylene)-(5- to 14-membered heteroaryl), =C(=O)NR$^b$R$^f$ or —(C$_{1-4}$ alkylene)-NR$^b$C(=O)R$^f$; wherein R$^f$ is H, an optionally substituted alkyl, an optionally substituted heteroalkyl, an optionally substituted cycloalkyl or an optionally substituted heterocyclyl.

In some embodiments, $L_3$ is —(C$_2$-alkynylene)-. In other embodiments, $L_3$ is —(C$_4$-alkynylene)-.

In some embodiments, $L_4$ is —C(=O)—. In some embodiments, $L_4$ is —(C(=O)O)—. In some embodiments, $L_4$ is —(C(=O)NR$^e$)—. In some embodiments, $L_4$ is —N(R$^e$)C(=O)— In some embodiments, $L_4$ is —(C$_{1-4}$ alkylene)-.

In some embodiments, $G_3$ is H, $C_{3-7}$ cycloalkyl, $C_{3-10}$ heterocycloalkyl, $C_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkynyl, an optionally substituted cycloalkyl, an optionally substituted heterocyclyl, or an optionally substituted alkoxy. In some embodiments, $G_3$ is $C_{3-7}$ cycloalkyl, $C_{3-10}$ heterocycloalkyl, $C_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl,or an optionally substituted heteroalkyl. In some embodiments, $G_3$ is $C_{3-7}$ cycloalkyl, $C_{3-10}$ heterocycloalkyl, (C$_{1-4}$ alkylene)-(C$_{1-4}$ heteroalkyl), (C$_{3-10}$ heterocycloalkylene)-(C$_{1-4}$ alkyl), or (C$_{3-10}$ heterocycloalkylene)-(C$_{1-4}$ heteroalkyl). In some embodiments, $G_3$ is $C_{3-7}$ cycloalkyl. In some embodiments, $G_3$ is $C_{3-10}$ heterocycloalkyl. In some embodiments, $G_3$ is (C$_{1-4}$ alkylene)-(C$_{1-4}$ heteroalkyl). In some embodiments, $G_3$ is (C$_{3-10}$ heterocycloalkylene)-(C$_{1-4}$ alkyl). In some embodiments, $G_3$ is (C$_{3-10}$ heterocycloalkylene)-(C$_{1-4}$ heteroalkyl).

In some embodiments, $G_3$ is H, $C_{3-10}$ heterocycloalkyl, (C$_{1-4}$ alkylene)-(C$_{1-4}$ heteroalkyl), (C$_{1-4}$ alkylene)-(C$_{1-4}$ heterocycloalkyl), (C$_{3-10}$ heterocycloalkylene)-(C$_{1-4}$ heteroalkyl), (C$_{3-10}$ heterocycloalkylene)-(C$_{3-10}$ heterocycloalkyl), $C_{1-6}$ alkyl, (C$_{3-10}$ heterocycloalkylene)-hydroxy, or tetrazolyl.

In some embodiments, n is 1. In other embodiments, n is 2.

In still another aspect, the disclosure provides a compound of Formula V:

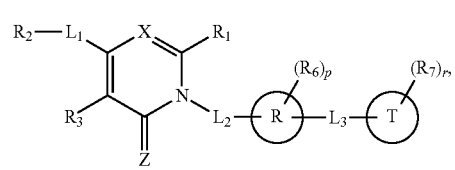

or a pharmaceutically acceptable salt thereof,
  wherein:
  $R_1$ is H, —OH, —NH$_2$, or SH;
  $R_2$ is H, —OR$^a$, —N(R$^a$)$_2$, $C_{1-6}$ alkyl, or $C_{1-6}$ alkoxy;
  $R_3$ is H, —OH, —NH$_2$, or SH;
  $R_6$ and $R_7$ are each independently, at each occurrence, —OH, —NH$_2$, —CN, —NO$_2$, —C(=O)OR$^b$, —C(=O)N(R$^b$)$_2$, —N(R$^b$)C(=O)OR$^b$, halo, $C_{1-6}$ alkyl, $C_{1-6}$ alkoxy, =O, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

ring R is $C_{3-7}$ cycloalkyl, $C_{3-10}$ heterocycloalkyl, $C_{6-14}$ aryl, or a 5- to 14-membered heteroaryl;

ring T is $C_{3-7}$ cycloalkyl, $C_{3-10}$ heterocycloalkyl, $C_{6-14}$ aryl, or a 5- to 14-membered heteroaryl;

X is CH, S, or N;

Z is O or S;

$L_1$ is a bivalent radical selected from a bond, —C(=O)—, —(C(=O)O)—, —OC(=O)—, —(C(=O)NR$^c$)—, —N(R$^c$)C(=O)—, —N(R$^c$)—, —S(=O)$_2$—, —($C_{1-4}$ alkylene)-, —($C_{1-4}$ alkylene)-O—, —($C_{1-4}$ alkylene)-N(R$^c$)—, —($C_{1-4}$ alkylene)-S—, or —($C_{1-4}$ alkylene)-S(=O)$_2$—;

$L_2$ is a bivalent radical selected from —(C(R$_4$)(R$_5$))$_n$—($C_{0-3}$ alkylene)-, —(C(R$_4$)(R$_5$))$_n$—$C_{0-3}$ alkylene)-(C—OR$^e$)—, —(C(R$_4$)(R$_5$))$_n$—($C_{0-3}$ alkylene)-C(=O)—, —(C(R$_4$)(R$_5$))$_n$—($C_{0-3}$ alkylene)-C(=N—OH)—, —(C(R$_4$)(R$_5$))$_n$—($C_{0-3}$ alkylene)-(C(=O)NR$_5$)—, —(C(R$_4$)(R$_5$))$_n$—($C_{0-3}$ alkylene)-N(R$_5$)C(=O)—, —(C(R$_4$)(R$_5$))$_n$—($C_{0-3}$ alkylene)-O—, —(C(R$_4$)(R$_5$))$_n$—($C_{0-3}$ alkylene)-N(R$_5$)—, —(C(R$_4$)(R$_5$))$_n$—($C_{0-3}$ alkylene)-S(=O)$_2$—, —(C(R$_4$)(R$_5$))$_n$—($C_{0-3}$ alkylene)-S(=O)$_2$N(R$_5$)—, or —(C(R$_4$)(R$_5$))$_n$—($C_{0-3}$ alkylene)-N(R$_5$)S(=O)$_2$—;

wherein each $R_4$ is H or optionally substituted $C_{1-6}$ alkyl; and each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —($C_{0-4}$ alkylene)-OR$^f$, —($C_{0-4}$ alkylene)-($C_{1-4}$ alkene), —($C_{0-4}$ alkylene)-($C_{1-4}$ alkyne), $C_2$-$C_7$ heterocycle, —($C_{0-4}$ alkylene)-C(=O)—($C_1$-$C_6$ alkyl), —($C_{0-4}$ alkylene)-C(=O)H, —($C_{0-4}$ alkylene)-C(=O)OR$^f$, —($C_{0-4}$ alkylene)-CN, —($C_{0-4}$ alkylene)-halo, —($C_{0-4}$ alkylene)-NO$_2$, —($C_{0-4}$ alkylene)-N(R$^f$)$_2$, —($C_{0-4}$ alkylene)-S(=O)$_2$—(R$^f$), —($C_{0-4}$ alkylene)-($C_{6-14}$ aryl), —($C_{1-4}$ alkylene)-(5- to 14-membered heteroaryl), —($C_{0-4}$ alkylene)-C(=O)NR$^b$R$^f$ or —($C_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from a bond, —($C_{1-6}$ alkylene)-, —($C_{2-6}$ alkenylene)-, or —($C_{2-6}$ alkynylene)-, —($C_{3-10}$ heterocycloalkylene)-, —($C_{6-14}$ arylene)-, -(5- to 14-membered heteroarylene)-;

R$^a$, R$^b$, R$^c$, R$^d$, and R$^e$ are each independently, at each occurrence, H or $C_{1-6}$ alkyl;

n is 1 or 2;

p is 0, 1, 2, or 3; and r is 0, 1, 2, or 3.

In some embodiments, $L_2$ is substituted or unsubstituted $C_{1-3}$ alkylene, substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-C(=N—OH)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, substituted or unsubstituted $C_{0-3}$ alkylene-S(=O)$_2$—, substituted or unsubstituted $C_{0-3}$ alkylene-S(=O)$_2$N(R$_5$)—, or substituted or unsubstituted $C_{0-3}$ alkylene-N(R$_5$)S(=O)$_2$—. In some embodiments, $L_2$ is substituted or unsubstituted $C_{1-3}$ alkylene, substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, $L_2$ is substituted or unsubstituted $C_{1-3}$ alkylene, substituted or unsubstituted $C_{0-3}$ alkylene-O—, or substituted or unsubstituted $C_{0-3}$ alkylene-N(R$_5$)—. In some embodiments, $L_2$ is substituted or unsubstituted $C_{1-3}$ alkylene or substituted or unsubstituted $C_{0-3}$ alkylene-N(R$_5$)—. In some embodiments, $L_2$ is substituted or unsubstituted $C_{0-3}$ alkylene-(C—OR$^c$)—, substituted or unsubstituted $C_{0-3}$ alkylene-C(=O)—, substituted or unsubstituted $C_{0-3}$ alkylene-(C(=O)NR$_5$)—, substituted or unsubstituted $C_{0-3}$ alkylene-N(R$_5$)C(=O)—, substituted or unsubstituted $C_{0-3}$ alkylene-O—, substituted or unsubstituted $C_{0-3}$ alkylene-N(R$_5$)—, or substituted or unsubstituted $C_{0-3}$ alkylene-S(=O)$_2$—. In some embodiments, $L_2$ is substituted or unsubstituted $C_{0-3}$ alkylene-(C—OR$^c$)— or substituted or unsubstituted $C_{0-3}$ alkylene-C(=O)—. In some embodiments, $L_2$ is substituted or unsubstituted $C_{0-3}$ alkylene-(C(=O)NR$_5$)—, substituted or unsubstituted $C_{0-3}$ alkylene-N(R$_5$)C(=O)—.

In one embodiment of Formula V, $R_6$ and $R_7$ are each independently, at each occurrence, —OH, —NH$_2$, —CN, —NO$_2$, —C(=O)OR$^b$, —C(=O) N(R$^b$)$_2$, —N(R$^b$)C(=O) OR$^b$, halo, $C_{1-6}$ alkyl, $C_{1-6}$ alkoxy, or =O.

In another embodiment of Formula V, $R_5$ is H, $C_{1-6}$ alkyl, —($C_{1-4}$ alkylene)-OR$^d$, —($C_{1-4}$ alkylene)-N(R$^d$)$_2$, —($C_{1-4}$ alkylene)-S(=O)$_2$—(R$^d$), —($C_{1-4}$ alkylene)-($C_{6-14}$ aryl), or —($C_{1-4}$ alkylene)-(5- to 14-membered heteroaryl).

In yet another aspect, the disclosure provides a compound of Formula VI:

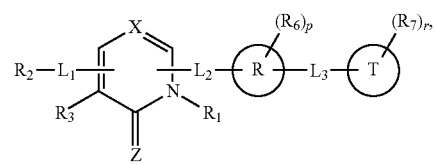

or a pharmaceutically acceptable salt thereof,
wherein:
$R_1$ is H, $C_{1-6}$ alkyl, —OH, —NH$_2$, or SH;
$R_2$ is H, —OR$^a$, —N(R$^a$)$_2$, $C_{1-6}$ alkyl, or $C_{1-6}$ alkoxy;
$R_3$ is H, $C_{1-6}$ alkyl, —OH, —NH$_2$, or SH;

$R_6$ and $R_7$ are each independently, at each occurrence, —OH, —NH$_2$, —CN, —NO$_2$, —C(=O)OR$^b$, —C(=O)N(R$^b$)$_2$, —N(R$^b$)C(=O)OR$^b$, halo, C$_{1-6}$ alkyl, C$_{1-6}$ alkoxy, =O, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

ring R is C$_{3-7}$ cycloalkyl, C$_{3-10}$ heterocycloalkyl, C$_{6-14}$ aryl, or a 5- to 14-membered heteroaryl;

ring T is C$_{3-7}$ cycloalkyl, C$_{3-10}$ heterocycloalkyl, C$_{6-14}$ aryl, or a 5- to 14-membered heteroaryl;

X is C(H), S, or N;

Z is O or S;

$L_1$ is a bivalent radical selected from a bond, —C(=O)—, —(C(=O)O)—, —OC(=O)—, —(C(=O)NR$^b$)—, —N(R$^b$)C(=O)—, —N(R$^b$)—, —S(=O)$_2$—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—;

$L_2$ is a bivalent radical selected from —(C(R$_4$)(R$_5$))$_n$—(C$_{0-3}$ alkylene)-, —(C(R$_4$)(R$_5$))$_n$-C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;

wherein each $R_4$ is H or optionally substituted C$_{1-6}$ alkyl; and each $R_5$ is independently H, an optionally substituted C$_{1-6}$ alkyl, an optionally substituted C$_{1-6}$ heteroalkyl, an optionally substituted C$_{1-6}$ alkenyl, an optionally substituted C$_{1-6}$ alkynyl, an optionally substituted C$_{6-14}$ aryl, an optionally substituted 5- to 14-membered heteroaryl, an optionally substituted C$_3$-C$_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$;

wherein each R$^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from a bond, —(C$_{1-6}$ alkylene)-, —(C$_{2-6}$ alkenylene)-, or —(C$_{2-6}$ alkynylene)-, —(C$_{3-10}$ heterocycloalkylene)-, —(C$_{6-14}$ arylene)-, -(5- to 14-membered heteroarylene)-;

R$^a$, R$^b$, R$^c$, R$^d$, and R$^e$ are each independently, at each occurrence, H or C$_{1-6}$ alkyl;

n is 1 or 2;

p is 0, 1, 2, or 3; and r is 0, 1, 2, or 3.

In some embodiments, $L_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-C(=N—OH)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, substituted or unsubstituted C$_{0-3}$ alkylene-S(=O)$_2$—, substituted or unsubstituted C$_{0-3}$ alkylene-S(=O)$_2$N(R$_5$)—, or substituted or unsubstituted C$_{0-3}$ alkylene-N(R$_5$)S(=O)$_2$—. In some embodiments, $L_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)-, substituted or unsubstituted C$_{0-3}$ alkylene-S(=O)$_2$—, substituted or unsubstituted C$_{0-3}$ alkylene-S(=O)$_2$N(R$_5$)—, or substituted or unsubstituted C$_{0-3}$ alkylene-N(R$_5$)S(=O)$_2$—. In some embodiments, $L_2$ is substituted or unsubstituted C$_{1-3}$ alkylene, substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, or substituted or unsubstituted C$_{0-3}$ alkylene-S(=O)$_2$—. In some embodiments, $L_2$ is substituted or unsubstituted C$_{1-3}$ alkylene, substituted or unsubstituted C$_{0-3}$ alkylene-O—, substituted or unsubstituted C$_{0-3}$ alkylene-N(R$_5$)—, or substituted or unsubstituted C$_{0-3}$ alkylene-S(=O)$_2$—. In some embodiments, $L_2$ is substituted or unsubstituted C$_{1-3}$ alkylene, substituted or unsubstituted C$_{0-3}$ alkylene-O—, or substituted or unsubstituted C$_{0-3}$ alkylene-N(R$_5$)—. In some embodiments, $L_2$ is substituted or unsubstituted C$_{1-3}$ alkylene or substituted or unsubstituted C$_{0-3}$ alkylene-N(R$_5$)—. In some embodiments, $L_2$ is substituted or unsubstituted C$_{0-3}$ alkylene-(C—OR$^c$)—, substituted or unsubstituted C$_{0-3}$ alkylene-C(=O)—, substituted or unsubstituted C$_{0-3}$ alkylene-(C(=O)NR$_5$)—, substituted or unsubstituted C$_{0-3}$ alkylene-N(R$_5$)C(=O)—, substituted or unsubstituted C$_{0-3}$ alkylene-O—, substituted or unsubstituted C$_{0-3}$ alkylene-N(R$_5$)—, or substituted or unsubstituted C$_{0-3}$ alkylene-S(=O)$_2$—. In some embodiments, $L_2$ is substituted or unsubstituted C$_{0-3}$ alkylene-(C—OR$^c$)— or substituted or unsubstituted C$_{0-3}$ alkylene-C(=O)—. In some embodiments, $L_2$ is substituted or unsubstituted C$_{0-3}$ alkylene-(C(=O)NR$_5$)—, substituted or unsubstituted C$_{0-3}$ alkylene-N(R$_5$)C(=O)—.

In some embodiments of Formula V or of Formula VI, Z is O. In another embodiment of Formula V or of Formula VI, Z is S. In still another embodiment, X is N. In yet another embodiment, $L_1$ bivalent radical selected from a bond, —(C$_{1-4}$ alkylene)-O—, —(C$_{1-4}$ alkylene)-N(R$^b$)—, —(C$_{1-4}$ alkylene)-S—, or —(C$_{1-4}$ alkylene)-S(=O)$_2$—; $R_2$ is H, —OR$^a$, —N(R$^a$)$_2$, C$_{1-6}$ alkyl, or C$_{1-6}$ alkoxy; and R$^b$ is H or C$_{1-6}$ alkyl. In one embodiment, $R_5$ is not hydrogen. In another embodiment, $R_5$ is —(C$_{0-4}$ alkylene)-OR$^f$, —(C$_{0-4}$ alkylene)-N(10$_2$, —(C$_{0-4}$ alkylene)-S(=O)$_2$—(R$^f$), —(C$_{0-4}$ alkylene)-(C$_{6-14}$ aryl), or —(C$_{0-4}$ alkylene)-(5- to 14-membered heteroaryl). In certain embodiments, $R_5$ is —(C$_{0-4}$ alkylene)-OR$^f$, —(C$_{0-4}$ alkylene)-N(R$^f$)$_2$, or —(C$_{0-4}$ alkylene)-S(=O)$_2$—(R$^f$). In yet another embodiment, $L_3$ is a bivalent radical selected from —(C$_{2-6}$ alkenylene)-, —(C$_{2-6}$ alkynylene)-, —(C$_{3-10}$ heterocycloalkylene)-, —(C$_{6-14}$ arylene)-, or -(5- to 14-membered heteroarylene)-. In still another embodiment, $L_3$ is a bond. In yet another embodiment, p is 1, and $R_6$ is =O. In a further embodiment, ring R with one $R_6$ substituent forms a pyridinone ring (p is 1, and $R_6$ is =O). In some embodiments, ring R with one $R_6$ substituent forms a 2-pyridinone ring.

In one embodiment of Formula VI, $R_6$ and $R_7$ are each independently, at each occurrence, —OH, —NH$_2$, —CN, —NO$_2$, —C(=O)OR$^b$, —C(=O) N(R$^b$)$_2$, —N(R$^b$)C(=O) OR$^b$, halo, $C_{1-6}$ alkyl, $C_{1-6}$ alkoxy, or =O.

In another embodiment of Formula VI, $R_5$ is H, $C_{1-6}$ alkyl, —($C_{1-4}$ alkylene)-OR$^d$, —($C_{1-4}$ alkylene)-N(R$^d$)$_2$, —($C_{1-4}$ alkylene)-S(=O)$_2$—(R$^d$), —($C_{1-4}$ alkylene)-($C_{6-14}$ aryl), or —($C_{1-4}$ alkylene)-(5- to 14-membered heteroaryl).

In yet another aspect, the disclosure provides compounds having the structural formulas provided in Table 1.

TABLE 1

Select compounds of the disclosure.

| Compound ID No. | Structure |
|---|---|
| 70 | 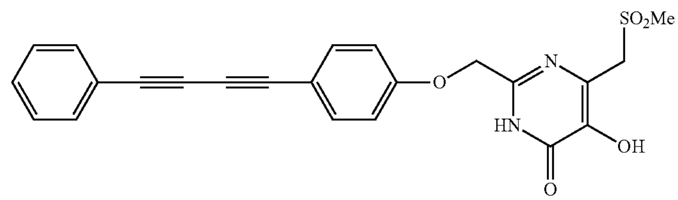 [SMILES: CS(=O)(=O)Cc1nc(COc2ccc(C#CC#Cc3ccccc3)cc2)[nH]c(=O)c1O] |
| 71 | 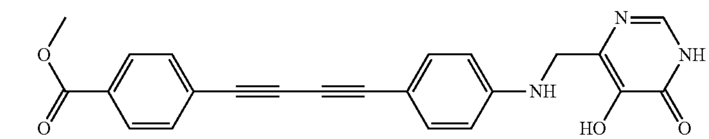 [SMILES: COC(=O)c1ccc(C#CC#Cc2ccc(NCc3nc[nH]c(=O)c3O)cc2)cc1] |
| 72 | 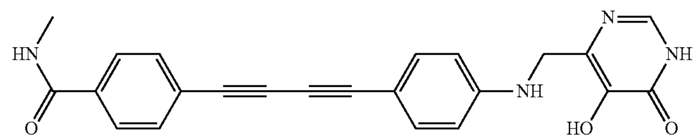 [SMILES: CNC(=O)c1ccc(C#CC#Cc2ccc(NCc3nc[nH]c(=O)c3O)cc2)cc1] |
| 73 | 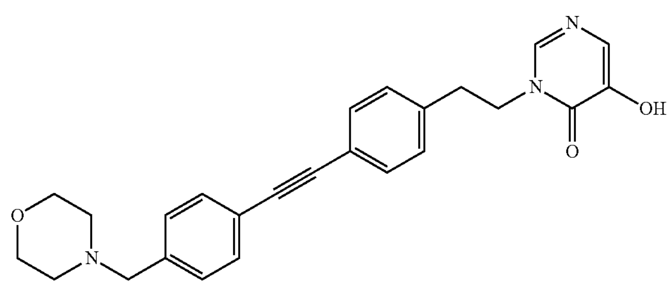 [SMILES: O=c1c(O)cncn1CCc1ccc(C#Cc2ccc(CN3CCOCC3)cc2)cc1] |
| 74 | 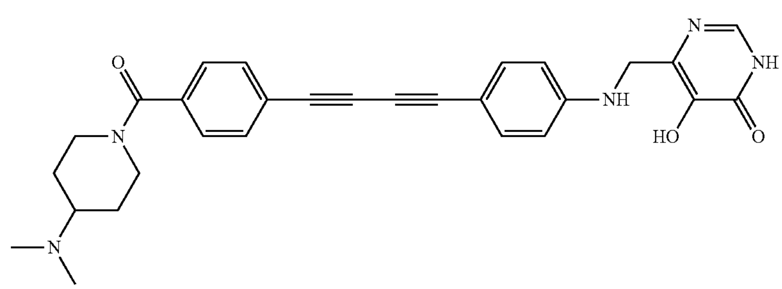 [SMILES: CN(C)C1CCN(C(=O)c2ccc(C#CC#Cc3ccc(NCc4nc[nH]c(=O)c4O)cc3)cc2)CC1] |
| 75 | 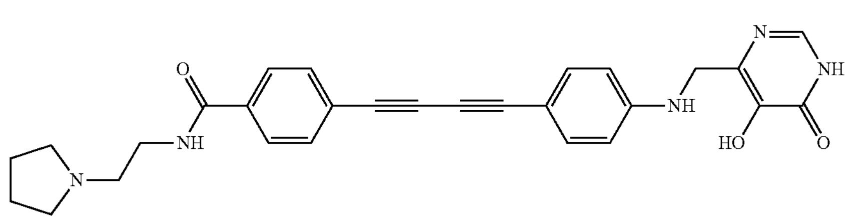 [SMILES: O=C(NCCN1CCCC1)c1ccc(C#CC#Cc2ccc(NCc3nc[nH]c(=O)c3O)cc2)cc1] |

TABLE 1-continued

Select compounds of the disclosure.

| Compound ID No. | Structure |
|---|---|
| 76 | 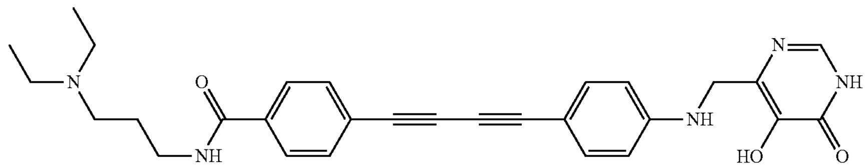 [SMILES: CCN(CC)CCCNC(=O)c1ccc(C#CC#Cc2ccc(NCc3nc[nH]c(=O)c3O)cc2)cc1] |
| 77 | 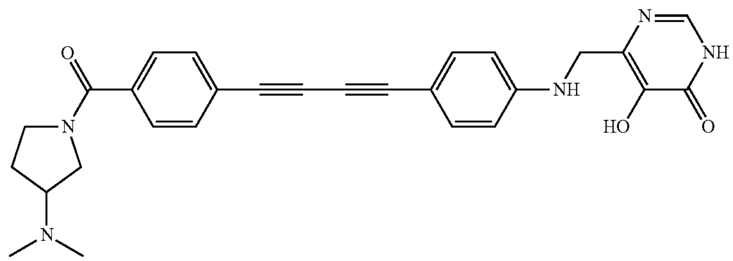 [SMILES: CN(C)C1CCN(C(=O)c2ccc(C#CC#Cc3ccc(NCc4nc[nH]c(=O)c4O)cc3)cc2)C1] |
| 78 | 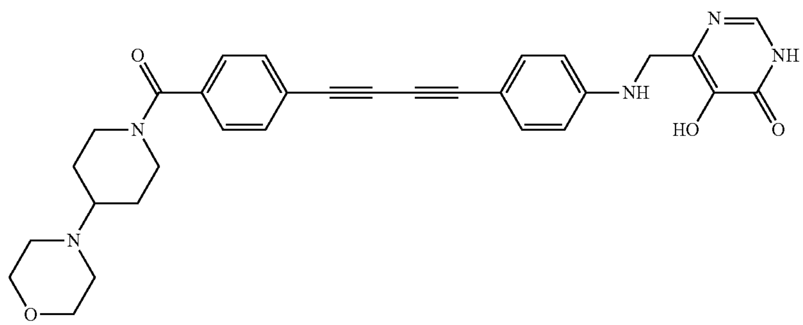 [SMILES: O=C(c1ccc(C#CC#Cc2ccc(NCc3nc[nH]c(=O)c3O)cc2)cc1)N1CCC(N2CCOCC2)CC1] |
| 79 | 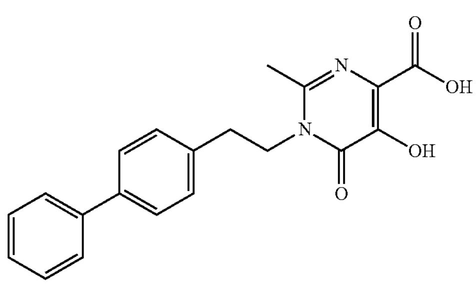 [SMILES: Cc1nc(C(=O)O)c(O)c(=O)n1CCc1ccc(-c2ccccc2)cc1] |
| 80 | 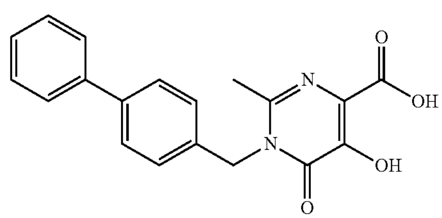 [SMILES: Cc1nc(C(=O)O)c(O)c(=O)n1Cc1ccc(-c2ccccc2)cc1] |
| 81 | 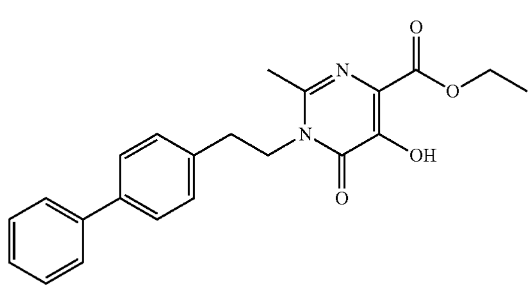 [SMILES: CCOC(=O)c1nc(C)n(CCc2ccc(-c3ccccc3)cc2)c(=O)c1O] |

TABLE 1-continued

Select compounds of the disclosure.

| Compound ID No. | Structure |
|---|---|
| 82 | 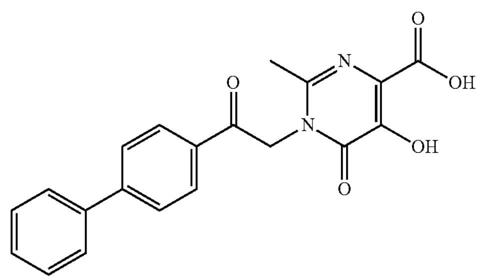 [SMILES: Cc1nc(C(=O)O)c(O)c(=O)n1CC(=O)c1ccc(-c2ccccc2)cc1] |
| 83 | 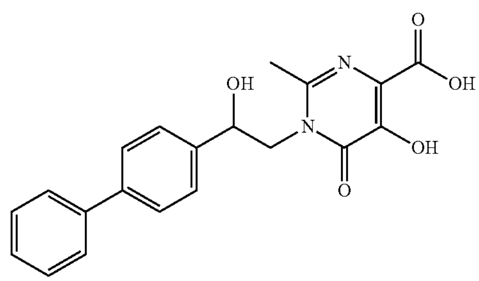 [SMILES: Cc1nc(C(=O)O)c(O)c(=O)n1CC(O)c1ccc(-c2ccccc2)cc1] |
| 84 | 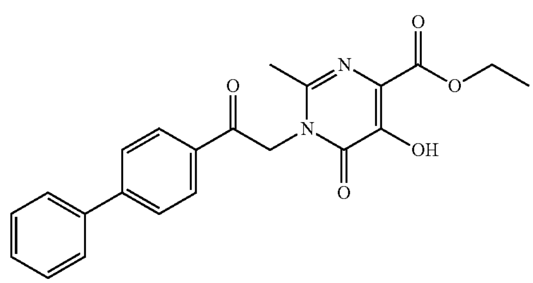 [SMILES: CCOC(=O)c1nc(C)n(CC(=O)c2ccc(-c3ccccc3)cc2)c(=O)c1O] |
| 85 | 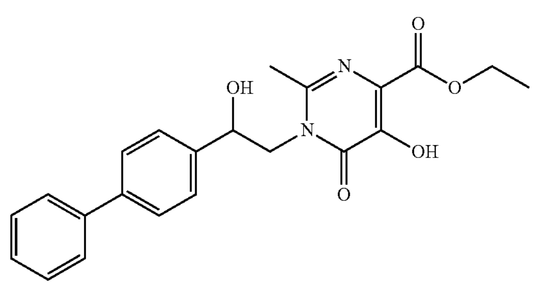 [SMILES: CCOC(=O)c1nc(C)n(CC(O)c2ccc(-c3ccccc3)cc2)c(=O)c1O] |
| 86 | 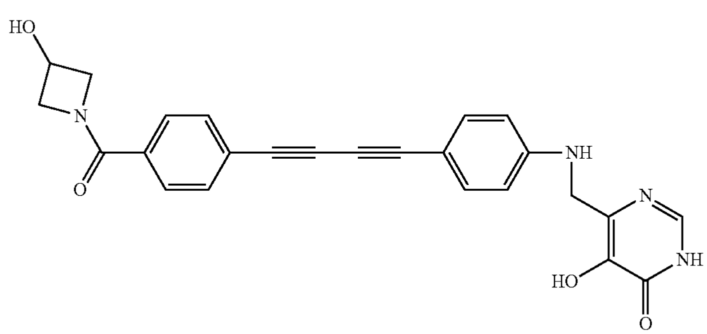 [SMILES: O=C(c1ccc(C#CC#Cc2ccc(NCc3nc[nH]c(=O)c3O)cc2)cc1)N1CC(O)C1] |

TABLE 1-continued
Select compounds of the disclosure.
| Compound ID No. | Structure |
|---|---|
| 87 | 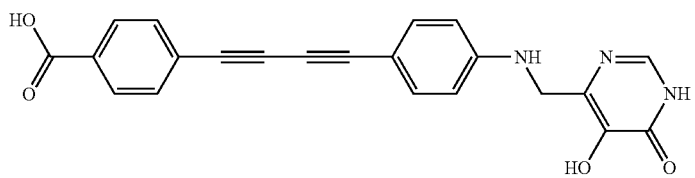 |
| 88 | 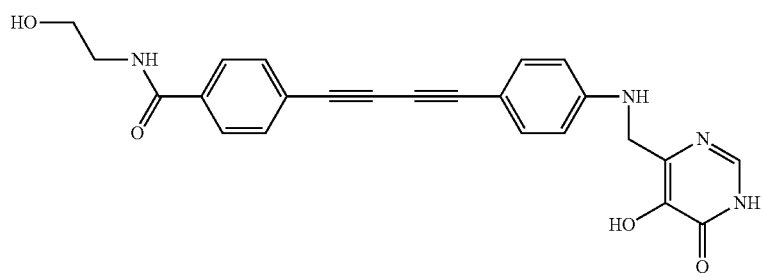 [SMILES: O=C(NCCO)c1ccc(C#CC#Cc2ccc(NCc3nc[nH]c(=O)c3O)cc2)cc1] |
| 89 | 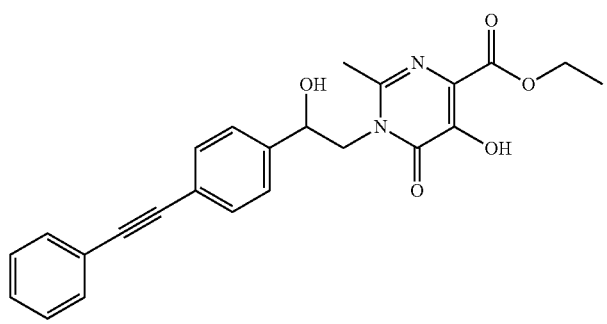 [SMILES: CCOC(=O)c1nc(C)n(CC(O)c2ccc(C#Cc3ccccc3)cc2)c(=O)c1O] |
| 90 | 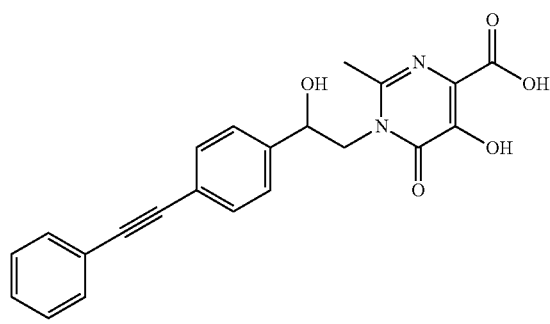 [SMILES: Cc1nc(C(=O)O)c(O)c(=O)n1CC(O)c1ccc(C#Cc2ccccc2)cc1] |
| 91 | 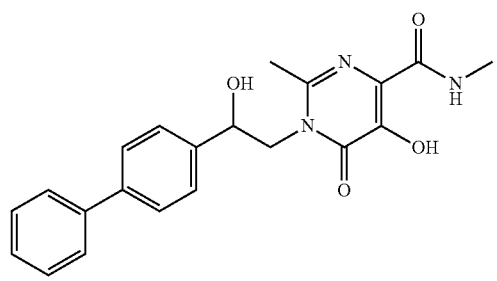 [SMILES: CNC(=O)c1nc(C)n(CC(O)c2ccc(-c3ccccc3)cc2)c(=O)c1O] |

TABLE 1-continued
Select compounds of the disclosure.
| Compound ID No. | Structure |
|---|---|
| 92 | 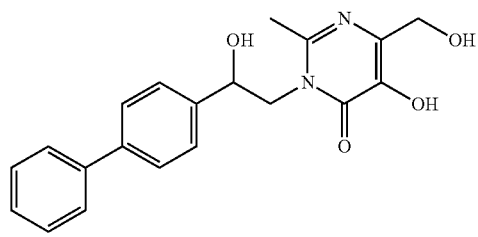 [SMILES: Cc1nc(CO)c(O)c(=O)n1CC(O)c1ccc(-c2ccccc2)cc1] |
| 93 | 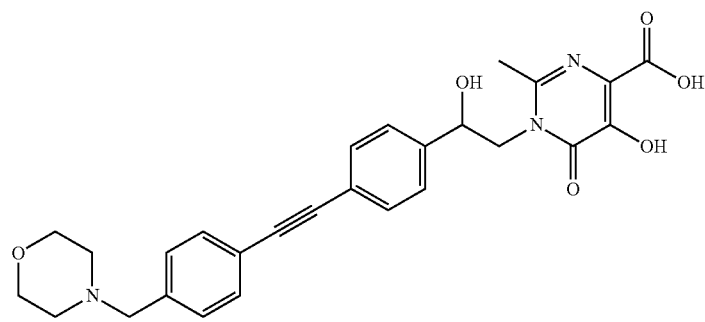 [SMILES: Cc1nc(C(=O)O)c(O)c(=O)n1CC(O)c1ccc(C#Cc2ccc(CN3CCOCC3)cc2)cc1] |
| 94 | 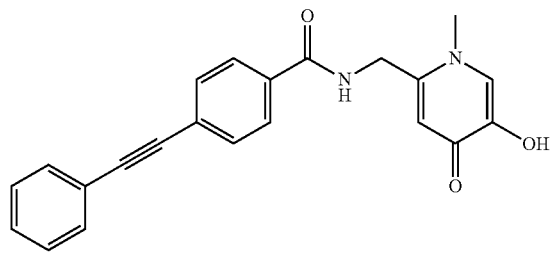 [SMILES: Cn1cc(O)c(=O)cc1CNC(=O)c1ccc(C#Cc2ccccc2)cc1] |
| 95 | 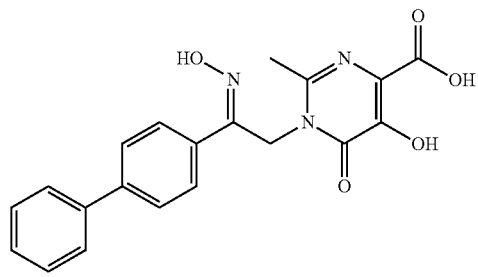 [SMILES: Cc1nc(C(=O)O)c(O)c(=O)n1C/C(=N/O)c1ccc(-c2ccccc2)cc1] |
| 96 | 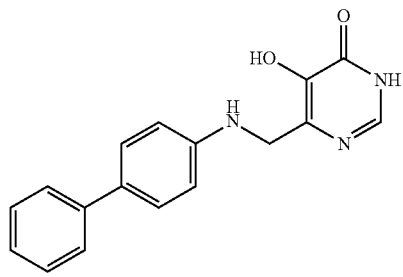 [SMILES: O=c1[nH]cnc(CNc2ccc(-c3ccccc3)cc2)c1O] |
| 97 | 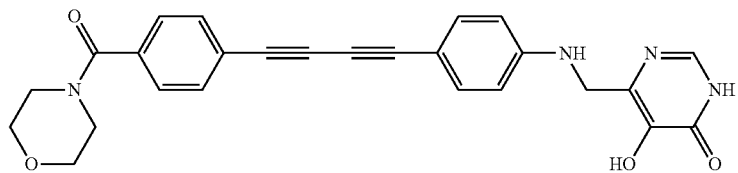 [SMILES: O=C(c1ccc(C#CC#Cc2ccc(NCc3nc[nH]c(=O)c3O)cc2)cc1)N1CCOCC1] |

TABLE 1-continued
Select compounds of the disclosure.
| Compound ID No. | Structure |
|---|---|
| 98 | 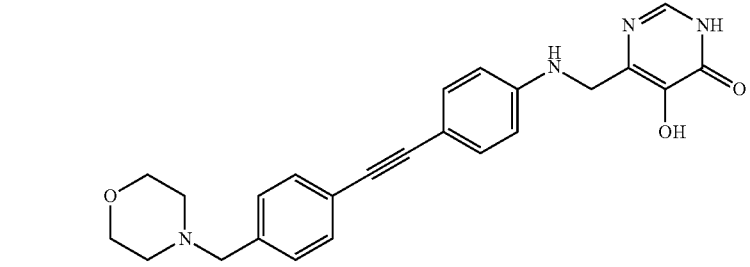 [SMILES: O=c1[nH]cnc(CNc2ccc(C#Cc3ccc(CN4CCOCC4)cc3)cc2)c1O] |
| 99 | 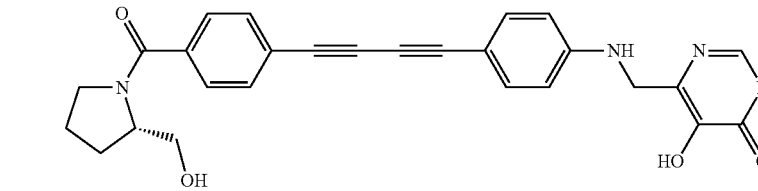 |
| 100 | 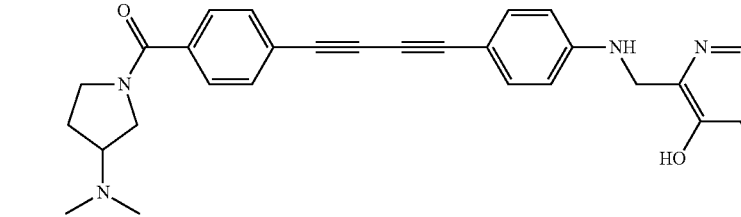 |
| 101 | 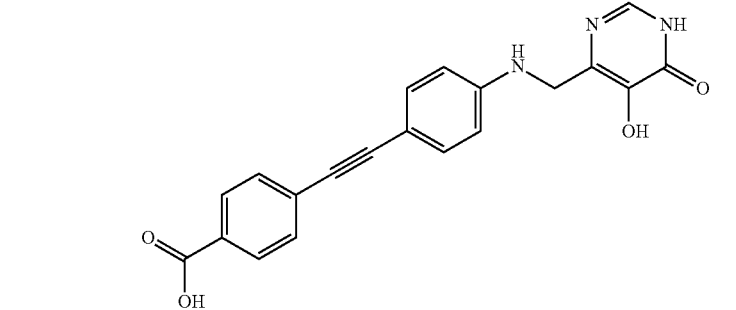 [SMILES: O=C(O)c1ccc(C#Cc2ccc(NCc3nc[nH]c(=O)c3O)cc2)cc1] |
| 102 | 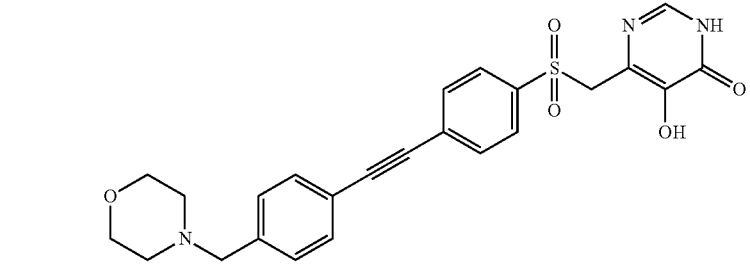 [SMILES: O=c1[nH]cnc(CS(=O)(=O)c2ccc(C#Cc3ccc(CN4CCOCC4)cc3)cc2)c1O] |

TABLE 1-continued

Select compounds of the disclosure.

| Compound ID No. | Structure |
|---|---|
| 103 | 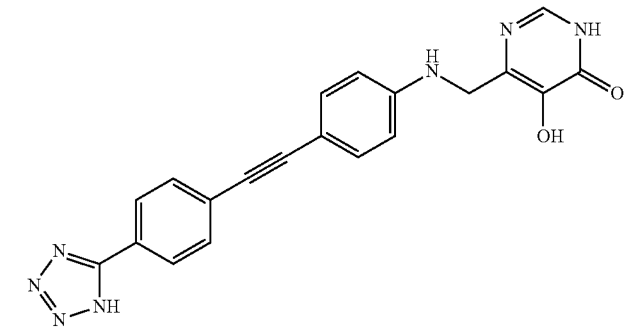 [SMILES: O=c1[nH]cnc(CNc2ccc(C#Cc3ccc(-c4nnn[nH]4)cc3)cc2)c1O] |
| 104 | 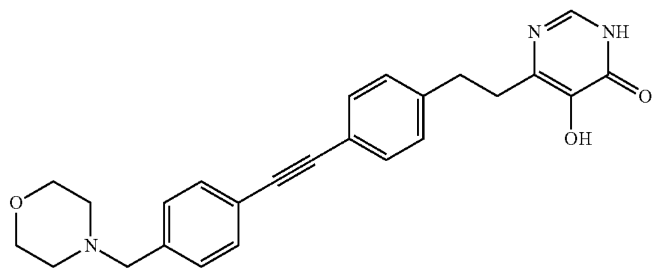 [SMILES: O=c1[nH]cnc(CCc2ccc(C#Cc3ccc(CN4CCOCC4)cc3)cc2)c1O] |
| 105 | 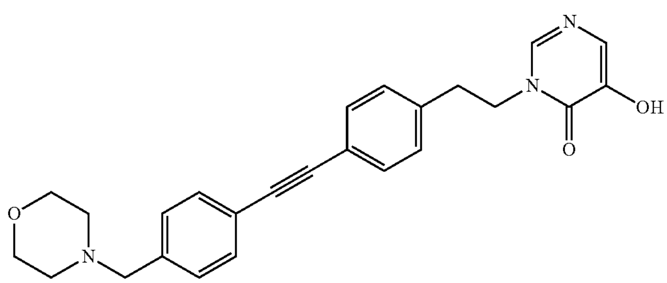 [SMILES: O=c1c(O)cncn1CCc1ccc(C#Cc2ccc(CN3CCOCC3)cc2)cc1] |
| 106 | 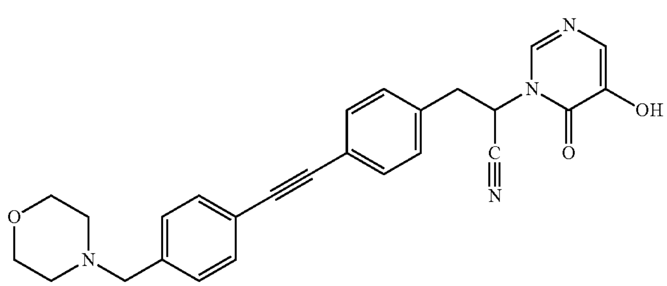 [SMILES: N#CC(Cc1ccc(C#Cc2ccc(CN3CCOCC3)cc2)cc1)n1cncc(O)c1=O] |
| 107 | 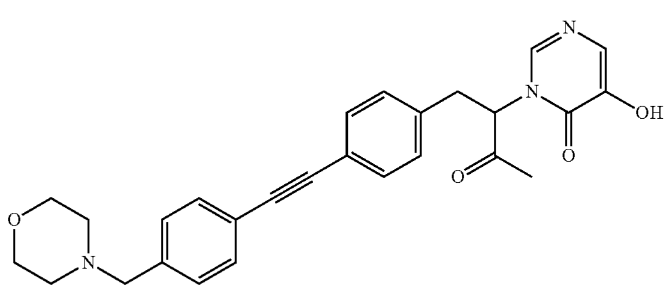 [SMILES: CC(=O)C(Cc1ccc(C#Cc2ccc(CN3CCOCC3)cc2)cc1)n1cncc(O)c1=O] |

TABLE 1-continued
Select compounds of the disclosure.
| Compound ID No. | Structure |
|---|---|
| 108 | 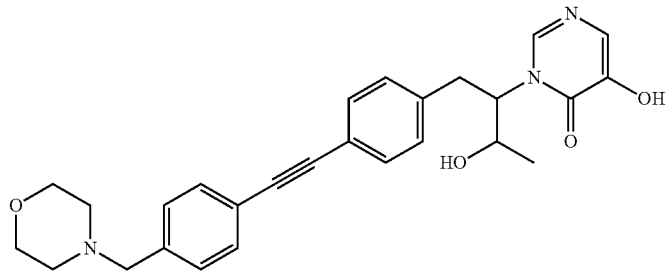 [SMILES: CC(O)C(Cc1ccc(C#Cc2ccc(CN3CCOCC3)cc2)cc1)n1cncc(O)c1=O] |
| 110 | 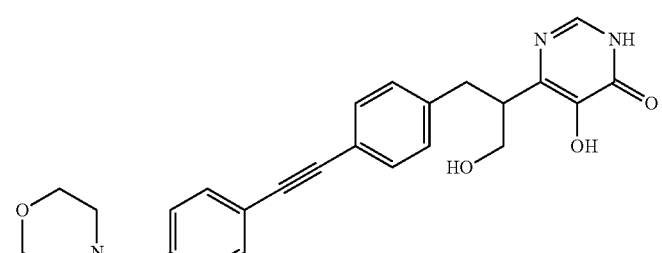 |
| 111 | 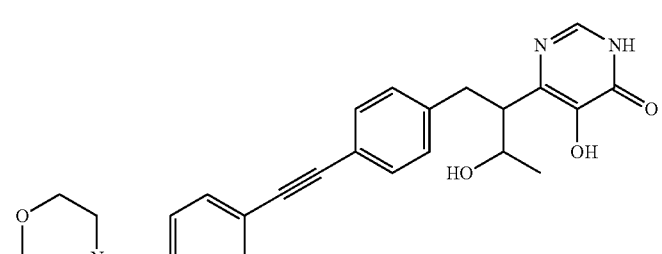 |
| 112 | 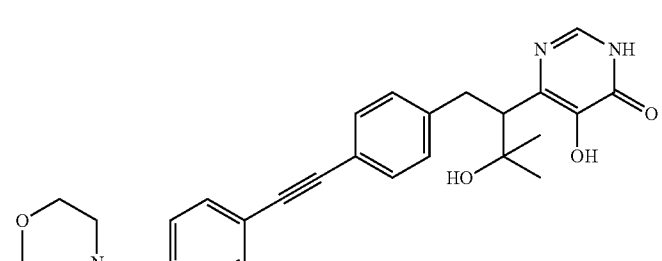 |
| 113 | 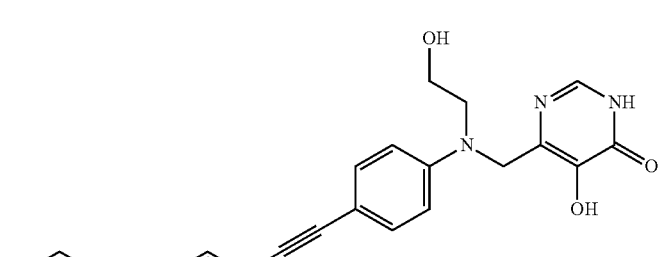 |

TABLE 1-continued

Select compounds of the disclosure.

| Compound ID No. | Structure |
|---|---|
| 114 | (structure) |

Pharmaceutical Compositions

As used herein the term "pharmaceutical composition" refers to a preparation of one or more of the components described herein, or pharmaceutically acceptable salts thereof, with other chemical components such as physiologically suitable carriers and excipients. The purpose of a pharmaceutical composition is to facilitate administration of a compound to a patient or subject.

The term "excipient" refers to an inert or inactive substance added to a pharmaceutical composition to further facilitate administration of a compound. Non-limiting examples of excipients include calcium carbonate, calcium phosphate, various sugars and types of starch, cellulose derivatives, gelatin, vegetable oils and polyethylene glycols.

The present teachings further comprise pharmaceutical compositions comprising one or more of the compounds of the present disclosure, and at least one pharmaceutically acceptable excipient.

In some embodiments, compositions are administered to humans, human patients or subjects. For the purposes of the present disclosure, the phrase "active ingredient" generally refers to a compound to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Subjects to which administration of the pharmaceutical compositions is contemplated include, but are not limited to, non-human mammals, including cattle, pigs, cats, dogs, mice, and rats.

Dosing

The present disclosure provides methods comprising administering compounds of the disclosure to a subject in need thereof. Metalloprotein modulator compounds as described herein may be administered to a subject using any amount and any route of administration effective for treating a disease, a disorder, or a condition (e.g., a disease, a disorder, or a condition relating to gram-negative bacterial infections).

Compositions in accordance with the disclosure are typically formulated in dosage unit form for ease of administration and uniformity of dosage. It will be understood, however, that the total daily usage of the compositions of the present disclosure may be decided by the attending physician within the scope of sound medical judgment. The specific therapeutically effective or prophylactically effective dose level for any particular subject will depend upon a variety of factors including the species, age, body weight, general health, sex and diet of the subject; the disorder or disease being treated and the severity of the disorder or disease; the activity of the specific compound employed; the specific composition employed; the time of administration, route of administration, and rate of excretion of the specific compound employed; the duration of the treatment; drugs used in combination or coincidental with the specific compound employed; and like factors well known in the medical arts.

Use of Metalloprotein Modulators

Metalloproteins influence a vast diversity of biological systems, biological processes, and diseases. For example, LpxC, a zinc-dependent deacetylase, catalyzes the first committed step in Lipid A biosynthesis. Lipid A is an essential component of the outer membrane of gram-negative bacteria. LpxC is highly conserved across strains of gram-negative bacteria. Therefore, inhibitors of LpxC may provide effective alternative antibacterial agents.

In another aspect, the disclosure provides a method of modulating the activity of a metalloprotein such as LpxC in a subject in need thereof comprising administering to the subject a metalloprotein modulator comprising a hydroxypyridinone or hydroxypyrimidinone derivative. The hydroxypyridinone or hydroxypyrimidinone will bind to the catalytic zinc(II) ion and inhibit LpxC. LpxC has been implicated in diseases including bacterial infection. In some embodiments, the gram-negative bacterial infection is a urinary tract infection, a hospital acquired/ventilator-associated pneumonia, or an intra-abdominal infection.

In another aspect, the disclosure provides a method for treating or ameliorating one or more diseases associated with a metalloprotein function or activity comprising administering a therapeutically effect amount of a metalloprotein modulator. In some embodiments, the metalloprotein modulator inhibits the activity of a metalloprotein, LpxC.

In another embodiment, the LpxC inhibitor is a compound of Formula I, a compound of Formula II, a compound of Formula III, a compound of Formula IV, a compound of Formula V, or a compound of Formula VI.

In still another aspect, the disclosure provides a method of modulating the activity of LpxC in a subject in need thereof comprising administering a therapeutically effective amount of a compound of Formula I, a compound of Formula II, a compound of Formula III, a compound of Formula IV, a compound of Formula V, a compound of Formula VI, or a pharmaceutically acceptable salt thereof.

In another embodiment, methods of treatment to treat or to ameliorate a gram-negative bacterial infection are provided. The compounds of the disclosure can be used for treating conditions caused by the bacterial production of endotoxin and, in particular, by gram-negative bacteria and bacteria that use LpxC in the biosynthesis of lipopolysaccharide (LPS) or endotoxin. In some embodiments, the method of treating a gram-negative bacterial infection in a subject comprises administering to the subject a pharmaceutical composition comprising a compound of Formula I, a compound of Formula II, a compound of Formula III, a compound of Formula IV, a compound of Formula V, a compound of Formula VI, or a pharmaceutically acceptable salt thereof.

One embodiment provided herein describes the use of a compound of Formula I, a compound of Formula II, a compound of Formula III, a compound of Formula IV, a compound of Formula V, a compound of Formula VI, or a pharmaceutically acceptable salt thereof in the manufacture of a medicament. Another embodiment provided herein describes a compound of Formula I, a compound of Formula II, a compound of Formula III, a compound of Formula IV, a compound of Formula V, a compound of Formula VI, or a pharmaceutically acceptable salt thereof for use as a medicament. In some embodiments, the medicament is used for the treatment of a bacterial infection. In some embodiments, the medicament is used for the treatment of a gram-negative bacterial infection.

In yet another embodiment, the compounds of the disclosure also are useful in the treatment of patients suffering from or susceptible to pneumonia, sepsis, cystic fibrosis, intra-abdominal infection, skin infections or urinary tract infections.

In yet another embodiment, the compounds of the disclosure also are useful in the treatment of patients suffering from chronic urinary tract infections, complicated urinary tract infections, cystitis, pyelonephritis, urethritis, recurrent urinary tract infections, bladder infections, urethral infections or kidney infections. In some embodiments, the compounds described herein are used for the treatment of complicated urinary tract infections.

In another embodiment, the compounds of the disclosure also are useful in the treatment of patients suffering from complicated intra-abdominal infection, peritonitis, intra-abdominal abscesses, diverticulitis, appendicitis, antibiotic associated diarrhea or intra-abdominal sepsis. In certain embodiments, the compounds described herein are used for treating chronic intra-abdominal infection.

In other embodiments, the compounds of the disclosure also are useful in the treatment of patients suffering from hospital acquired pneumonia, ventilator associated pneumonia, healthcare-associated pneumonia, community-acquired pneumonia or nosocomial pneumonia. In certain embodiments, the compounds described herein are used for treating hospital acquired pneumonia and ventilator associated pneumonia.

In still another embodiment, the compounds of the disclosure also are useful in the conditions that are caused or exacerbated by the bacterial production of lipid A and LPS or endotoxin, such as sepsis, septic shock, systemic inflammation, localized inflammation, chronic obstructive pulmonary disease (COPD) and acute exacerbations of chronic bronchitis (AECB).

In other embodiments, the compounds of the disclosure can be used for the treatment of a serious or chronic respiratory tract or complicated urinary tract infections including serious lung and nosocomial infections such as those caused by *Enterobacter aerogenes, Enterobacter cloacae, Escherichia coli, Klebsiella pneumoniae, Klebsiella oxytoca, Proteus mirabilis, Serratia marcescens, Stenotrophomonas maltophilia, Pseudomonas aeruginosa, Burkholderia cepacia, Acinetobacter baumannii, Alcaligenes xylosoxidans, Flavobacterium meningosepticum, Providencia sluarlii* and *Citrobacter freundi*, community lung infections such as those caused by *Haemophilus influenzae, Legionella* species, *Moraxella catarrhalis, Enterobacter* species, *Acinetobacter* species, *Klebsiella* species, *Burkholderia* species, and *Proteus* species, and infections caused by other bacterial species such as *Neisseria* species, *Shigella* species, *Salmonella* species, *Helicobacler pylori, Vibrionaceae* and *Bordetella* species as well as the infections caused by a *Brucella* species, *Francisella tularensis* and/ or *Yersinia pestis*.

Inhibited Metalloproteins

This disclosure includes complexes of bacterial metalloproteins reversibly bound or chelated to any of the compounds of Formula I, Formula II, Formula III, Formula IV, Formula IVA, Formula IVB, Formula V, Formula VI, or a deprotonated analogue thereof. The aforementioned complex has reduced or no catalytic activity as compared to the non-complexed metalloprotein.

Also described herein are inhibited metalloprotein enzymes. In one embodiment, the metalloprotein comprises zinc. In one embodiment, the metalloprotein is UDP-{3-O—[(R)-3-hydroxymyristoyl]}-N-acetylglucosamine deacetylase (LpxC). Also described herein are reversible inhibitors of LpxC. Further described are reversible inhibitors of LpxC that bond or coordinate via one or more bonds to the zinc metal center.

Some embodiments provided herein describe reversible inhibitors of other deacetylase metalloproteins, wherein the other deacetylase metalloprotein share homology with LpxC by having a zinc ion metal center that can form a coordinate bond with the reversible inhibitor. Also described herein are methods for synthesizing such reversible inhibitors, methods for using such reversible inhibitors in the treatment of diseases (including diseases wherein reversible inhibition of LpxC provides therapeutic benefit to a patient having a bacterial infection).

Also provided herein in some embodiments is a metalloprotein complexed to a pyridinone or pyrimidinone. In some embodiments, the metalloprotein is complexed to a hydroxypyridinone or hydroxypyrimidinone. In some embodiments, the metalloprotein is complexed to the inhibitor (e.g., hydroxypyridinone or hydroxypryimidinone) in different motifs. In some embodiments, the complexed metalloprotein is an inhibited enzyme. In some embodiments, the pyridinone or pyrimidinone complexed to the metalloprotein is a compound described herein. In certain embodiments, the pyridinone or pyrimidinone complexed to the metalloprotein is a compound having the structure of Formula I, Formula II, Formula III, Formula IV, Formula IVA, Formula IVB, Formula V, Formula VI, or a pharmaceutically acceptable salt, solvate, ester, acid or prodrug thereof.

In one embodiment, provided herein is a complex of an inhibited enzyme of Formula (A):

$$M-I \qquad \text{Formula (A)}$$

wherein:
M is a metalloprotein;
I is an inhibitor.

In some embodiments, the inhibitor is a non-hydroxamic acid compound. In some embodiments, the inhibitor is a pyridinone or pyrimidinone. In some embodiments, the inhibitor is a hydroxypyridinone or hydroxypyrimidinone. In certain embodiments, the inhibitor is a compound described herein. In some embodiments, the inhibitor is a compound having the structure of Formula I, Formula II, Formula III, Formula IV, Formula IVA, Formula IVB, Formula V, Formula VI, or a pharmaceutically acceptable salt, solvate, ester, acid or prodrugs thereof.

In one embodiment, inhibitor is bound, attached or chelated to the metalloprotein in different motifs. In one embodiment of a complex of Formula A, M and I are attached by at least one bond. In another embodiment, M and I are attached by at least one coordinate bond. In another embodiment, M and I are attached by at least two coordinate bonds. In another embodiment, M and I are attached by at least one hydrogen bond. In another embodiment, M and I are attached by at least one ionic or electrostatic bond. In another embodiment, M and I are attached by both coordinate and hydrogen bonds. In one embodiment, M and I are attached by at least two coordinate bonds and at least one hydrogen bond. In one embodiment, M and I are attached by at least two coordinate bonds and at least one hydrogen bond.

In one embodiment, M is a metalloprotein whose metal ion is chelated, attached or bound to one or more amino acids. In some embodiments, the amino acid chelated, attached, or bound to the metal ion is histidine, lysine, aspartate, threonine, aromatic phenyl alanine (e.g., phenylalanine, tryptophan, or tyrosine), glycine, glutamine, leucine, glutamate, or cysteine. In some embodiments, the amino acid chelated, attached, or bound to the metal ion is histidine, lysine, aspartate, threonine, aromatic phenyl alanine, glycine, glutamine, or leucine. In some embodiments, the amino acid chelated, attached, or bound to the metal ion is histidine, lysine, glutamate or aspartate. In some embodiments, the amino acid chelated, attached, or bound to the metal ion is histidine. In some embodiments, the amino acid chelated, attached, or bound to the metal ion is lysine. In some embodiments, the amino acid chelated, attached, or bound to the metal ion is aspartate. In some embodiments, the amino acid chelated, attached, or bound to the metal ion is glutamate.

In one embodiment, the metal ion of the inhibited metalloprotein is chelated, attached or bound to one or more amino acids selected from the group consisting of histidine, lysine, aspartate, threonine, aromatic phenyl alanine (e.g., phenylalanine, tryptophan, or tyrosine), glycine, glutamine, leucine, glutamate, and cysteine. In another embodiment, the metal ion of the metalloprotein is chelated, attached or bound to one or more amino acids selected from the group consisting of histidine, lysine, aspartate, threonine, aromatic phenyl alanine (e.g., phenylalanine, tryptophan, or tyrosine), glycine, glutamine, and leucine. In another embodiment, the metal ion of the metalloprotein is chelated, attached or bound to one or more amino acids selected from the group consisting of histidine, lysine, and aspartate. In one embodiment, the metal ion of the inhibited metalloprotein is chelated, attached or bound to at least two amino acids selected from the group consisting of histidine, lysine, aspartate, threonine, aromatic phenyl alanine (e.g., phenylalanine, tryptophan, or tyrosine), glycine, glutamine, leucine, glutamate, and cysteine. In another embodiment, the metal ion of the metalloprotein is chelated, attached or bound to at least two amino acids selected from the group consisting of histidine, lysine, aspartate, threonine, aromatic phenyl alanine (e.g., phenylalanine, tryptophan, or tyrosine), glycine, glutamine, and leucine. In another embodiment, the metal ion of the metalloprotein is chelated, attached or bound to at least two amino acids selected from the group consisting of histidine, lysine, and aspartate. In one embodiment, the metal ion of the inhibited metalloprotein is chelated, attached or bound to at least three amino acids selected from the group consisting of histidine, lysine, aspartate, threonine, aromatic phenyl alanine (e.g., phenylalanine, tryptophan, or tyrosine), glycine, glutamine, leucine, glutamate, and cysteine. In another embodiment, the metal ion of the metalloprotein is chelated, attached or bound to at least three amino acids selected from the group consisting of histidine, lysine, aspartate, threonine, glutamate, aromatic phenyl alanine (e.g., phenylalanine, tryptophan, or tyrosine), glycine, glutamine, and leucine. In another embodiment, the metal ion of the metalloprotein is chelated, attached or bound to histidine, cysteine, glutamate and aspartate.

In one embodiment, the metal ion of the inhibited metalloprotein is coordinated, attached or bound to one or more amino acids through the heteroatom of the amino acid, namely oxygen, sulfur or nitrogen.

In one embodiment, M is an LpxC metalloprotein. In certain embodiments, the inhibitor I can be bound, chelated or attached to M and results in the reduction of enzymatic activity. In one embodiment, I is bound to the zinc metal ion in the enzyme LpxC. In another embodiment, I is bound to the zinc metal ion in LpxC through one or more bonds originating from the oxygen, nitrogen or sulfur atoms present in the composition of the inhibitor I. In an additional embodiment, inhibitor I is bound to the zinc metal ion in LpxC while inhibitor I is also bound to at least one amino acid residue present in the enzyme through one or more coordinate or hydrogen bonds.

In one embodiment, M has the structure of Formula A-I:

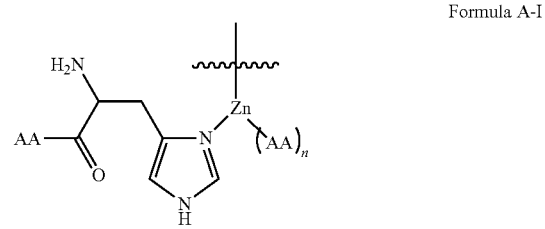

Formula A-I wherein each AA is one or more amino acids; and n is 0, 1, 2, 3 or 4.

In one embodiment, M has the structure of Formula A-II:

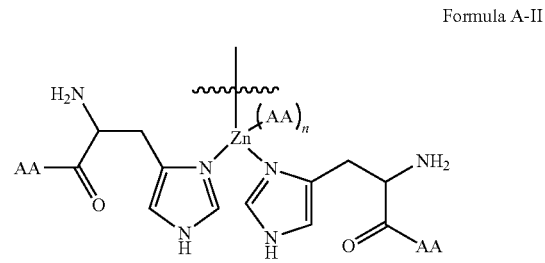

Formula A-II wherein each AA is one or more amino acids; and n is 0, 1, 2 or 3.

In one embodiment, M has the structure of Formula A-III:

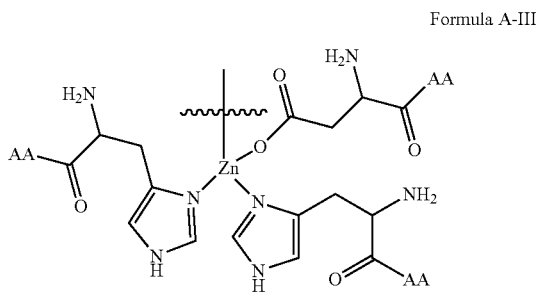

Formula A-III wherein each AA is one or more amino acids.

In one embodiment, a complex of Formula A, A-I, A-II, or A-III resists dissociation due to bonding, chelation or attachment between M and I. In an additional embodiment, a complex Formula A resists dissociation due to the shape of the binding pocket present in the metalloprotein. In another embodiment, a complex of Formula A resists dissociation due to electrostatic interactions present between M and I. In one embodiment, inhibitor I is bound, attached, or chelated to M with one or more bonds. In another embodiment, inhibitor I is bound, attached, or chelated to M with two or more bonds. In one embodiment, inhibitor I is bound, attached, or coordinated to M with one bond. In another embodiment, inhibitor I is bound, attached, or chelated to M with two bonds.

In one embodiment, inhibitor I is a compound of Formula I, Formula II or Formula III, wherein $R_3$ is —OH and Z is O or S. The inhibitor I is bound, attached or chelated to M with one or more coordinate bonds. In one embodiment, inhibitor I is coordinated, attached or chelated to the metal center.

In another embodiment, wherein inhibitor I is a compound of Formula I, Formula II or Formula III, and $R_3$ is OH and Z is O or S, the metalloprotein M is the enzyme LpxC possessing a zinc metal center. One or both of $R_3$ and Z can be optionally bound to the zinc metal center of LpxC, correlating to a decrease in the enzymatic activity of M when compared to that of uninhibited M.

In one embodiment, inhibitor I is a compound of Formula IV, Formula IVA, Formula IVB, Formula V or Formula VI. The inhibitor I is bound, attached or chelated to M with one or more bonds. In one embodiment, the bonds are attached to the metal center.

In one embodiment, wherein inhibitor I is a compound of Formula IV, Formula WA, Formula IVB, Formula V or Formula VI, inhibitor I is bound to M through the non-variable adjacent oxygen atoms present on the substituted heterocyclic ring of any of the compounds of Formulas IV, IVA, IVB, V or VI. In an embodiment in which M is the metalloprotein LpxC, one or both of the non-variable adjacent oxygen atoms present on the substituted heterocyclic ring of any of the compounds of Formulas IV, IVA, IVB, V or VI can be optionally bound to the zinc metal center of LpxC.

In one embodiment, provided herein is a complex of an inhibited enzyme of Formula (B):

Formula (B)

wherein:

M is a metal;

AA is one or more amino acids attached, bound or chelated to M;

Z is O or S;

Y is OH, $NH_2$ or SH; and each R is independently an organic radical, and can connect to form aryl, heteroaryl, cycloalkyl or heterocycle rings.

In another embodiment, provided herein is a complex of an inhibited enzyme of Formula (C):

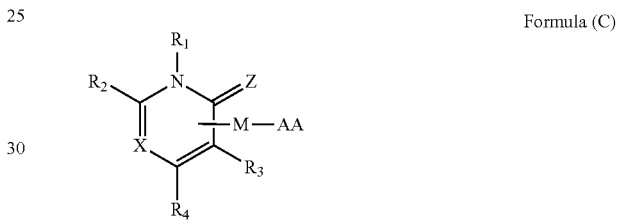

Formula (C)

wherein:

M is a metal;

AA is one or more amino acids attached, bound or chelated to M;

Z is O or S;

X is CH or N $R_1$, $R_2$, $R_3$ and $R_4$ are each independently hydrogen or an organic radical.

In another embodiment, provided herein is a complex of an inhibited enzyme of Formula (D):

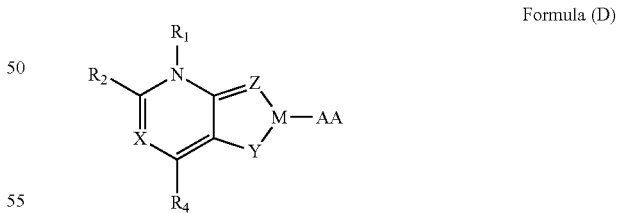

Formula (D)

wherein:

M is a metal;

AA is one or more amino acids attached, bound or chelated to M;

Z is O or S;

X is CH or N

Y is OH, $NH_2$ or SH; and $R_1$, $R_2$ and $R_4$ are each independently hydrogen or an organic radical.

In another embodiment, provided herein is a complex of an inhibited enzyme of Formula (E):

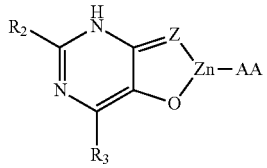

Formula (E)

wherein:

AA is one or more amino acids attached, bound or chelated to the metal zinc;

Z is O or S;

$R_2$ and $R_3$ are each independently hydrogen or an organic radical.

In one embodiment of Formula (E), $R_2$ is H, —$OR^a$, —$N(R^a)_2$, $C_{1-6}$ alkyl, or $C_{1-6}$ alkoxy; wherein $R^a$, is H or $C_{1-6}$ alkyl. In a further embodiment of Formula (E), $R_3$ is a substituted alkyl.

In one embodiment of Formula (E), $R_2$ is either (a) a H or alkyl; or (b) a bivalent radical selected from a bond, —C(=O)—, —(C(=O)O)—, —OC(=O)—, —(C(=O)NR$^c$)—, —N(R$^e$)C(=O)—, —N(R$^c$)—, —S(=O)$_2$—, —(C$_{1-4}$ alkylene)-, —(C$_{1-4}$ alkylene)-O—, —(C$_{1-4}$ alkylene)-N(R$^c$)—, —(C$_{1-4}$ alkylene)-S—, or —(C$_{1-4}$ alkylene)-S(=O)$_2$— ending in a hydrogen atom or an alkyl group.

In another embodiment of Formula (E), $R_3$ is the chain of substituents as follows:

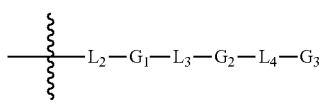

wherein:

$L_2$ is a bivalent radical selected from —(C(R$_4$)(R$_5$))$_n$—(C$_{0-3}$ alkylene)-, —(C(R$_4$)(R$_5$))$_n$—C$_{0-3}$ alkylene)-(C—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-(C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, or —(C(R$_4$)(R$_5$))$_n$—(C$_{0-3}$ alkylene)-N(R$_5$)S(=O)$_2$—;

wherein each $R_4$ is H or optionally substituted $C_{1-6}$ alkyl; and each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —(C$_{0-4}$ alkylene)-OR$^f$, —(C$_{0-4}$ alkylene)-(C$_{1-4}$ alkene), —(C$_{0-4}$ alkylene)-(C$_{1-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, alkylene)-NO$_2$, —(C$_{0-4}$ alkylene)-NR$^f$)$_2$, —(C$_{0-4}$ alkylene)-S(=O)$_2$—(R$^f$), alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$;

wherein each $R^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from —(C$_{2-6}$ alkenylene)- or —(C$_{2-6}$ alkynylene)-;

$L_4$ is a bivalent radical selected from —C(=O)—, —(C(=O)O)—, —(C(=O)NR$^e$)—, —N(R$^e$)C(=O)—, or —(C$_{1-4}$ alkylene)-;

$G_1$ and $G_2$ are each independently, at each occurrence, a bivalent radical selected from —(C$_{6-14}$ arylene)- or -(5- to 14-membered heteroarylene)-;

$G_3$ is H, $C_{3-7}$ cycloalkyl, $C_{3-10}$ heterocycloalkyl, $C_{6-14}$ aryl, 5- to 14-membered heteroarylene, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$R^a$, $R^b$, $R^c$, $R^d$, and $R^e$ are each independently, at each occurrence, H or $C_{1-6}$ alkyl; and n is 1 or 2.

In another embodiment, provided herein is a complex of an inhibited enzyme of Formula (F):

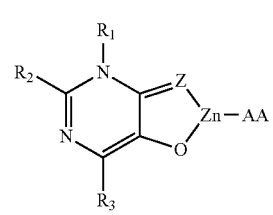

Formula (F)

wherein:

AA is one or more amino acids attached, bound or chelated to the metal zinc;

Z is O or S;

$R_1$, $R_2$ and $R_3$ are each independently hydrogen or an organic radical.

In one embodiment of Formula (F), $R_2$ and $R_3$ are each independently H, —OR$^a$, —N(R$^a$)$_2$, $C_{1-6}$ alkyl, or $C_{1-6}$ alkoxy; wherein $R^a$, is H or $C_{1-6}$ alkyl. In a further embodiment of Formula F, $R_1$ is a substituted alkyl.

In one embodiment of Formula (F), $R_2$ and $R_3$ are each independently either (a) a H or alkyl; or (b) a bivalent radical selected from a bond, —C(=O)—, —(C(=O)O)—, —OC(=O)—, —(C(=O)NR$^c$)—, —NR$^c$)C(=O)—, —S(=O)$_2$—, —(C$_{1-4}$ alkylene)-, —(C$_{1-4}$ alkylene)-O—, —(C$_{1-4}$ alkylene)-N(R$^c$)—, —(C$_{1-4}$ alkylene)-S—, or —(C$_{1-4}$ alkylene)-S(=O)$_2$— ending in a hydrogen atom or an alkyl group.

In another embodiment of Formula (F), $R_1$ is the chain of substituents as follows:

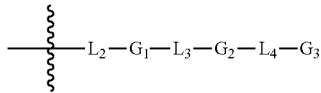

wherein:

$L_2$ is a bivalent radical selected from —$(C(R_4)(R_5))_n$—$(C_{0-3}$ alkylene)-, —$(C(R_4)(R_5))_n$—$C_{0-3}$ alkylene)-(C—$OR^e$)—, —$(C(R_4)(R_5))_n$—$(C_{0-3}$ alkylene)-C(=O)—, —$(C(R_4)(R_5))_n$—$(C_{0-3}$ alkylene)-C(=N—OH)—, —$(C(R_4)(R_5))_n$—$(C_{0-3}$ alkylene)-(C(=O)NR_5)—, —$(C(R_4)(R_5))_n$—$(C_{0-3}$ alkylene)-N($R_5$)C (=O)—, —$(C(R_4)(R_5))_n$—$(C_{0-3}$ alkylene)-O—, —$(C(R_4)(R_5))_n$—$(C_{0-3}$ alkylene)-N($R_5$)—, —$(C(R_4)(R_5))_n$—$(C_{0-3}$ alkylene)-S(=O)$_2$—, —$(C(R_4)(R_5))_n$—$(C_{0-3}$ alkylene)-S(=O)$_2$N($R_5$)—, or —$(C(R_4)(R_5))_n$—$(C_{0-3}$ alkylene)-N($R_5$)S(=O)$_2$—;

wherein each $R_4$ is H or optionally substituted $C_{1-6}$ alkyl; and each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene)$OR^f$, —$(C_{0-4}$ alkylene)-($C_{1-4}$ alkene), —$(C_{0-4}$ alkylene)-($C_{1-4}$ alkyne), $C_2$-$C_7$ heterocycle, —$(C_{0-4}$ alkylene)-C(=O)—($C_1$-$C_6$ alkyl), —$(C_{0-4}$ alkylene)-C(=O)H, —$(C_{0-4}$ alkylene)-C(=O)$OR^f$, —$(C_{0-4}$ alkylene)-CN, —$(C_{0-4}$ alkylene)-halo, —$(C_{0-4}$ alkylene)-NO$_2$, —$(C_{0-4}$ alkylene)-N($R^f$)$_2$, —$(C_{0-4}$ alkylene)-S(=O)$_2$-($R^f$), —$(C_{0-4}$ alkylene)-($C_{6-14}$ aryl), —$(C_{1-4}$ alkylene)-(5- to 14-membered heteroaryl), —$(C_{0-4}$ alkylene)- C(=O)NR$^b$R$^f$ or —$(C_{0-4}$ alkylene)-NR$^b$C(=O)R$^f$;

wherein each $R^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from —$(C_{2-6}$ alkenylene)- or —$(C_{2-6}$ alkynylene)-;

$L_4$ is a bivalent radical selected from —C(=O)—, —(C(=O)O)—, —(C(=O)NR$^e$)—, —N($R^e$)C(=O)—, or —$(C_{1-4}$ alkylene)-;

$G_1$ and $G_2$ are each independently, at each occurrence, a bivalent radical selected from —$(C_{6-14}$ arylene)- or -(5- to 14-membered heteroarylene)-;

$G_3$ is H, $C_{3-7}$ cycloalkyl, $C_{3-10}$ heterocycloalkyl, $C_{6-14}$ aryl, 5- to 14-membered heteroarylene, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$R^a$, $R^b$, $R^c$, $R^d$, and $R^e$ are each independently, at each occurrence, H or $C_{1-6}$ alkyl; and n is 1 or 2.

In another embodiment, provided herein is a complex of an inhibited enzyme of Formula (G):

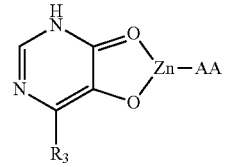

Formula (G)

wherein:

AA is one or more amino acids attached, bound or chelated to the metal zinc;

$R_3$ is the chain of substituents as follows:

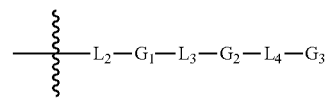

wherein:

$L_2$ is a bivalent radical selected from —$(C(R_4)(R_5))_n$—$C_{0-3}$ alkylene)-, —$(C(R_4)(R_5))_n$—$C_{0-3}$ alkylene)-(C—$OR^c$)—, —$(C(R_4)(R_5))_n$—$C_{0-3}$ alkylene)-C(=O)—, —$(C(R_4)(R_5))_n$—$(C_{0-3}$ alkylene)-C(=N—OH)—, —$(C(R_4)(R_5))_n$—$(C_{0-3}$ alkylene)-(C(=O)NR_5)—, —$(C(R_4)(R_5))_n$—$(C_{0-3}$ alkylene)-N($R_5$)C(=O)—, —$(C(R_4)(R_5))_n$—$(C_{0-3}$ alkylene)-O—, —$(C(R_4)(R_5))_n$—$(C_{0-3}$ alkylene)-N($R_5$)—, —$(C(R_4)(R_5))_n$—$(C_{0-3}$ alkylene)-S(=O)$_2$—, —$(C(R_4)(R_5))_n$—$(C_{0-3}$ alkylene)-S(=O)$_2$N($R_5$)—, or —$(C(R_4)(R_5))_n$—$C_{0-3}$ alkylene)-N($R_5$)S(=O)$_2$—;

wherein each $R_4$ is H or optionally substituted $C_{1-6}$ alkyl; and each $R_5$ is independently H, an optionally substituted $C_{1-6}$ alkyl, an optionally substituted $C_{1-6}$ heteroalkyl, an optionally substituted $C_{1-6}$ alkenyl, an optionally substituted $C_{1-6}$ alkynyl, an optionally substituted $C_{6-14}$ aryl, an optionally substituted 5- to 14-membered heteroaryl, an optionally substituted $C_3$-$C_8$ cycloalkyl, on optionally substituted —$(C_{0-4}$ alkylene)-$OR^f$, —$(C_{0-4}$ alkylene)-($C_{1-4}$ alkene), —$(C_{0-4}$ alkylene)-($C_{1-4}$ alkyne), $C_2$-$C_7$ heterocycle, —$(C_{0-4}$ alkylene)-C(=O)—($C_1$-$C_6$ alkyl), —$(C_{0-4}$ alkylene)-C(=O)H, —$(C_{0-4}$ alkylene)-C(=O)$OR^f$, —$(C_{0-4}$ alkylene)-CN, —$(C_{0-4}$ alkylene)-halo, —$(C_{0-4}$ alkylene)-NO$_2$, —$(C_{0-4}$ alkylene)-N($R^f$)$_2$, —$(C_{0-4}$ alkylene)-S(=O)$_2$-($R^f$), —$(C_{0-4}$ alkylene)-($C_{6-14}$ aryl), —$(C_{1-4}$ alkylene)-(5- to 14-membered heteroaryl), —$(C_{0-4}$ alkylene)- C(=O)NR$^b$R$^f$ or —$(C_{0-4}$ alkylene)-NR$^b$C(=O)R$^f$;

wherein each $R^f$ is independently H, an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$L_3$ is a bivalent radical selected from —$(C_{2-6}$ alkenylene)- or —$(C_{2-6}$ alkynylene)-;

$L_4$ is a bivalent radical selected from —C(=O)—, —(C(=O)O)—, —(C(=O)NR$^e$)—, —N($R^e$)C(=O)—, or —$(C_{1-4}$ alkylene)-;

G₁ and G₂ are each independently, at each occurrence, a bivalent radical selected from —($C_{6-14}$ arylene)- or -(5- to 14-membered heteroarylene)-;

G₃ is H, $C_{3-7}$ cycloalkyl, $C_{3-10}$ heterocycloalkyl, $C_{6-14}$ aryl, 5- to 14-membered heteroarylene, ($C_{1-4}$ alkylene)-($C_{1-4}$ heteroalkyl), ($C_{3-10}$ heterocycloalkylene)-($C_{1-4}$ alkyl), ($C_{3-10}$ heterocycloalkylene)-($C_{1-4}$ heteroalkyl), an optionally substituted alkyl, an optionally substituted heteroalkyl, an optionally substituted alkenyl, an optionally substituted alkynyl, an optionally substituted cycloalkyl, an optionally substituted heterocyclyl, an optionally substituted aryl, an optionally substituted heteroaryl or an optionally substituted alkoxy;

$R^a$, $R^b$, $R^c$, $R^d$, and $R^e$ are each independently, at each occurrence, H or $C_{1-6}$ alkyl; and n is 1 or 2.

Kits and Devices

The disclosure provides a variety of kits for conveniently and effectively carrying out methods of the present disclosure. Typically kits will comprise sufficient amounts and components to allow a user to perform multiple treatments of a subj ect(s) or to perform multiple experiments. In another embodiment, the kit may contain a compound of Formula I, a compound of Formula II, a compound of Formula III, a compound of Formula IV, a compound of Formula V, or a compound of Formula VI.

In additional embodiments, pharmaceutical kits are provided. The kit includes a sealed container approved for the storage of pharmaceutical compositions, the container containing one of the above-described pharmaceutical compositions. In some embodiments, the sealed container minimizes the contact of air with the ingredients, e.g. an airless bottle. In other embodiments, the sealed container is a sealed tube. An instruction for the use of the composition and the information about the composition are to be included in the kit.

The present disclosure provides for devices which may incorporate compounds of the present disclosure. These devices contain in a stable formulation available to be immediately delivered to a subject in need thereof, such as a human patient.

It will be appreciated that the following examples are intended to illustrate but not to limit the present disclosure. Various other examples and modifications of the foregoing description and examples will be apparent to a person skilled in the art after reading the disclosure without departing from the spirit and scope of the disclosure, and it is intended that all such examples or modifications be included within the scope of the appended claims. All publications and patents referenced herein are hereby incorporated by reference in their entirety.

EXAMPLES

Example 1

Synthesis of Compounds or Metalloprotein Modulators

The compounds, metalloprotein modulators or metalloprotein inhibitors of the present disclosure may be synthesized with standard synthetic methods. Those skilled in the art of organic synthesis will recognize various synthetic methodologies that may be used to prepare compounds or metalloprotein modulators of the present disclosure.

Unless otherwise noted, starting materials were purchased from commercial suppliers (e.g., Sigma-Aldrich, Chem-Bridge, and Acros Organics) and were used without further purification. All commercial materials were listed as 95% purity or greater. The purity of all synthesized compounds was determined to be ≥95% by either elemental analysis or HPLC. Flash silica gel chromatography was performed using silica gel 40-63 μm mesh. $^1$H and $^{13}$C NMR spectra were recorded on one of several Varian FT-NMR spectrometers, In the discussion above and in the examples below, the following abbreviations have the following meanings. If an abbreviation is not defined, it has its generally accepted meaning.

DIAD=diisopropyl azocarboxylate
DMF=dimethylformamide
DMA=dimethylacetamide
DMAP=dimethylaminopyridine
DMSO=dimethyl sulfoxide
MeTHF=2-methyltetrahydrofuran
HATU=1-[Bis(dimethylamino)methylene]-1H-1,2,3-triazolo[4,5-b]pyridinium 3-oxid hexafluorophosphate)
DIPEA=N,N-Diisopropylethylamine
CBZ=benzyloxycarbonyl
DCC=1,3-dicyclohexylcarbodiimide
EtOAc=ethyl acetate
EtO=ethoxy
MeOH=methanol
DCM=dichloromethane
HCl =hydrochloric acid
ACN=acetonitrile
LDA=lithium diisopropylamide
mCPBA=meta-chloroperbenzoic acid
MTBE=methyl tert butyl ether
CDMT=2-chloro-4,6-dimethoxy-1,3,5-triazine
TMS=trimethyl silyl
DME=dimethyl ether
IPA=isopropanol
$Et_2O$=diethyl ether
DEAD=diethyl azodicarboxylate
LiHMDS=lithium hexamethyldisilazide/lithium bis(trimethylsilyl)amide
Aq.=aqueous
bm=broad multiplet
BOC=tert-butoxycarbonyl
bd=broad doublet
bs=broad singlet
d=doublet
dd=doublet of doublets
dq=doublet of quartets
dt=doublet of triplets
eq.=equivalents
g=grams
h=hours
HPLC=high pressure liquid chromatography
UPLC=ultra performance liquid chromatography
m=multiplet
M=molar
M %=mole percent
max=maximum
meq=milliequivalent
mg=milligram
mL=milliliter
mm=millimeter
mmol=millimol
q=quartet
s=singlet
t or tr=triplet
TBS=tert-butyldimethylsilyl TFA=trifluoroacetic acid
THF=tetrahydrofuran
TLC=thin layer chromatography
p-TLC=preparative thin layer chromatography
μL=microliter
N=normality
MS=mass spectrometry
rt=room temperature
Ac=acetate
NMP=1-methyl-2-pyrrolidinone
μL=microliter
J=coupling constant
NMR=nuclear magnetic resonance
MHz=megahertz
Hz=hertz
m/z=mass to charge ratio
min=minutes
ppt=precipitate
sat.=saturated Synthesis of Compounds 82, 83, 84, and 85

The synthetic scheme to prepare compounds 82, 83, 84 and 85 is shown in FIG. 1.

Synthesis of ethyl 5-(benzyloxy)-1-(2-(4-bromophenyl)-2-oxoethyl)-2-methyl-6-oxo-1,6-dihydro pyrimidine-4-carboxylate, 10

To a solution of ethyl 5-(benzyloxy)-2-methyl-6-oxo-1,6-dihydropyrimidine-4-carboxylate, 3 (2 g, 0.0069 mol) dissolved in DMF (20mL) was added $K_2CO_3$ (1.2 g, 0.009 mol) and 4-bromophenacyl bromide, 9 (1.9 g, 0.0069 mol) and stirred at 25° C., for 1h. After completion of the reaction, DMF was removed under reduced pressure, the crude product was diluted with water and EtOAc. The layers were separated, the aqueous layer was extracted with EtOAc and the combined organic layers were washed with brine solution and dried over anhydrous $Na_2SO_4$, filtered and concentrated. The crude product was triturated with cold methanol to get 1.3 g (40.6%) of pure ethyl 5-(benzyloxy)-1-(2-(4-bromophenyl)-2-oxoethyl)-2-methyl-6-oxo-1,6-dihydropyrimidine-4-carboxylate, 10. UPLC=Calculated for $C_{23}H_{21}BrN_2O_5$ 485.33, Observed=487.2.

Synthesis of ethyl 1-(2-([1,1'-biphenyl]-4-yl)-2-oxoethyl)-5-(benzyloxy)-2-methyl-6-oxo-1,6-dihydropyrimidine-4-carboxylate, 11

To a solution of 5-(benzyloxy)-1-(2-(4-bromophenyl)-2-oxoethyl)-2-methyl-6-oxo-1,6-dihydro pyrimidine-4-carboxylate, 10 (0.3 g, 0.00063 mol) in toluene (15 mL), phenyl boronic acid (0.23 g, 0.0018 mol), $K_2CO_3$ (0.17 g, 0.00126 mol) and water (3 mL) were added and degassed the reaction mixture under nitrogen for 10 min. To this purged reaction mixture $PdCl_2(PPh_3)_4$ (0.036 g, 0.0000315 mol) was added and heated the reaction mixture to 100° C. for 3 h. After completion of the reaction, reaction mixture was cooled, diluted with EtOAc and washed with water and brine solution. The organic layer was dried over anhydrous $Na_2SO_4$, filtered and concentrated under reduced pressure. The crude product was purified by column chromatography to get 0.25 g (83%) of pure ethyl 1-(2-([1,1'-biphenyl]-4-yl)-2-oxoethyl)-5-(benzyloxy)-2-methyl-6-oxo-1,6-dihydropyrimidine-4-carboxylate, 11. UPLC=Calculated for $C_{29}H_{26}N_2O_5$ 482.54, Observed=483.2.

Synthesis of ethyl 1-(2-(11,1'-biphenyl1-4-yl)-2-hydroxyethyl)-5-hydroxy-2-methyl-6-oxo-1,6-dihydropyrimidine-4-carboxylate, 67 and ethyl 1-(2-(11,1'-biphenyl1-4-yl)-2-oxoethyl)-5-hydroxy-2-methyl-6-oxo-1,6-dihydropyrimidine-4-carboxylate, 84

1-(2-([1,1'-biphenyl]-4-yl)-2-oxoethyl)-5-(benzyloxy)-2-methyl-6-oxo-1,6-dihydropyrimidine-4-carboxylate (0.25 g, 0.000621 mol) was dissolved in 1:1 methanol (3 mL) and THF (3 mL). To this 10% Palladium on carbon (25 mg) was added and hydrogenated at 1 atm $H_2$ pressure for 2 h at 25° C. After completion of the reaction, the reaction mixture was filtered on celite bed and the filtrate was concentered to get 0.16 g of crude product which was purified by prep HPLC purification to get 0.05 g of pure ethyl 1-(2-([1,1'-biphenyl]-4-yl)-2-hydroxyethyl)-5-hydroxy-2-methyl-6-oxo-1,6-dihydro pyrimidine-4-carboxylate, compound 67, and 0.048 g of ethyl 1-(2-([1,1'-biphenyl]-4-yl)-2-oxoethyl)-5-hydroxy-2-methyl-6-oxo-1,6-dihydropyrimidine-4-carboxylate, compound 84.

Compound 85 UPLC=Calculated for $C_{22}H_{22}N_2O_5$: 394.43, Observed=395.2

Compound 84 UPLC =Calculated for $C_{22}H_{20}N_2O_5$: 392.41, Observed=393.2

Synthesis of 1-(2-(11,1'-biphenyl1-4-yl)-2-hydroxyethyl)-5-hydroxy-2-methyl-6-oxo-1,6-dihydro pyrimidine-4-carboxylic acid, 83

Ethyl 1-(2-([1,1'-biphenyl]-4-yl)-2-hydroxyethyl)-5-hydroxy-2-methyl-6-oxo-1,6-dihydropyrimidine-4-carboxylate, 67 (0.04 g, 0.0001 mol) was dissolved in THF (2 mL) and water (2 mL). To this NaOH (0.012 g, 0.0003 mol) was added and stirred at 25° C. for 12 h. After completion of the reaction, THF was removed under reduced pressure, the aqueous layer was acidified to pH 5 and stirred for 10 min. The solid precipitate was filtered and washed with water and diethylether and dried to get 0.019 g (52.7%) of pure 1-(2-([1,1'-biphenyl]-4-yl)-2-hydroxyethyl)-5-hydroxy-2-methyl-6-oxo-1,6-dihydro pyrimidine-4-carboxylic acid compound 83. LCMS=Calculated for $C_{20}H_{18}N_2O_5$: 366.37, Observed=367.2

Synthesis of 1-(2-(11,1'-biphenyl1-4-yl)-2-oxoethyl)-5-hydroxy-2-methyl-6-oxo-1,6-dihydro pyrimidine-4-carboxylic acid , 82

Ethyl 1-(2-([1,1'-biphenyl]-4-yl)-2-oxoethyl)-5-hydroxy-2-methyl-6-oxo-1,6-dihydropyrimidine-4-carboxylate, 66 (0.04 g, 0.0001 mol) was dissolved in THF (2 mL) and water (2 mL). To this NaOH (0.012 g, 0.0003 mol) was added and stirred at 25° C. for 12 h. After completion of the reaction, THF was removed under reduced pressure, the aqueous layer was acidified to pH 5 and stirred for 10 min. The solid precipitate was filtered and washed with water and diethylether and dried to get 0.025 g (67.5%) of pure 1-(2-([1,1'-biphenyl]-4-yl)-2-oxoethyl)-5-hydroxy-2-methyl-6-oxo-1,6-dihydro pyrimidine-4-carboxylic acid, compound 82. LCMS=Calculated for $C_{20}H_{16}N_2O_5$: 364.36, Observed=365.2

Synthesis of Compound 91.

Figure 2:
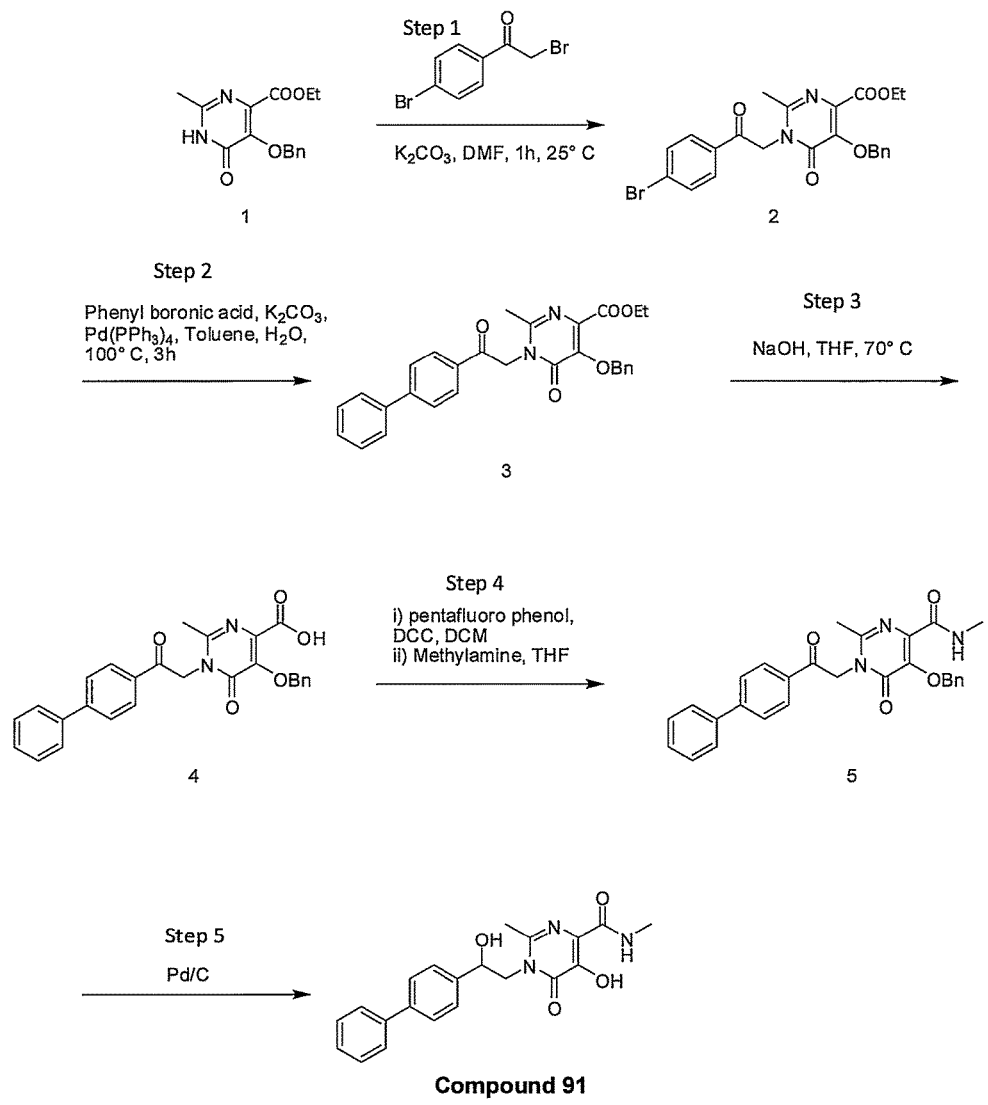
FIG. 2 shows a synthetic scheme to prepare compound 91.

The synthetic scheme to prepare compound 91 is shown in FIG. 2.

Step 1: Synthesis of ethyl 5-(benzyloxy)-1-(2-(4-bromophenyl)-2-oxoethyl)-2-methyl-6-oxo-1,6-dihydropyrimidine-4-carboxylate, 2

To a stirred solution of ethyl 5-(benzyloxy)-2-methyl-6-oxo-1,6-dihydropyrimidine-4-carboxylate, 1 (2 g, 0.0069 mol) in DMF (20 mL), $K_2CO_3$ (1.24 g, 0.009 mol) was added and stirred for 5 min at 25° C. Then, 4-Bromophenacyl bromide (2.01 g, 0.0072 mol) was added and stirred at 25° C. for 1 h. After completion of the reaction, DMF was removed under reduced pressure, the crude product was diluted with water and EtOAc. The layers were separated, the aqueous layer was extracted with EtOAc and the combined organic layers were washed with brine solution and dried over anhydrous $Na_2SO_4$, filtered and concentrated. It was purified by flash column chromatography on silica gel with gradient elution of 20-25% EtOAc in pet ether to get 1.2 g (35.92%) of ethyl 5-(benzyloxy)-1-(2-(4-bromophenyl)-2-oxoethyl)-2-methyl-6-oxo-1,6-dihydropyrimidine-4-carboxylate, 2. LCMS =Calculated for $C_{23}H_{21}BrN_2O_5$: 485.33, Observed=486.0.

Step 2: Synthesis of ethyl 1-(2-(11,1'-biphenyl1-4-yl)-2-oxoethyl)-5-(benzyloxy)-2-methyl-6-oxo-1,6-dihydropyrimidine-4-carboxylate, 3

To a stirred solution of ethyl 5-(benzyloxy)-1-(2-(4-bromophenyl)-2-oxoethyl)-2-methyl-6-oxo-1,6-dihydropyrimidine-4-carboxylate, 2 (400 mg, 0.824 mmol) in toluene (5 mL), phenyl boronic acid (150 mg, 1.23 mmol), $K_2CO_3$ (227 mg, 1.648 mmol), water (0.4 mL) were added and degassed for 15 min. Then, $PdCl_2(PPh_3)_4$ (47 mg, 0.00412 mmol) was added and again degassed for 5 min. The contents were heated to 100° C. for 3 h. After completion of the reaction, the reaction mixture was concentrated and the residue was diluted by water and extracted with EtOAc. The separated organic layer was washed with brine, dried over sodium sulfate and concentrated in vacuo. The crude product was purified by flash column chromatography on silica gel with gradient elution of 40-45% EtOAc in pet ether to get 280 mg (70.52%) of ethyl 1-(2-([1,1'-biphenyl]-4-yl)-2-oxoethyl)-5-(benzyloxy)-2-methyl-6-oxo-1,6-dihydropyrimidine-4-carboxylate, 3. LCMS =Calculated for $C_{29}H_{26}N_2O_5$: 482.54, Observed=483.1.

Step 3: Synthesis of 1-(2-(11,1'-biphenyl1-4-yl)-2-oxoethyl)-5-(benzyloxy)-2-methyl-6-oxo-1,6-dihydropyrimidine-4-carboxylic acid, 4

To a stirred solution of ethyl 1-(2-([1,1'-biphenyl]-4-yl)-2-oxoethyl)-5-(benzyloxy)-2-methyl-6-oxo-1,6-dihydropyrimidine-4-carboxylate, 3 (250 mg, 0.518 mmol) in THF (5 mL), sodium hydroxide (62 mg, 1.55 mmol) and water (1 mL) were added and refluxed at 70° C. for 3 h. After completion of reaction the reaction mixture was concentrated and diluted with water. It was acidified (pH=5) with 1.5N HCl to get the precipitate which was filtered, dried to obtain 170 mg (72.35%) of 1-(2-([1,1'-biphenyl]-4-yl)-2-oxoethyl)-5-(benzyloxy)-2-methyl-6-oxo-1,6-dihydropyrimidine-4-carboxylic acid, 4. LCMS=Calculated for $C_{27}H_{22}N_2O_5$ 454.48, Observed =455.0.

Step 4: Synthesis of 1-(2-(11,1'-biphenyl1-4-yl)-2-oxoethyl)-5-(benzyloxy)-N,2-dimethyl-6-oxo-1,6-dihydropyrimidine-4-carboxamide, 5

To a stirred solution of 1-(2-([1,1'-biphenyl]-4-yl)-2-oxoethyl)-5-(benzyloxy)-2-methyl-6-oxo-1,6-dihydropyrimidine-4-carboxylic acid, 4 (170 mg, 0.374 mmol) in DCM (4 mL), pentafluoro phenol (68 mg, 0.374 mmol), DCC (115 mg, 0.561 mmol) were added and stirred at 25° C. for 1 h. Methylamine in THF (1 mL) was then added and stirred at 25° C. for 2 h. After completion of reaction, the reaction mixture was concentrated to get the crude product which was purified by flash column chromatography on silica gel with gradient elution of 3% methanol in dichloromethane to obtain 100 mg (57.47%) of 1-(2-([1,1'-biphenyl]-4-yl)-2-oxoethyl)-5-(benzyloxy)-N,2-dimethyl-6-oxo-1,6-dihydropyrimidine-4-carboxamide, 5. UPLC =Calculated for $C_{28}H_{25}N_3O_4$: 467.53, Observed =468.3.

Step 5: Synthesis of 1-(2-(11,1'-biphenyl1-4-yl)-2-hydroxyethyl)-5-hydroxy-N,2-dimethyl-6-oxo-1,6-dihydropyrimidine-4-carboxamide, 91

To a stirred solution of 1-(2-([1,1'-biphenyl]-4-yl)-2-oxoethyl)-5-(benzyloxy)-N,2-dimethyl-6-oxo-1,6-dihydropyrimidine-4-carboxamide, 5 (100 mg, 0.213 mmol) in methanol: THF(1:1=3m1), Pd/C (25 mg) was added and stirred at 25° C. for 5 h under $H_2$ balloon pressure (15 psi). After completion of reaction by UPLC, it was filtered through celite bed using 50% methanol in dichloromethane and concentrated in vacuo. It was purified by trituration with acetonitrile, THF and finally methanol wash to obtain 30 mg (37.5%) of pure 1-(2-([1,1'-biphenyl]-4-yl)-2-hydroxyethyl)-5-hydroxy-N,2-dimethyl-6-oxo-1,6-dihydro pyrimidine-4-carboxamide, compound 91. LCMS=Calculated for $C_{21}H_{21}N_3O_4$: 379.42, Observed=380.3.

Synthesis of Compound 95.

Figure 3:
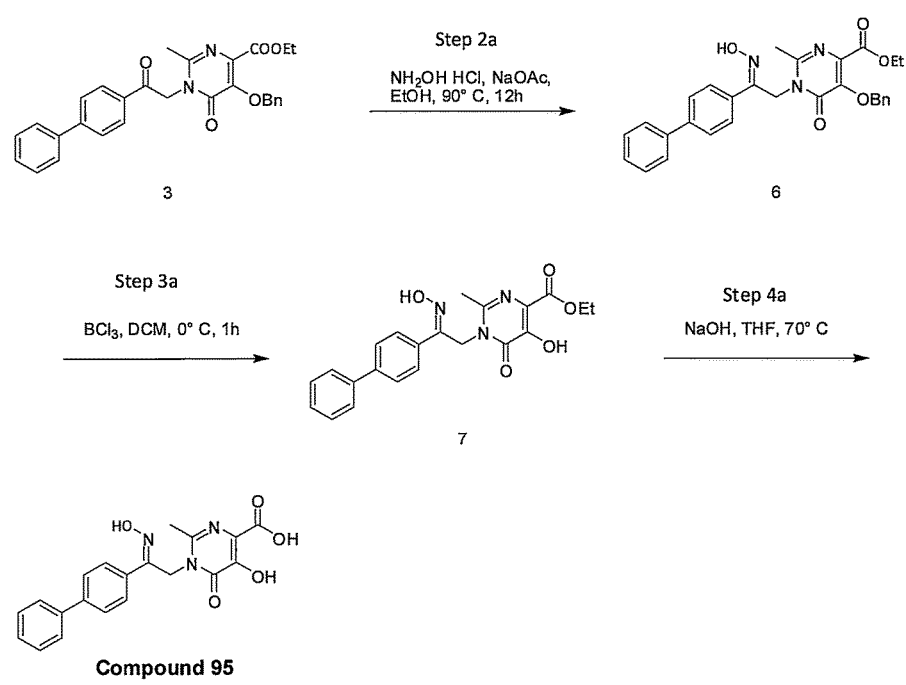
FIG. 3 shows a synthetic scheme to prepare compound 95.

The synthetic scheme to prepare compound 95 is shown in FIG. 3.

Step 2a: Synthesis of ethyl (E)-1-(2-(11,1'-biphenyl1-4-yl)-2-(hydroxyimino)ethyl)-5-(benzyloxy)-2-methyl-6-oxo-1,6-dihydropyrimidine-4-carboxylate, 6

To a stirred solution of ethyl 1-(2-([1,1'-biphenyl]-4-yl)-2-oxoethyl)-5-(benzyloxy)-2-methyl-6-oxo-1,6-dihydropyrimidine-4-carboxylate, 3 (300 mg, 0.622 mmol) in ethanol (8 mL), hydroxylamine hydrochloride (86 mg, 1.244 mmol), sodium acetate (102 mg, 1.244 mmol) were added and refluxed at 90° C. for 12 h. After completion of reaction, the solvent was removed under reduced pressure, the crude product was diluted with water and EtOAc. The layers were separated, the aqueous layer was extracted with EtOAc, and the combined organic layers were washed with brine solution and dried over anhydrous $Na_2SO_4$, filtered and concentrated to obtain 270 mg (87.37%) of ethyl (E)-1-(2-([1,1'-biphenyl]-4-yl)-2-(hydroxyimino)ethyl)-5-(benzyloxy)-2-methyl-6-oxo-1,6-dihydro pyrimidine-4-carboxylate, 6. UPLC=Calculated for $C_{29}H_{27}N_3O_5$: 497.55, Observed=498.3.

Step 3a: Synthesis of ethyl (E)-1-(2-(11,1'-biphenyl1-4-yl)-2-(hydroxyimino)ethyl)-5-hydroxy-2-methyl-6-oxo-1,6-dihydropyrimidine-4-carboxylate, 7

To a stirred solution of (E)-1-(2-([1,1'-biphenyl]-4-yl)-2-(hydroxyimino)ethyl)-5-(benzyloxy)-2-methyl-6-oxo-1,6-dihydro pyrimidine-4-carboxylate, 6 (270 mg, 0.543 mmol) in dichloromethane (6 mL), cooled to 0° C., boron trichloride (0.5 mL) was added and stirred at 25° C. for 1 h. After completion of the reaction the reaction mixture was quenched by methanol and concentrated in vacuo to obtain 100 mg (45.24%) of ethyl (E)-1-(2-([1,1'-biphenyl]-4-yl)-2-(hydroxyimino)ethyl)-5-hydroxy-2-methyl-6-oxo-1,6-dihydropyrimidine-4-carboxylate, 7. UPLC=Calculated for $C_{22}H_{21}N_3O_5$: 407.43, Observed=408.2.

Step 4a: Synthesis of (E)-1-(2-(11,1'-biphenyl1-4-yl)-2-(hydroxyimino)ethyl)-5-hydroxy-2-methyl-6-oxo-1,6-dihydropyrimidine-4-carboxylic acid, 95

To a stirred solution of ethyl (E)-1-(2-([1,1'-biphenyl]-4-yl)-2-(hydroxyimino)ethyl)-5-hydroxy-2-methyl-6-oxo-1,6-dihydropyrimidine-4-carboxylate, 7 (100 mg, 0.245 mmol) in THF (3 mL), sodium hydroxide (19 mg, 0.491 mmol) was added and refluxed at 70° C. for 3 h. After completion of reaction the reaction mixture was concentrated and diluted with water and quenched by 1.5 N HCl to get solid precipitate. The precipitate was filtered and purified by preparative HPLC to obtain (E)-1-(2-([1,1'-biphenyl]-4-yl)-2-(hydroxyimino)ethyl)-5-hydroxy-2-methyl-6-oxo-1,6-dihydropyrimidine-4-carboxylic acid, compound 95. LCMS =Calculated for $C_{20}H_{17}N_3O_5$: 379.37, Observed=380.0.

Synthesis of Compound 70

Figure 4:
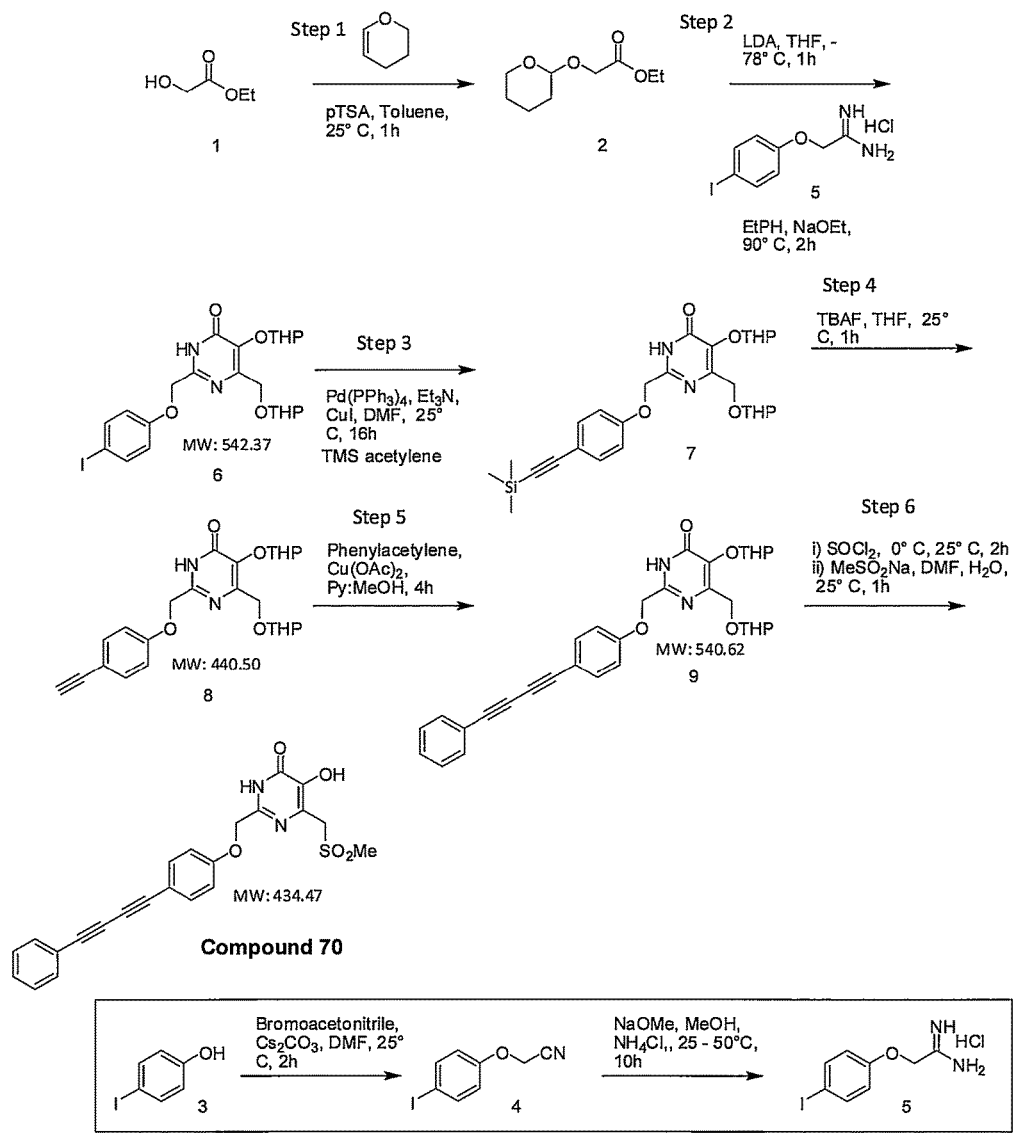
FIG. 4 shows a synthetic scheme to prepare compound 70.

The synthetic scheme to prepare compound 70 is shown in FIG. 4.

Synthesis of ethyl 2-((tetrahydro-2H-pyran-2-yl)oxy)acetate, 2:

To a solution of ethyl glycolate (10 g, 0.0961 mol) in toluene (100 mL) was added 3,4-dihydro-2H-pyran (8 g, 0.0961 mol) followed by catalytic amount of pTSA (30 mg) and stirred at 25° C. for 1 h. After completion of the reaction, the reaction mixture was washed with water and brine solution. The organic layer was dried over anhydrous $Na_2SO_4$, filtered and concentrated under reduced pressure to get 18 g (99%) ethyl 2-((tetrahydro-2H-pyran-2-yl)oxy) acetate, 2, as colorless liquid.

Synthesis of 2-(4-iodophenoxy)acetonitrile, 4

To a slurry of $Cs_2CO_3$ (11.1 g, 0.034 mol) and 4-iodophenol, 3 (5 g, 0.0227 mol) in DMF (50 mL), bromoacetonitrile (3.27 g, 0.0272 mol) was added and stirred at 25° C. for 2 h. After completion of the reaction, the reaction mixture was filtered and concentrated under reduced pressure. The crude product was dissolved in EtOAc and washed with water and brine solution. The organic layer was dried over anhydrous $Na_2SO_4$, filtered and concentrated to get 5.6 g (98%) of pure 2-(4-iodophenoxy)acetonitrile, 4, as an off white solid. LCMS=Calculated for $C_8H_6INO$: 259.05, Observed=257.9.

Synthesis of 2-(4-iodophenoxy)acetimidamide hydrochloride, 5

To a solution of 2-(4-iodophenoxy)acetonitrile, 4 (4.2 g, 0.0162mol) in methanol (40 mL), NaOMe(25% in MeOH, 3.4 mL, 0.0161 mol) was added at 25° C. and stirred for 6 h. After completion of the reaction, NHCl (0.95 g, 0.0177 mol) was added to the reaction mixture and heated to 50° C. for 4 h. After completion of the reaction, methanol was removed under reduced pressure. The crude product was washed with diethylether and dried to get 4.6 g (92%) of pure 2-(4-iodophenoxy)acetimidamide hydrochloride, 5 as an off white solid. LCMS=Calculated for $C_8H_{10}ClN_2O$: 312.54, Observed=276.8.

Synthesis of 2-((4-iodophenoxy)methyl)-5-((tetrahydro-2H-pyran-2-yl)oxy)-6-(((tetrahydro-2H-pyran-2-yl)oxy)methyl)pyrimidin-4(3H)-one, 6

To a cooled solution of ethyl 2-((tetrahydro-2H-pyran-2-yl)oxy)acetate, 2 (2 g, 0.0106 mol) in diethyl ether (20 mL), LDA (1M in THF, 6.3 mL, 0.0063 mmol) was added slowly at −78° C. and allowed to stir at 25° C. for 1 h. After completion of the reaction, reaction mixture was quenched with saturated $NH_4Cl$ and reaction mixture was diluted with EtOAc and water. The layers were separated and aqueous layer was extracted with EtOAc, combined organic layers were washed with brine solution. The organic layer was dried over anhydrous $Na_2SO_4$, filtered and concentrated under reduced pressure. The crude product was dissolved in ethanol. To this mixture 2-(4-iodophenoxy)acetimidamide hydrochloride, 5 (6.6 g, 0.021 mol) and NaOEt (21% in ethanol, 6.8 mL, 0.021 mol) were added and heated to reflux for 2 h. After completion of the reaction, solvent was removed under reduced pressure. The crude product was dissolved in EtOAc and washed with water and brine solution. The organic layer was dried over anhydrous $Na_2SO_4$, filtered and concentrated. The crude product was purified by column chromatography using dichloromethane and 1-8% of methanol and to get 1.2 g (20.8%) pure 2-((4-iodophenoxy)methyl)-5-((tetrahydro-2H-pyran-2-yl) oxy)-6-(((tetrahydro-2H-pyran-2-yl)oxy)methyl) pyrimidin-4(3H)-one, 6 as an off white solid. UPLC=Calculated for $C_{22}H_{27}IN_2O_6$: 542.37, Observed=543.2.

Synthesis of 5-((tetrahydro-2H-pyran-2-yl)oxy)-6-(((tetrahydro-2H-pyran-2-yl)oxy)methyl)-2-((4-((trimethylsilyl)ethynyl)phenoxy)methyl)pyrimidin-4(3H)-one, 7

To a solution of 2-((4-iodophenoxy)methyl)-5-((tetrahydro-2H-pyran-2-yl)oxy)-6-(((tetrahydro-2H-pyran-2-yl) oxy)methyl)pyrimidin-4(3H)-one, 6 (0.5 g, 0.00092 mol) in DMF (5 mL). Triethylamine (0.27 g, 0.00276 mol), CuI (0.017 g, 0.000092 mol) and $PdCl_2(PPh_3)_4$ (0.053 g, 0.000046 mol) were added and degassed the reaction mixture under nitrogen for 10 min. To this reaction mixture, trimethylsilyl acetylene (0.45 g, 0.0046 mol) was added and stirred the reaction mixture at 25° C. for 16 h. After completion of the reaction, solvent was removed under reduced pressure. The crude product was dissolved in EtOAc and washed with water and brine solution. The organic layer was dried over anhydrous $Na_2SO_4$, filtered and concentrated. The crude product was purified by column chromatography using dichloromethane and 1-8% of methanol and to get 0.2 g (42%) pure 5-((tetrahydro-2H-pyran-2-yl)oxy)-6-(((tetrahydro-2H-pyran-2-yl)oxy)methyl)-2-((4-((trimethylsilyl) ethynyl)phenoxy)methyl)pyrimidin-4(3H)-one, 7 as a brown solid. UPLC=Calculated for $C_{27}H_{36}N_2O_6Si$: 512.68, Observed=513.4.

Synthesis of 2-((4-ethynylphenoxy)methyl)-5-((tetrahydro-2H-pyran-2-yl)oxy)-6-(((tetrahydro-2H-pyran-2-yl)oxy)methyl)pyrimidin-4(3H)-one, 8

To solution of 5-((tetrahydro-2H-pyran-2-yl)oxy)-6-(((tetrahydro-2H-pyran-2-yl)oxy)methyl)-1)oxy)methyl)-244-((trimethylsilyl)ethynyl)phenoxy)methyl)pyrimidin-4 (3H)-one, 7 (0.2 g, 0.00039 mol) in THF (5mL), TBAF (2M in THF, 0.39 mL, 0.00078 mol) was added and stirred at 25° C. for 1 h. After completion of the reaction, reaction mixture was diluted with water and EtOAc. The layers were separated and organic layer was washed with brine solution and dried over anhydrous $Na_2SO_4$, filtered and concentrated to get 0.17 g (99%) of 24(4-ethynylphenoxy)methyl)-5-((tetrahydro-2H-pyran-2-yl)oxy)-6-(((tetrahydro-2H-pyran-2-yl)oxy)methyl)pyrimidin-4(3H)-one, 8. This crude product was directly taken for next step without purification. UPLC=Calculated for $C_{24}H_{28}N_2O_6$: 440.50, Observed=441.4.

Synthesis of 2-((4-(phenylbuta-1,3-diyn-1-yl)phenoxy)methyl)-5-((tetrahydro-2H-pyran-2-yl)oxy)-6-(((tetrahydro-2H-pyran-2-yl)oxy)methyl)pyrimidin-4(3H)-one, 9

To a solution of 244-ethynylphenoxy)methyl)-5-((tetrahydro-2H-pyran-2-yl)oxy)-6-(((tetrahydro-2H-pyran-2-yl)oxy)methyl)pyrimidin-4(3H)-one, 8 (0.17 g, 0.000386 mol) in methanol (3mL) and pyridine(3 mL) was added phenyl acetylene(0.11 g, 0.0011 mol) followed by $Cu(OAc)_2$ (0.14 g, 0.00077 mol) and stirred at 25° C. for 4 h. After completion of the reaction, solvent was removed under reduced pressure and the crude product was dissolved in with EtOAc and washed with water and brine solution. The organic layer was dried over anhydrous $Na_2SO_4$, filtered and concentrated. The crude product was purified by column chromatography to get 0.13 g (65%) of pure 2-((4-(phenylbuta-1,3-diyn-1-yl)phenoxy)methyl)-5-((tetrahydro-2H-pyran-2-yl)oxy)-6-(((tetrahydro-2H-pyran-2-yl)oxy) methyl)pyrimidin-4(3H)-one, 9. UPLC=Calculated for $C_{32}H_{32}N_2O_6$: 540.62, Observed=541.4.

Synthesis of 5-hydroxy-6-((methylsulfonyl)methyl)-2-((4-(phenylbuta-1,3-diyn-1-yl)phenoxy) methyl) pyrimidin-4(3H)-one, 70

To a cooled solution of 2-((4-(phenylbuta-1,3-diyn-1-yl) phenoxy)methyl)-5-((tetrahydro-2H-pyran-2-yl)oxy)-6-(((tetrahydro-2H-pyran-2-yl)oxy)methyl)pyrimidin-4(3H)-one, 9 (0.13 g, 0.00024 mol) in DCM (5 mL) $SOCl_2$ (5 mL) was added at 0° C. and allowed to stir at 25° C. for 2 h. After completion of the reaction, volatiles were removed under reduced pressure. To this crude product sodium methyl sulfinate was added followed by DMF (3mL): water (3mL), and the mixture was stirred at 25° C. for 1 h. After completion of the reaction, excess water was added to the reaction mixture and stirred for 10 min. The obtained solid was filtered and washed with more water and dried. The crude solid was washed with DCM and 5% methanol to get 0.02g (20%) pure 5-hydroxy-6-((methylsulfonyl)methyl)-2-((4-(phenylbuta-1,3-diyn-1-yl)phenoxy)methyl)pyrimidin-4 (3H)-one, compound 70 as an off white solid. UPLC=Calculated for $C_{23}H_{18}N_2O_5S$: 434.47, Observed=435.2.

Synthesis of Compound 71

Figure 5:
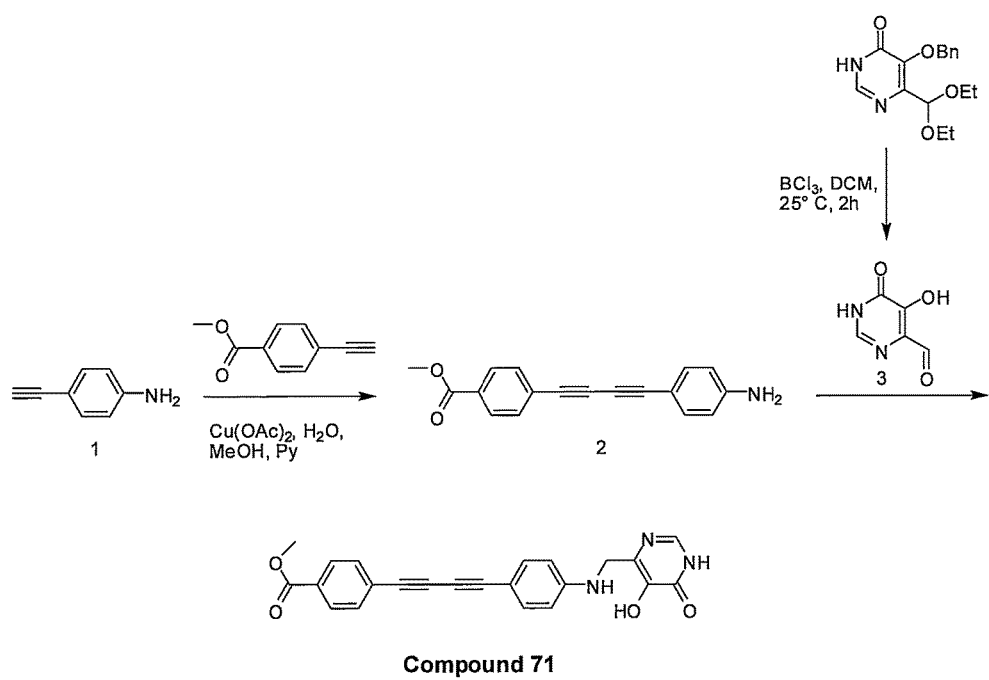
FIG. 5 shows a synthetic scheme to prepare compound 71.

The synthetic scheme to prepare compound 71 is shown in FIG. 5.

Synthesis of methyl 4-((4-aminophenyl) buta-1,3-diyn-1-yl)benzoate (2)

4-ethynylaniline (5 g, 0.0426 mol) and methyl 4-ethynylbenzoate (13.6 g, 0.085 mol) were taken in methanol : pyridine (100 ml : 20 ml) mixture and stirred for 15 min. Copper acetate (25.5 g, 0.128 mol) was added in one portion and stirred the reaction mass for 3 h. After completion of reaction, reaction mixture was concentrated, obtained crude was taken in 1.5N HCl (2×100 mL) and extracted with ethyl acetate. The separated organic layer was dried over anhydrous $Na_2SO_4$ and concentrated. The obtained crude was purified by flash chromatography over 230-400 mesh column silica gel with gradient elution of 2-6% ethyl acetate in pet ether to get 2 as light yellow solid (5.6 g). Yield: 47.8%. LC-MS and $^{1-}14$ NMR confirm the required product. LCMS Calculated for $C_{18}H_{13}NO_2$: 275. 31, Observed 276.3.

Synthesis of 5-hydroxy-6-oxo-1,6-dihydropyrimidine-4-carbaldehyde (3)

5-(benzyloxy)-6-(diethoxymethyl)pyrimidin-4(3H)-one (0.6 g, 0.0019 mol) was taken in dry DCM (10 ml) and boron trichloride (1M in DCM) (6 ml) was added drop wise and stirred the reaction mass at 25° C. for 2 h. After completion of the reaction, reaction mixture was quenched with methanol and concentrated under reduced pressure to get 3 as pale brown solid (0.26 g). Yield: 96.2%. LC-MS and $^1H$ NMR confirm the required product. LCMS Calculated for $C_5H_4N_2O_3$: 140.10, Observed (ES) 141.2.

Methyl 4-((4-(((5-hydroxy-6-oxo-1,6-dihydropyrimidin-4-yl)methyl)amino)phenyl)buta-1,3-diyn-1-yl)benzoate, 71

A suspension of 5-hydroxy-6-oxo-1,6-dihydropyrimidine-4-carbaldehyde (0.06 g, 0.00042 mol) and methyl 4-((4-aminophenyl) buta-1,3-diyn-1-yl)benzoate (0.09 g, 0.00034 mol) in methanol (2 ml) and AcOH (catalytic amount, 0.06m1) was stirred at 25° C. for 15 min. $NaCNBH_4$ resin was added in one portion and stirred the reaction mass for 1 h. Solid precipitated out from the reaction was decanted from the resin by adding excess methanol and filtered. Solid obtained was washed with 10% DCM in methanol (2×5 mL) to remove the unreacted amine and dried under reduced pressure to obtain compound 71 as light red solid. Yield: 0.06 g, (35.2%). LCMS Calculated for $C_{23}H_{17}N_3O_4$: 399.41, Observed 400.1.

Synthesis of Compound 72

Figure 6:
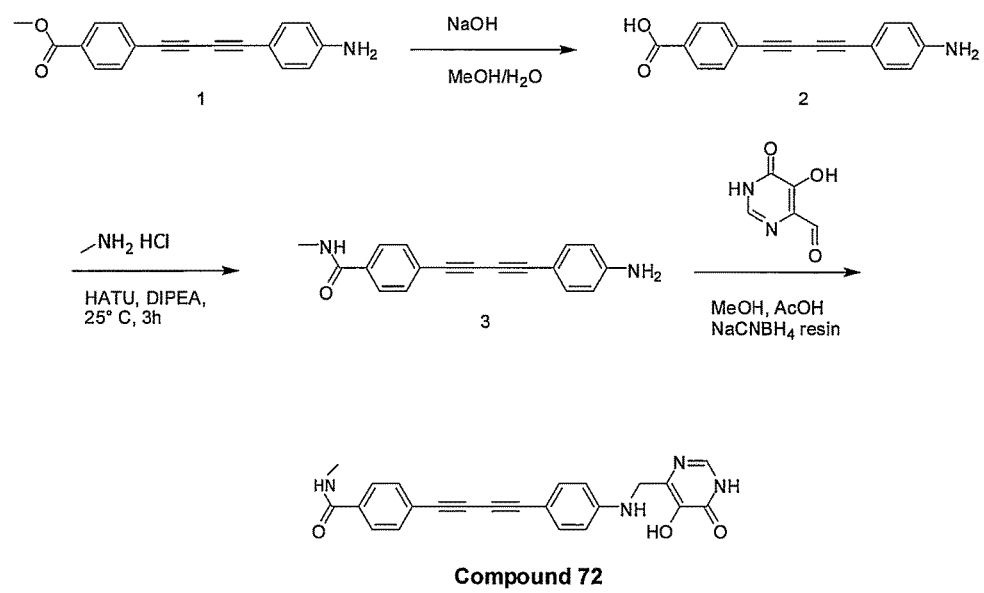
FIG. 6 shows a synthetic scheme to prepare compound 72.

The synthetic scheme to prepare compound 72 is shown in FIG. 6.

Synthesis of 4-((4-aminophenyl)buta-1,3-diyn-1-yl) benzoic acid (2)

Methyl 4-((4-aminophenyl)buta-1,3-diyn-1-yl)benzoate, 1 (1 g, 0.00363 mol) was taken in methanol : water (20 ml : 10 ml) mixture and NaOH (0.436 g, 0.0109 mol) was added and stirred for 3 h. After completion of the reaction, reaction mixture was concentrated, the resultant crude product was acidified with concentrated HCl (adjusted pH=2). The obtained solid was filtered and washed with water and dried under reduced pressure get 2 as light yellow solid (0.9 g). Yield: 95.7%. LC-MS and $^1H$ NMR confirm the required product. MS (ES) (M+H)$^+$: 262.28(M+) for $C_{17}H_{11}NO_2$.

Synthesis of 4-((4-aminophenyl)buta-1,3-diyn-1-yl)-N-methylbenzamide (3)

4-((4-aminophenyl)buta-1,3-diyn-1-yl)benzoic acid, 2 (0.5 g, 0.0019 mol) was taken in dry DMF (10 ml), methyl amine HCl (0.203 g, 0.0028 mol), DIPEA (0.493 g, 0.00382 mol) and HATU (1.45 g, 0.00382 mol) respectively were added and stirred the reaction mass for 3 h. After completion of the reaction, reaction mixture was concentrated and added crushed ice. The solid obtained was filtered and washed with water and dried under reduced pressure to get 3 as light orange solid (0.38 g). Yield: 73.1%. LC-MS and $^1$H NMR confirm the required product. MS (ES) (M+H)$^+$: 275.32 (M+) for $C_{18}Hl_4N_2O$.

4-((4-(((5-hydroxy-6-oxo-1,6-dihydropyrimidin-4-yl)methyl)amino)phenyl)buta-1,3-diyn-1-yl)-N-methylbenzamide, 72

A suspension of 5-hydroxy-6-oxo-1,6-dihydropyrimidine-4-carbaldehyde (0.3 g, 0.00214 mol) and 4-((4-aminophenyl)buta-1,3-diyn-1-yl)-N-methylbenzamide, 3 (0.587 g, 0. 00214 mol) in methanol (5 ml) and AcOH (catalytic amount, 0.3m1) was stirred at 25° C. for 15 min. NaCNBH$_4$ resin (0.3 g) was added in one portion and stirred the reaction mass for 1 h. The solid crashed out from the reaction was decanted from the resin by adding excess methanol. The decanted solid obtained was washed with 10% DCM in methanol (2×5 mL) to remove the unreacted amine and dried under reduced pressure to get 72 as off white solid. (0.19 g). Yield: 20.6%. MS (ES) (M+H)$^+$: 399.2(M+) for $C_{23}H_{18}N_4O_3$.

Synthesis of Compound 73

Figure 7:
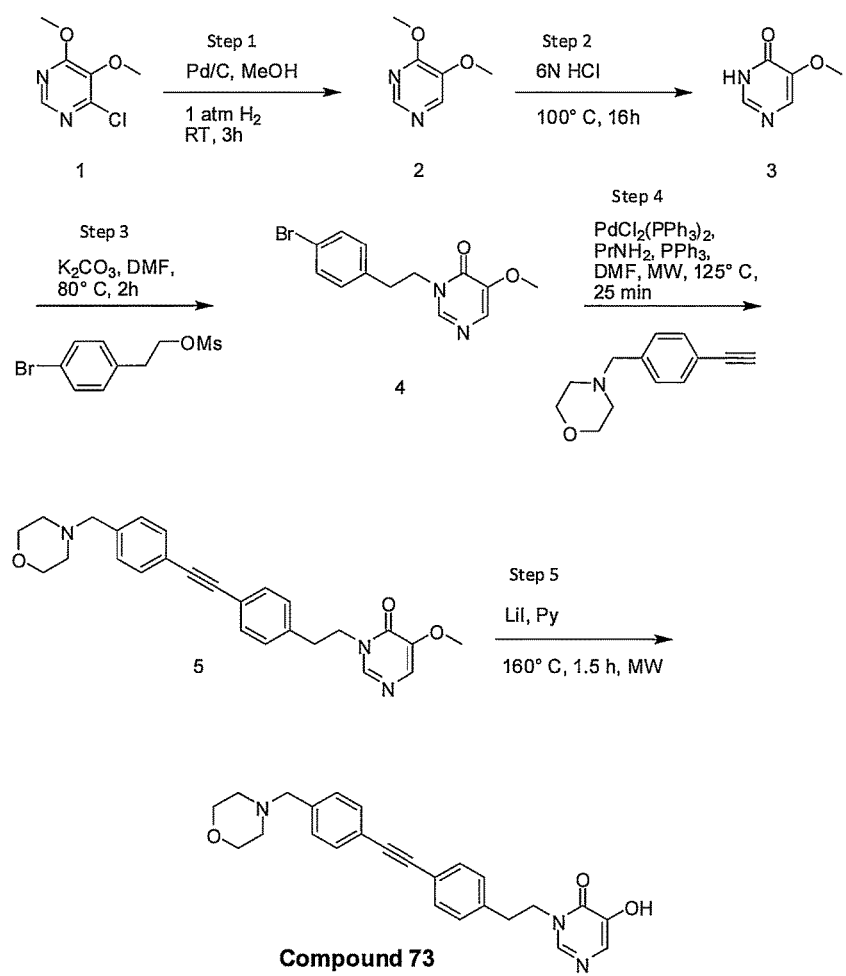
FIG. 7 shows a synthetic scheme to prepare compound 73.

The synthetic scheme to prepare compound 73 is shown in FIG. 7.

Step1 : Synthesis of 4,5-dimethoxypyrimidine, 2

A solution of 4-chloro-5,6-dimethoxypyrimidine, 1 (5g, 28.64 mmol) in dry methanol (100 mL) was hydrogenated at 1 atm H$_2$ gas pressure using Pd (10%) on carbon (1 g) as catalyst for 3 hours. After completion of the reaction, the reaction mixture was filtered through celite pad and concentrated to dryness to get (4 g, 99%) of pure 4,5-dimethoxypyrimidine, 2, as a white solid. UPLC=Calculated for $C_6H_8N_2O_2$ 140.14, Observed=141.1.

Step 2:Synthesis of 5-methoxypyrimidin-4(3H)-one hydrochloride, 3

A solution of 4,5-dimethoxypyrimidine, 2 (3 g, 21.41 mmol) in 6N HCl solution (30 mL) was heated at 100° C. for 16 h. After completion of the reaction, the reaction mixture was concentrated to dryness. The off-white residue was triturated with EtOAc (20 mL) and decanted to get pure (2.8 g, 80%) HCl salt of 5-methoxypyrimidin-4(3H)-one, 3, as an off- white solid. LCMS Calculated for $C_5H_6N_2O_2$: 126.12, Observed=127.0.

Step 3:Synthesis of 3-(4-bromophenethyl)-5-methoxypyrimidin-4(3H)-one, 4

To a stirred solution of 5-methoxypyrimidin-4(3H)-one hydrochloride, 3 (2 g, 12.3 mmol) and 4-bromophenethyl methanesulfonate (3.4 g, 12.3 mmol) in dry DMF (40 mL) was added anhydrous K$_2$CO$_3$ (5.1 g). The reaction mixture was heated at 80° C. for 2 hours. After completion of the reaction, the reaction mixture was diluted with water (30 mL), and the crude product was extracted with EtOAc (3×20 mL). The combined organic layer was washed with water (2×20 mL) and finally with brine solution (20 mL). The organic layer was dried over anhydrous Na$_2$SO$_4$, filtered and concentrated to get crude product as a pale yellow solid which is further purified by automated flash column chromatography over silica gel (eluent: 90-100% EtOAc in pet ether) to obtain (800 mg, 21%) 3-(4-bromophenethyl)-5-methoxypyrimidin-4(3H)-one, 4, as a white solid. LCMS Calculated for $C_{13}H_{13}BrN_2O_2$: 309.16, Observed=311.0.

Step 4:Synthesis of 5-methoxy-3-(44(4-(morpholinomethyl)phenyl)ethynyl)phenethyl)-pyrimidin-4(3H)-one, 5

To a solution of 3-(4-bromophenethyl)-5-methoxypyrimidin-4(3H)-one, 4 (100 mg, 0.32 mmol) and 4-(4-ethynylbenzyl) morpholine (130 mg, 0.65 mmol) in dry DMF (2 mL) was added diisopropylamine (0.18 mL, 1.28 mmol) and triphenyl phosphine (8 mg, 0.03 mmol) at RT. The reaction was degassed by purging with N$_2$ for 15 minutes. Then, copper (I) iodide (4 mg, 0.02 mmol) followed by PdCl$_2$ (PPh$_3$)$_2$ (5 mg, 0.006 mmol) were added, and the reaction mixture was heated at 125° C. for 25 min in a microwave reactor. After completion of the reaction, the reaction mixture was diluted with water (10 mL), and the crude product was extracted with EtOAc (3×10 mL). The combined organic layer was washed with water (2×10 mL) and finally with brine solution (10 mL). The organic layer was dried over anhydrous Na$_2$SO$_4$, filtered and concentrated to get crude product as a brown gummy syrup which is further purified by automated flash column chromatography over silica gel (eluent: 5-7% MeOH in DCM) to obtain (50 mg, 37%) 5-methoxy-3-(4-((4(morpholinomethyl)-phenyl)ethynyl)phenethyl)pyrimidin-4(3H)-one, 4 as an yellow solid. LCMS Calculated for $C_{26}H_{27}N_3O_3$: 429.52, Observed=429.2.

Step 5:Synthesis of 5-hydroxy-3-(44(4-(morpholinomethyl)phenyl)ethynyl)phenethyl)-pyrimidin-4(3H)-one, 73

To a solution of 5-methoxy-3-(4-((4(morpholinomethyl)phenyl)ethynyl) phenethyl) pyrimidin(3H)-one, 4 (25 mg, 0.06 mmol) in dry pyridine (1 mL) was added lithium iodide (40 mg, 0.29 mmol). The reaction mixture was heated at 160° C. for 90 min in a microwave reactor. After completion of the reaction, the reaction mixture was concentrated to dryness and the residue was dissolved in EtOAc (10 mL). The organic layer was washed with water and brine solution, dried over anhydrous Na$_2$SO$_4$, filtered and concentrated to get crude product as a pale yellow solid. The solid was further purified by trituration with diethyl ether to obtain (8 mg, 33%) compound 73 as an off-white solid. LCMS Calculated for $C_{25}H_{25}N_3O_3$: 415.49, Observed=416.0.

Synthesis of Compounds 74, 75, 76, 78, 86, 88, 97, 99 and 100

Figure 8:
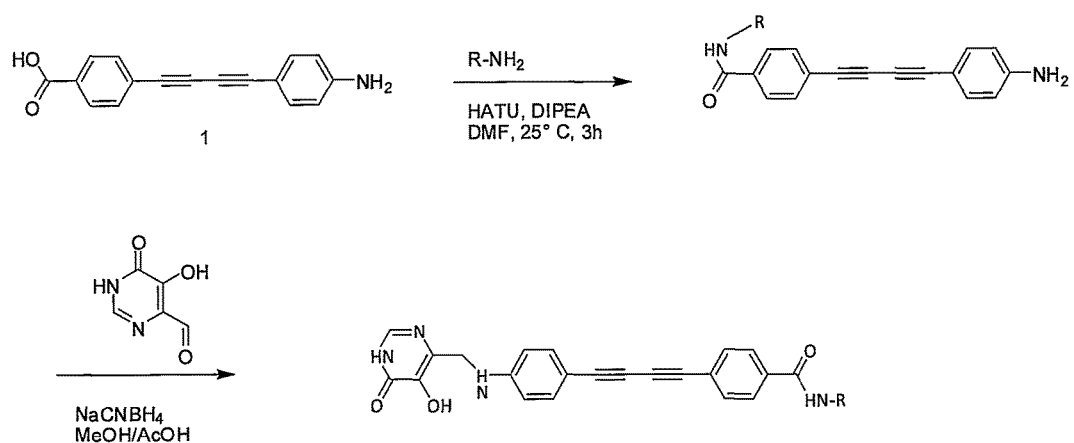
FIG. 8 shows a synthetic scheme to prepare exemplary compounds of the disclosure.

The synthetic scheme to prepare the amide backbones for compounds 74, 75, 76, 78, 86, 88, 97, 99 and 100 is shown in FIG. 8.

Synthesis of Amides:

4-((4-aminophenyl)buta-1,3-diyn-1-yl)benzoic acid, 1 (0.3 g, 0.0014 mol) was taken in dry DMF (5 ml), R-NH$_2$ (0.0012 mol, 1.05 eq), DIPEA (0.296 g, 0.00229 mol) and HATU (0.655 g, 0.00172 mol) respectively were added and stirred the reaction mass for 3 h. After completion of the reaction, the reaction mixture was concentrated and added crushed ice. The solids obtained were filtered and washed with water and dried under reduced pressure to get the respective amides. The amide backbones for compounds 75, 76, 78, 99 and 86 were obtained by extraction and further column purification using 1-10% MeOH in DCM as eluent. The remaining compounds were obtained by trituration using cold water. LC-MS and $^1$H NMR confirm the required product.

TABLE 2

Quantities and the purity of exemplary synthesized amide backbones

| Compound ID No. | R—NH$_2$ | Qty of amide | Yield | Purification |
|---|---|---|---|---|
| 97 | morpholine (N-H, O) | 0.352 g | 94.5% | trituration |
| 74 | 4-(dimethylamino?)-N-methylpiperidine (1-methyl-4-aminopiperidine derivative) | 0.36 g | 85.7% | trituration |
| 75 | 2-(pyrrolidin-1-yl)ethan-1-amine | 0.37 g | 90.2% | Column Chromatography |
| 76 | N,N-diethyl-1,3-propanediamine | 0.40 g | 93.2% | Column chromatography |
| 100 | 3-(dimethylamino)pyrrolidine | 0.38 g | 92.6% | Trituration |
| 78 | 4-(piperidin-4-yl)morpholine | 0.39 g | 78.7% | Column chromatography |
| 99 | (S)-pyrrolidin-2-ylmethanol | 0.37 g | 94.8% | Column chromatography |
| 86 | 3-hydroxyazetidine | 0.35 g | 96.4% | Column chromatography |
| 88 | 2-aminoethanol | 0.35 | 60.3% | Trituration |

TABLE 3

LCMS data of exemplary synthesized amide backbones

| Compound ID No. | Structure of the Amide | LCMS |
|---|---|---|
| 97 | (morpholine-N-C(O)-C6H4-C≡C-C≡C-C6H4-NH2) | Calculated for $C_{21}H_{18}N_2O_2$ 330.39, Observed = 331.2 |
| 74 | (4-dimethylaminopiperidine-N-C(O)-C6H4-C≡C-C≡C-C6H4-NH2) | Calculated for $C_{24}H_{25}N_3O$ 371.48, Observed = 372.5 |
| 75 | (pyrrolidine-N-CH2CH2-NH-C(O)-C6H4-C≡C-C≡C-C6H4-NH2) | Calculated for $C_{23}H_{23}N_3O$ 357.46, Observed = 358.2 |
| 76 | (Et2N-CH2CH2CH2-NH-C(O)-C6H4-C≡C-C≡C-C6H4-NH2) | Calculated for $C_{24}H_{27}N_3O$ 373.5, Observed = 374.5 |
| 100 | (3-dimethylaminopyrrolidine-N-C(O)-C6H4-C≡C-C≡C-C6H4-NH2) | Calculated for $C_{23}H_{23}N_3O$ 357.46, Observed = 358.2 |
| 78 | (4-morpholinopiperidine-N-C(O)-C6H4-C≡C-C≡C-C6H4-NH2) | Calculated for $C_{26}H_{27}N_3O_2$ 413.52, Observed = 414.0 |
| 99 | (2-(hydroxymethyl)pyrrolidine-N-C(O)-C6H4-C≡C-C≡C-C6H4-NH2) | Calculated for $C_{22}H_{20}N_2O_2$ 344.41, Observed = 345.4 |

TABLE 3-continued

LCMS data of exemplary synthesized amide backbones

| Compound ID No. | Structure of the Amide | LCMS |
|---|---|---|
| 86 | | Calculated for $C_{20}H_{16}N_2O_2$ 316.36, Observed = 317.3 |
| 88 | | Calculated for $C_{19}H_{16}N_2O_2$ 304.3, Observed = 305.3 |
| 111 | | Calculated for $C_{27}H_{29}N_3O_4$ 459.55, Observed = 460.0 |

Synthesis of Compound 104

Figure 9:
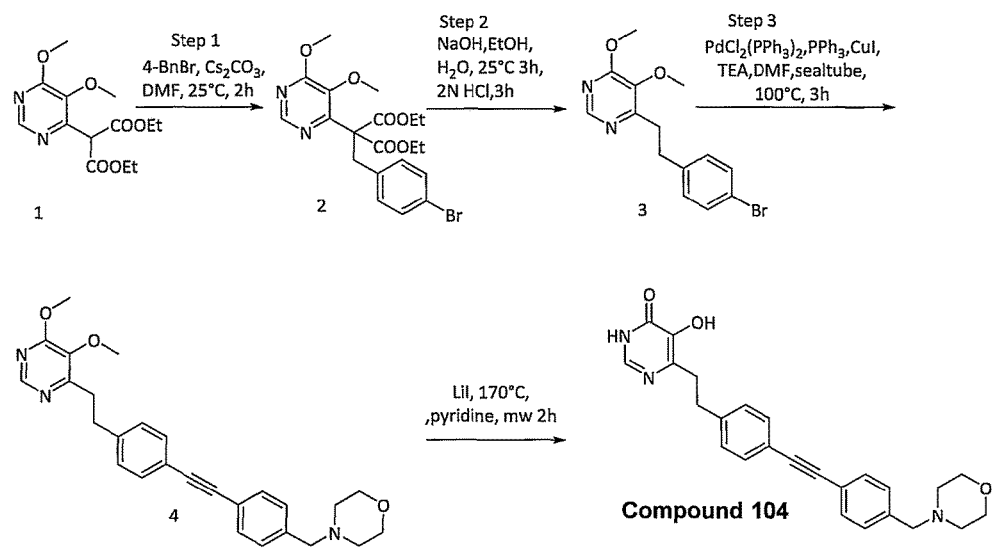
FIG. 9 shows a synthetic scheme to prepare compound 104.

The synthetic scheme to prepare compound104 is shown in FIG. 9.

Step 1: Synthesis of diethyl 2-(4-bromobenzyl)-2-(5,6-dimethoxypyrimidin-4-yl)malonate, 2

To a solution of Diethyl 2-(5,6-dimethoxypyrimidin-4-yl) malonate (0.2 g, 0.67 mmol) in DMF (5 mL) $Cs_2CO_3$ (0.32 g, 1.0 mmol) and 4-bromo benzyl bromide (0.16 g, 0.67 mmol) were added and stirred at 25° C. for 1 h. After completion of the reaction, the reaction mixture was diluted with water and extracted with EtOAc (2*25 mL). The combined organic layers were washed with brine solution, dried over $Na_2SO_4$, filtered and concentrated. The crude product was purified by column chromatography to get (0.21 g, 67%) of pure diethyl 2-(4-bromobenzyl)-2-(5,6-dimethoxypyrimidin-4-yl)malonate, 2. UPLC=Calculated for C20H23BrN2O6 467.32, Observed=469.32

Step 2: Synthesis of 4-(4-bromophenethyl)-5,6-dimethoxypyrimidine, 3

A solution of 2-(4-bromobenzyl)-2-(5,6-dimethoxypyrimidin-4-yl)malonate, 2 (0.2 g, 0.74 mmol) in EtOH (3 mL) and $H_2O$ (3 mL) was added NaOH (0.15 g, 3.74 mmol) and stirred at 25° C. for 3 h. After completion of the reaction, the reaction mixture was diluted with water, acidified with 1.5 N HCl and extracted with EtOAc (2*20 mL). The combined organic layers were concentrated and obtained crude product was stirred in 2N HCl for 3h. After completion of the reaction, the reaction mixture was diluted with water and extracted with EtOAc (2*10 mL). The combined organic layers were washed with brine solution, dried over $Na_2SO_4$, filtered and concentrated. The crude product was purified by column chromatography to get (0.058 g, 44.6%) of pure diethyl 4-(4-bromophenethyl)-5,6-dimethoxypyrimidine, 3. UPLC=Calculated for C14H15BrN2O2 323.19, Observed=325.2

Step 3: Synthesis of 4-(4-((4-(2-(5,6-dimethoxypyrimidin-4-yl)ethyl)phenyl)ethynyl)benzyl) morpholine, 4

To solution of 4-(4-bromophenethyl)-5,6-dimethoxypyrimidine, 3 (0.05 g, 0.14 mmol) in DMF (1 mL) were added 4-(4-ethynylbenzyl)morpholine (0.055 g, 0.27 mmol), dipropylamine (0.057 g, 0.57 mmol) and triphenylphosphine (0.05 g, 0.0002 mol). The reaction mixture was purged with nitrogen for 10 min, $PdCl_2(PPh_3)_2$ (4 mg, 0.014 mmol) was added followed by CuI (2 mg, 0.08mmol) and heated the reaction mixture in sealed tube for 3h at 100° C. After completion of the reaction, the reaction mixture was dissolved in water and extracted with EtOAc (2*10 mL). The combined organic layers were washed with brine solution, dried over Na2SO4, filtered and concentrated and the crude product was purified by column chromatography to get pure (0.03 g, 44%) of 4-(4-((4-(2-(5,6-dimethoxypyrimidin-4-yl) ethyl)phenyl)ethynyl)benzyl)morpholine, 4. LCMS=Calculated for C27H29N3O3 443.55, Observed =444.2

Step 4: Synthesis of 5-hydroxy-6-(4-((4-(morpholinomethyl)phenyl)ethynyl)phenethyl) pyrimidin-4 (3H)-one, Compound 104

To a solution of 4-(4-((4-(2-(5,6-dimethoxypyrimidin-4-yl)ethyl)phenyl)benzyl)morpholine, 4 (0.03 g, 0.07 mmol), Lithium iodide (0.056 g, 0.42 mmol) was added and microwaved for 2h at 170° C. After completion of the reaction pyridine was removed and dissolved in EtOAc and the organic layer was washed with water and brine solution. The organic layer was dried over Na2SO4, filtered and concentrated. The crude product was purified by prep TLC to get pure (5 mg, 17.8%) 5-hydroxy-6-(4-((4-(morpholinomethyl)phenyl)ethynyl)phenethyl)pyrimidin-4(3H)-one, compound 104. LCMS =Calculated for C25H25N3O3 415.49, Observed=416.0

Synthesis of Compound 105

Figure 10:
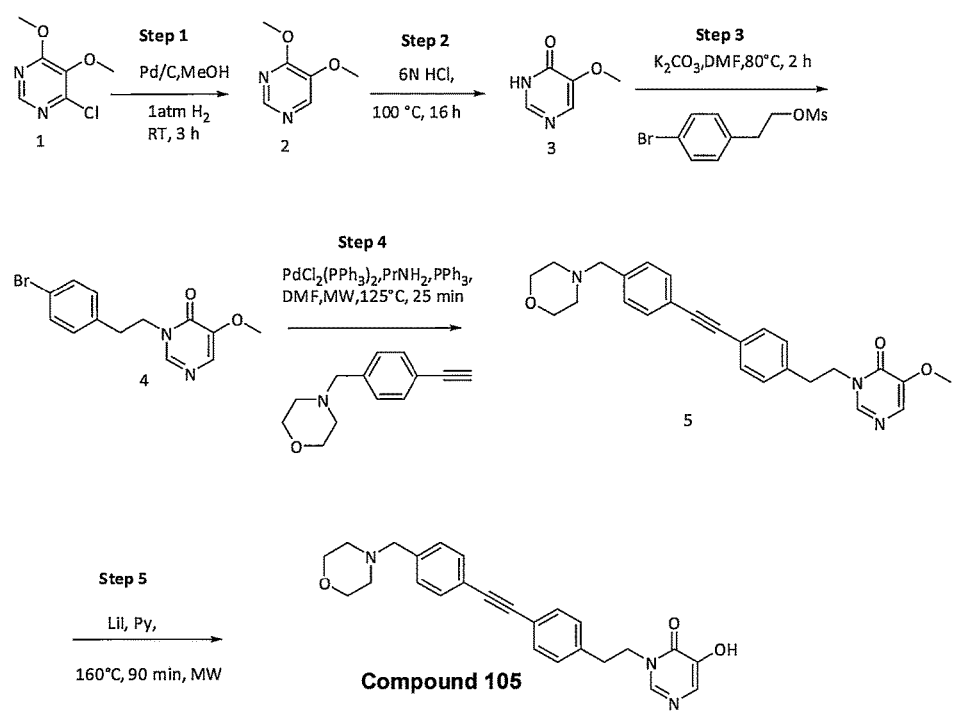
FIG. 10 shows a synthetic scheme to prepare compound 105.

The synthetic scheme to prepare compound105 is shown in FIG. 10.

Step1:Synthesis of 4,5-dimethoxypyrimidine, 2

A solution of 4-chloro-5,6-dimethoxypyrimidine, 1 (5g, 28.64 mmol) in dry Methanol (100 mL) was hydrogenated at 1 atm $H_2$ gas pressure using Pd (10%) on carbon (1 g) as catalyst for 3 hours. After completion of the reaction, the reaction mixture was filtered through celite pad and concentrated to dryness to get (4 g, 99%) of pure 4,5-dimethoxypyrimidine, 2 as a white solid. UPLC=Calculated for $C_6H_8N_2O_2$ 140.14, Observed=141.1.

Step 2:Synthesis of 5-methoxypyrimidin-4(3H)-one hydrochloride, 3

A solution of 4,5-dimethoxypyrimidine, 2 (3 g, 21.41 mmol) in 6N HCl solution (30 mL) was heated at 100° C. for 16 h. After completion of the reaction, the reaction mixture was concentrated to dryness. The off-white residue was triturated with EtOAc (20 mL) and decanted to get pure (2.8 g, 80%) HCl salt of 5-methoxypyrimidin-4(3H)-one, 3 as an off- white solid. LCMS =Calculated for $C_5H_6N_2O_2$ 126.12, Observed =127.0.

Step 3:Synthesis of 3-(4-bromophenethyl)-5-methoxypyrimidin-4(3H)-one, 4

To a stirred solution of 5-methoxypyrimidin-4(3H)-one hydrochloride, 3 (2 g, 12.3 mmol) and 4-bromophenethyl methanesulfonate (3.4 g, 12.3 mmol) in dry DMF (40 mL) was added anhydrous $K_2CO_3$ (5.1 g). The reaction mixture was heated at 80° C. for 2 hours. After completion of the reaction, the reaction mixture was diluted with water (30 mL) and the crude product was extracted with EtOAc (3×20 mL). The combined organic layer was washed with water (2×20 mL) and finally with brine solution (20 mL). The organic layer was dried over anhydrous $Na_2SO_4$, filtered and concentrated to get crude product as a pale yellow solid which is further purified by automated flash column chromatography over silica gel (eluent: 90-100% EtOAc in Pet ether) to obtain (800 mg, 21%) 3-(4-bromophenethyl)-5-methoxypyrimidin-4(3H)-one, 4 as a white solid. LCMS=Calculated for $C_{13}H_{13}BrN_2O_2$ 309.16, Observed =311.0.

Step 4:Synthesis of 5-methoxy-3-(44(4-(morpholinomethyl)phenyl)ethynyl)phenethyl)pyrimidin-4 (3H)-one, 5

To a solution of 3-(4-bromophenethyl)-5-methoxypyrimidin-4(3H)-one, 4 (100 mg, 0.32 mmol) and 4-(4-ethynylbenzyl) morpholine (130 mg, 0.65 mmol) in dry DMF (2 mL) was added Dipropylamine (0.18 mL, 1.28 mmol) and Triphenyl phosphine (8 mg, 0.03 mmol) at RT. The reaction was degassed by purging with $N_2$ for 15 minutes. Then, Copper (I) iodide (4 mg, 0.02 mmol) followed by $PdCl_2$ $(PPh_3)_2$ (5 mg, 0.006 mmol) were added and the reaction mixture was heated at 125° C. for 25 min. in a microwave reactor. After completion of the reaction, the reaction mixture was diluted with water (10 mL) and the crude product was extracted with EtOAc (3×10 mL). The combined organic layer was washed with water (2×10 mL) and finally with brine solution (10 mL). The organic layer was dried over anhydrous $Na_2SO_4$, filtered and concentrated to get crude product as a brown gummy syrup which is further purified by automated flash column chromatography over silica gel (eluent: 5-7% MeOH in DCM) to obtain (50 mg, 37%) 5-methoxy-3-(4-((4(morpholinomethyl)phenyl)ethynyl) phenethyl) pyrimidin-4(3H)-one, 4 as an yellow solid. LCMS=Calculated for $C_{26}H_{27}N_3O_3$ 429.52, Observed=429.2.

Step 5:Synthesis of 5-hydroxy-3-(4-((4-(morpholinomethyl)phenyl)ethynyl) phenethyl)pyrimidin-4 (3H)-one, Compound 105

To a solution of 5-methoxy-3-(4-((4(morpholinomethyl)phenyl)ethynyl) phenethyl) pyrimidin-4(3H)-one, 4 (25 mg, 0.06 mmol) in dry pyridine (1 mL) was added lithium iodide (40 mg, 0.29 mmol). The reaction mixture was heated at 160° C. for 90 min. in a microwave reactor. After completion of the reaction, the reaction mixture was concentrated to dryness and the residue was dissolved in EtOAc (10 mL). The organic layer was washed with water and brine solution, dried over anhydrous $Na_2SO_4$, filtered and concentrated to get crude product as a pale yellow solid. It is further purified by trituration with diethyl ether to obtain (8 mg, 33%) FRG_046 as an off-white solid. LCMS=Calculated for $C_{25}H_{25}N_3O_3$ 415.49, Observed =416.0.

Synthesis of Compound 107 and 108

Figure 11:
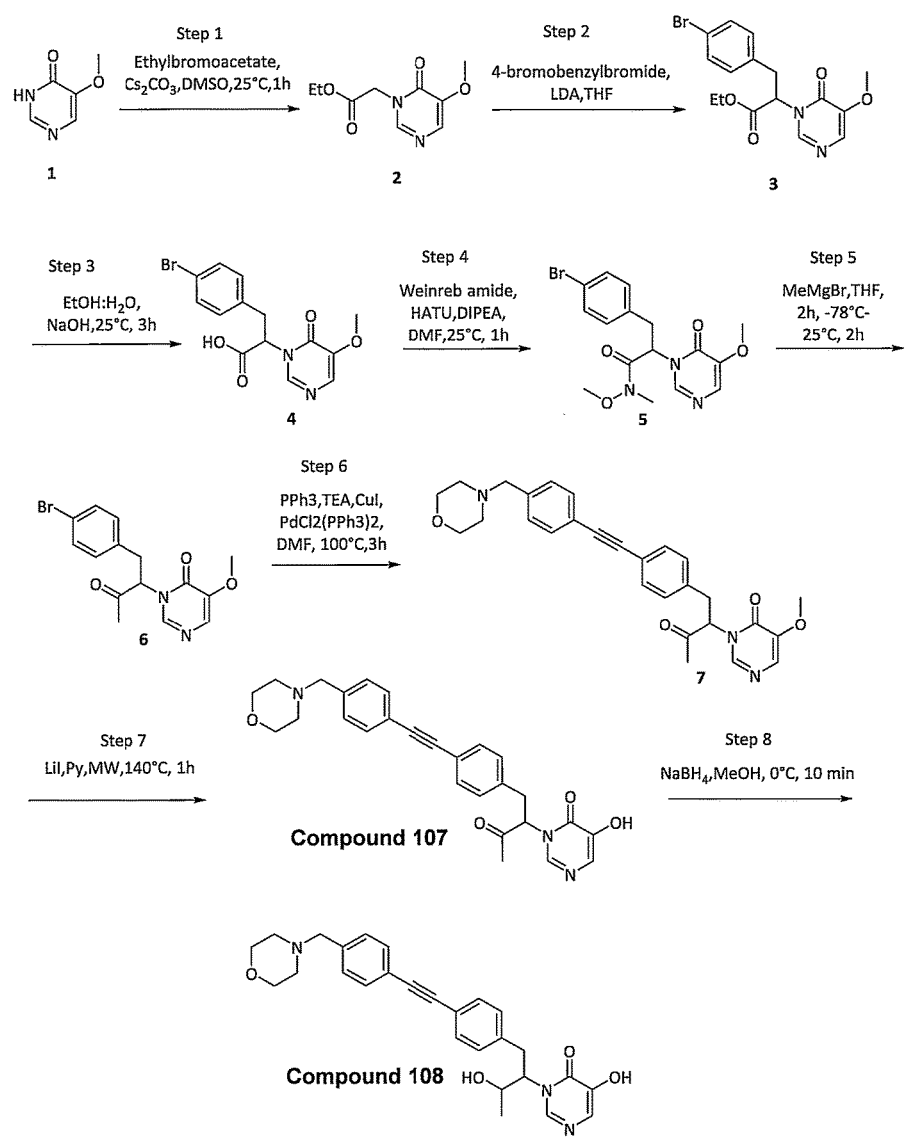
FIG. 11 shows a synthetic scheme to prepare compounds 107 and 108.

The synthetic scheme to prepare compounds 107 and 108 is shown in FIG. 11.

Step 1:Ethyl 2-(5-methoxy-6-oxopyrimidin-1(6H)-yl) acetate (2)

To a solution of 5-methoxypyrimidin-4(3H)-one, 1 (2 g, 0.0158 mol) in DMSO (10 mL), $Cs_2CO_3$ (15.4 g, 0.0475 mol) was added followed by ethyl bromoacetate (3.97 g, 0.0237 mol) and stirred at 25° C. for 1 h. After completion of the reaction, the reaction mixture was diluted with water and extracted with EtOAc. The aqueous layer was extracted with EtOAc (2×100 mL). The combined organic layers were washed with brine and organic layer was dried over anhydrous $Na_2SO_4$, filtered and concentrated under reduced pressure to get (2.6 g, 81.2%) of 2. This was taken to the next step without further purification. UPLC=Calculated for $C_9H_{12}N_2O_4$ is 212.21, Observed=213.2 $[M+H]^+$.

Step 2:Ethyl 3-(4-bromophenyl)-2-(5-methoxy-6-oxopyrimidin-1(6H)-yl) propanoate (3)

To a solution of 2 (2.5 g, 0.0117 mol) in THF (25 mL), LDA (2M in THF, 7.06 mL, 0.014 mol) was added at -78° C. over a period of 10 min. To this cooled solution, 4-bromo benzylbromide (2.94 g, 0.0117 mol) was added and stirred for 1 h. After completion of the reaction, the reaction mixture was quenched with sat $NH_4Cl$ solution and the reaction mixture was extracted with EtOAc (2×100 mL). The aqueous layer was acidified with 1.5 N HCl (pH=5) and extracted with EtOAc. The combined organics was washed with brine and organic layer was dried over anhydrous Na$_2$SO$_4$, filtered and concentrated under reduced pressure to get a mixture of 3 (1.4 g, 56%) and 4 (1.1 g, 23.9%). LC_MS=Calculated for C$_{16}$H$_{17}$BrN$_2$O$_4$, 381.23, Observed=382.4 [M+H]$^+$.

Step 3: 3-(4-bromophenyl)-2-(5-methoxy-6-oxopyrimidin-1(6H)-yl)propanoic acid (4)

To a solution of 3 (1.6g, 0.004 mol) in EtOH (10 mL), water (10 mL) was added followed by NaOH (0.83 g, 0.0209 mol) and stirred the reaction mixture for 3 h. After completion of the reaction, the reaction mixture was diluted with water and washed with diethyl ether. The aqueous layer was acidified with 1.5 N HCl to pH=5 and extracted with EtOAc (2×30 mL). The combined organics was washed with brine and organic layer was dried over Na$_2$SO$_4$ and concentrated under reduced pressure to get (1.3 g, 87.8%) of 4. This was pure enough to be used in the next step without further purification. UPLC=Calculated for C$_{24}$Fl$_{13}$BrN$_2$O$_4$, 353.17, Observed=354.3 [M+H]$^+$.

Step 4: 3-(4-bromophenyl)-N-methoxy-2-(5-methoxy-6-oxopyrimidin-1(6H)-yl)-N-methylpropanamide 5)

To a solution of 4 (1.5 g, 0.0042 mol) in DMF (15 mL), N, O-dimethylhydroxylamine.HCl (0.608 g, 0.0063 mol), HATU (2.3 g, 0.0063 mol) and DIPEA (2.2 mL, 0.0127 mol) was added and stirred at 25° C. for 1 h. After completion of the reaction, the reaction mixture was diluted with water and extracted with EtOAc (2×100 mL). The combined organics was washed with brine and organic layer was dried over anhydrous Na$_2$SO$_4$, and concentrated under reduced pressure to get (1.3 g, 77.3%) of 5. UPLC=Calculated for C16H18BrN3O4 396.24, Observed =396.1 [M+H]$^+$.

Step 5: 3-(1-(4-bromophenyl)-3-oxobutan-2-yl)-5-methoxypyrimidin-4(3H)-one (6)

A solution of 5 (1 g, 0.0025 mol) in THF (20 mL) was cooled –20° C. To this was added methyl magnesium bromide (3M in Et$_2$O, 2.5 mL, 0.0075 mol) and stirred at 25° C. for 1 h. After completion of the reaction, the reaction mixture was quenched with sat. NH$_4$Cl, diluted with water and extracted with EtOAc (2×10 mL). The combined organics was washed with brine and the organic layer was dried over Na$_2$SO$_4$, filtered and concentrated under reduced pressure. The crude product was purified by column chromatography on silica gel (230-400 mesh) to get (0.47 g, 52.2.2%) of 6. LCMS =Calculated for C$_{15}$H$_{15}$BrN$_2$O$_3$ 351.20, Observed =351.1[M+H]$^-$.

Step 6: 5-methoxy-3-(1-(44(4-(morpholinomethyl)phenyl)ethynyl)phenyl)-3-oxobutan-2-yl)pyrimidin-4(3H)-one (7)

To solution of 6 (0.47 g, 0.00133 mol) in DMF (5mL) was added 4-(4-ethynylbenzyl)morpholine (0.807 g, 0.00401 mol), Et$_3$N (0.54 g, 0.0053 mol) and triphenylphosphine (0.035 g, 0.00013 mol). The reaction mixture was purged with nitrogen for 10 min, PdCl$_2$(PPh$_3$)$_2$ (0.018 g ,0.000026 mol) was added followed by CuI (0.0152 g, 0.00008 mol) and the reaction mixture was heated in a sealed tube for 3 h at 100° C. After completion of the reaction, the reaction mixture was dissolved in water and extracted with EtOAc (2×30 mL). The combined organic layer was washed with brine, dried over Na$_2$SO$_4$, and concentrated. The crude product was purified by column chromatography on silica gel (230-400 mesh) to get (0.31 g, 49.2%) 7. LC_MS=Calculated for C$_{28}$H$_{29}$N$_3$O$_4$ 471.56, Observed=472.3[M+H]$^-$.

Step 7: 5-hydroxy-3-(1-(4-((4-(morpholinomethyl)phenyl)ethynyl)phenyl)-3-oxobutan-2-yl)pyrimidin-4(3H)-one, Compound 107

To a solution of 4 (0.26 g, 0.514 mmol) in pyridine (1 mL), Lithium iodide (0.43 g, 0.0038 mol) was added and heated at 140° C. under microwave irradiation for 1 h. After completion of the reaction, pyridine was removed under reduced pressure and the crude product was dissolved in water and extracted with EtOAc. The organic layer was washed with water, brine and dried over Na$_2$SO$_4$ and concentrated under reduced pressure. The crude product was purified by column chromatography on silica gel (230-400 mesh) to afford Compund 107 (60 mg, 24%) UPLC=Calculated for C$_{27}$H$_{27}$N$_3$O$_4$ 457.53, Observed =458.5 [M+H]$^+$.

Step 8: 5-hydroxy-3-(3-hydroxy-1-(4-((4-(morpholinomethyl)phenyl)ethynyl)phenyl)butan-2-yl)pyrimidin-4(3H)-one, Compound 108

To a solution of hydroxy-3-(1-(4-((4-(morpholinomethyl)phenypethynyl)phenyl)-3-oxobutan-2-yl)pyrimidin-4(3H)-one (0.01 g, 0.02 mmol) in methanol (1 mL) and THF (1 mL), Sodium borohydride (5 mg, 0.12 mmol) was added and stirred at 25° C. for 10 min. After completion of the reaction, the reaction mixture was quenched with sat. NH$_4$Cl solution and extracted with EtOAc. The organic layer was washed with brine solution and dried over Na$_2$SO$_4$, filtered and concentrated under reduced pressure to get crude product. The crude product was triturated with diethyl ether to afford Compund 108 (0.007 g, 70%). LCMS=Calculated for C$_{27}$H$_{29}$N$_3$O$_4$ 459.55, Observed=460.2 [M+H]$^+$.

Synthesis of Compound 114

Figure 12:
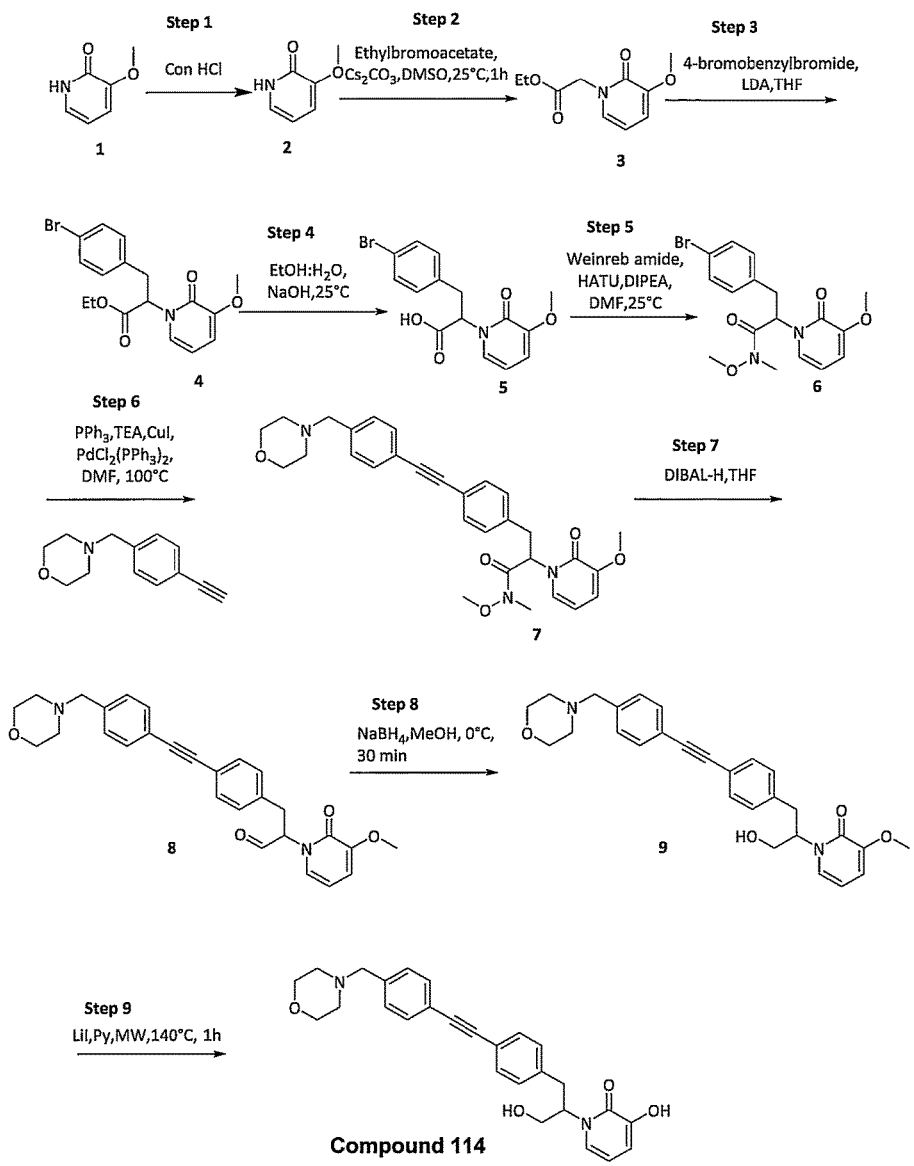
FIG. 12 shows a synthetic scheme to prepare compound 114.
Figure 13:
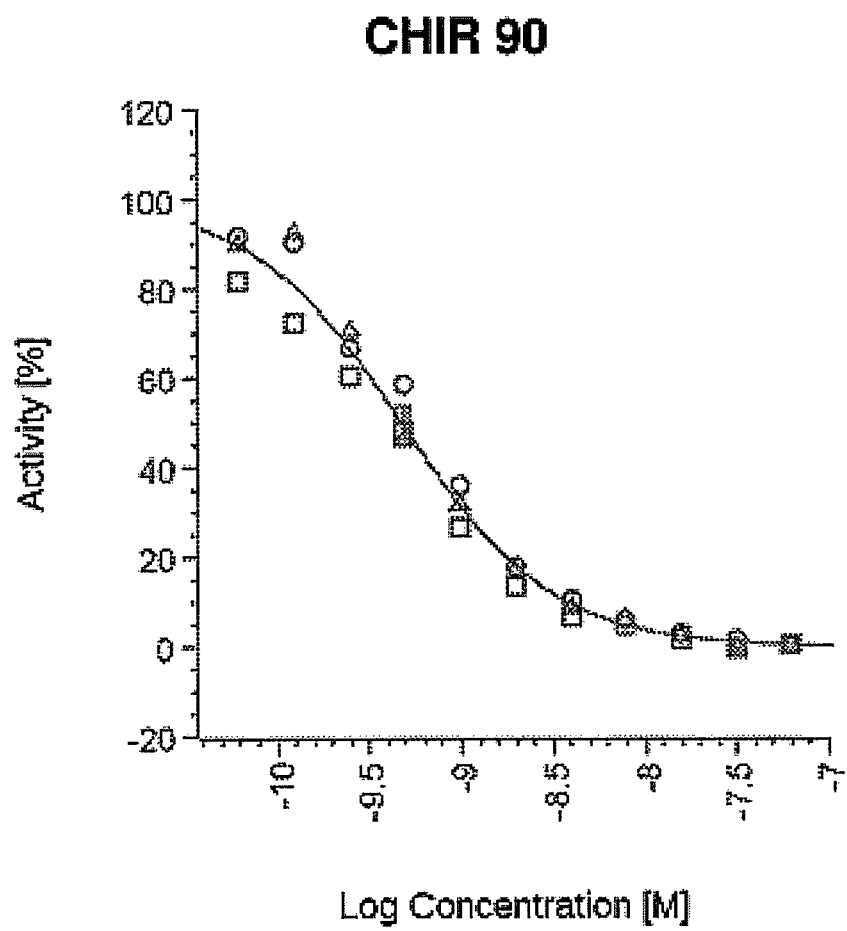
FIG. 13 shows a dose response curve for compound Chir-90 in an LpxC inhibition assay.
Figure 14:
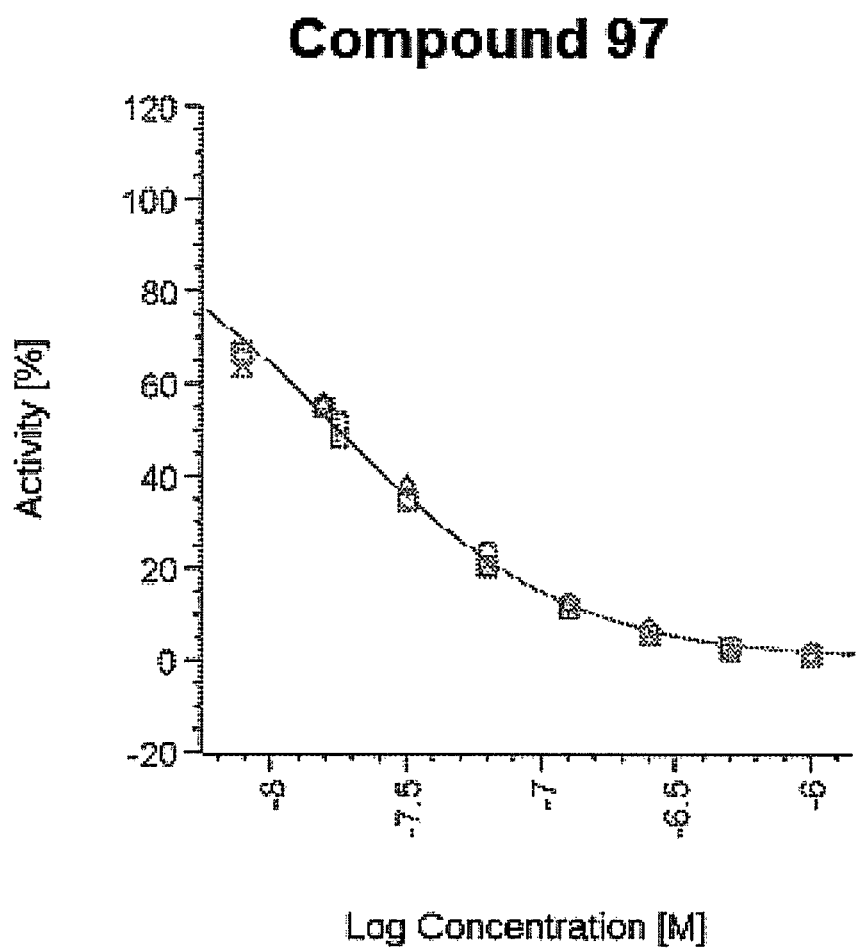
FIG. 14 shows a dose response curve for compound 97 in an LpxC inhibition assay.
Figure 15:
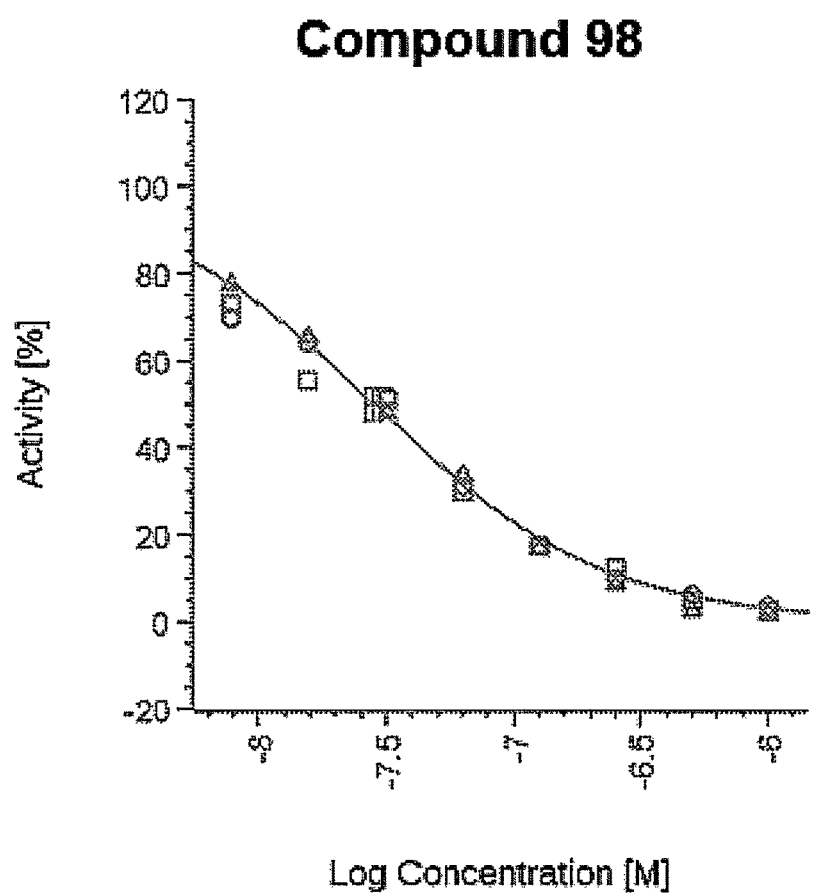
FIG. 15 shows a dose response curve for compound 98 in an LpxC inhibition assay.

The synthetic scheme to prepare compound 114 is shown in FIG. 12.

Step 1:Synthesis of 3-methoxypyridin-2(1H)-one (2)

3-methoxypyridin-2(1H)-one (3 g, 0.0213 mol) was taken in conc. HCl (30 mL) and heated at 80° C. for 5 h. After completion of the reaction, the reaction mixture was basified with sat NaHCO$_3$ and extracted with EtOAc. The organic layers were washed with brine solution and organic layer was dried over anhydrous Na$_2$SO$_4$, filtered and concentrated under reduced pressure to get (2.5 g, 93.6%) of pure 3-methoxypyridin-2(1H)-one, 2 UPLC=Calculated for C$_6$H$_7$NO$_2$ is 125.13, Observed =126.2.

Step 2:Synthesis of ethyl 2-(3-methoxy-2-oxopyridin-1(2H)-yl) acetate (3)

To a solution of 3-methoxypyridin-2(1H)-one, 2 (2.5 g, 0.02mol) in DMSO (25 mL), Cs$_2$CO$_3$ (16.4 g, 0.05 mol), ethyl bromoacetate (5.01 g, 0.03 mol) were added and stirred at 25° C. for 2 h. After completion of the reaction, the reaction mixture was diluted with water and extracted with EtOAc. The aqueous layer was extracted with EtOAc (2*100 mL). The combined organic layers were washed with brine solution and organic layer was dried over anhydrous Na$_2$SO$_4$, filtered and concentrated under reduced pressure to get 3 (2.4 g, 57.1%). UPLC=Calculated for C$_{10}$H$_{13}$NO$_4$ is 211.22, Observed =212.2.

Step 3:Synthesis of ethyl 3-(4-bromonhenyl)-2-(3-methoxy-2-oxonyridin-1(2H)-yl)propanoate (4)

To a solution of 3 (1.5 g, 0.007 mol) in THF (25 mL). LDA (2M in THF, 5.3 mL, 0.0106 mol) was added at —78° C. for 10 min. To this 4-bromo benzyl bromide (1.9 g, 0.0078 mol) was added and stirred for 1 h. After completion of the reaction, the reaction mixture was quenched with sat NH$_4$Cl solution and the reaction mixture was extracted with EtOAc (2* 100 mL). The aqueous layer was acidified with 1.5 N HCl (pH=5) and extracted with EtOAc, combined organic layers were washed with brine solution and organic layer was dried over anhydrous Na$_2$SO$_4$, filtered and concentrated under reduced pressure to get 4 (0.7 g, 25.9%) and 5 (0.6 g, 24%). LCMS=Calculated for C$_{17}$H$_{18}$BrNO$_4$, 380.24, Observed=381.4.

Step 4:Synthesis of 3-(4-bromophenyl)-2-(3-methoxy-2-oxopyridin-1(2H)-yl)propanoic acid (5)

To a solution of ethyl 3-(4-bromophenyl)-2-(3-methoxy-2-oxopyridin-1(2H)-yl)propanoate, 4 (0.7g, 0.0018 mol) in EtOH (10 mL), water (10 mL) NaOH (0.36g, 0.0092 mol) was added and stirred the reaction mixture for 4 h. After completion of the reaction, the reaction mixture was diluted with water and extracted with diethyl ether and layer was separated and the aqueous layer was acidified with 1.5N HCl to (P$^H$=5) and extracted with EtOAc (2*10 mL). The combined organic layers were washed with brine solution and organic layer was dried over Na$_2$SO$_4$, filtered and concentrated under reduced pressure to get (0.48 g, 75.1%) of pure 3-(4-bromophenyl)-2-(3-methoxy-2-oxopyridin-1(2H)-yl) propanoic acid, 5. UPLC=Calculated for C$_{15}$H$_{14}$BrNO$_4$, 352.18, Observed=353.2.

Step 5:Synthesis of 3-(4-bromonhenyl)-N-methoxy-2-(3-methoxy-2-oxonyridin-1(2H)-yl)-N-methylpropanamide (6)

To a solution of 5 (0.3 g, 0.0008 mol) in DMF (5 mL), N,O-dimethyl hydroxylamine HCl (0.078 g, 0.0012 mol), HATU (0.48g, 0.0012 mol) and DIPEA (0.33 g, 0.0025 mol) was added and stirred at 25° C. for 2 h. After completion of the reaction, the reaction mixture was diluted with water and extracted with EtOAc (2*100 mL). The combined organic layers were washed with brine solution and organic layer was dried over anhydrous Na$_2$SO$_4$, filtered and concentrated under reduced pressure to get 6 (0.28 g, 84.8%). UPLC =Calculated for C$_{17}$H$_{19}$BrN$_2$O$_4$ 395.25, Observed=396.24.

Step 6:Synthesis of N-methoxy-2-(3-methoxy-2-oxopyridin-1(2)-yl)-N-methyl-3-(4-((4-(morpholinomethyl) phenyl)ethynyl)phenyl)propanamide (7)

To a solution of 6 (0.28g, 0.00070 mol) in DMF (2 mL) was added 4-(4-ethynylbenzyl) morpholine (0.28 g, 0.0014 mol), Et$_3$N (0.28 g, 0.0028 mol) and triphenylphosphine (0.018 g, 0.00007 mol). The reaction mixture was purged with nitrogen for 10 min, PdCl$_2$(PPh$_3$)$_2$ (0.0099 g, 0.0000141 mol) was added followed by CuI (0.008 g, 0.000042 mol) and heated the reaction mixture in a sealed tube for 2 h at 100° C. After completion of the reaction, the reaction mixture was dissolved in water and extracted with EtOAc (2*50 mL). The combined organic layers were washed with brine solution, dried over Na$_2$SO$_4$, filtered and concentrated and the crude product was purified by column chromatography to get 7 (0.25g, 69.4%). LCMS=Calculated for C$_{30}$H$_{33}$N$_3$O$_5$, 515.61 Observed=516.2.

Step 7:Synthesis of 2-(3-methoxy-2-oxopyridin-1 (2H)-yl)-3-(4-((4-(morpholinomethyl) phenyl) ethynyl) phenyl)propanal (8)

To solution of 7 (0.3 g, 0.00048 mol) in THF (5mL) at -78° C. was added DiBAL-H (1M in THF, 0.16mL, 0.0011 mol) and stirred the reaction for 1 h at -78° C. After completion of the reaction, the reaction mixture was quenched with saturated NH$_4$Cl solution and extracted with EtOAc. The organic layer was washed with brine solution and dried over Na$_2$SO$_4$, filtered and concentrated under reduced pressure to get 8 (0.022 g, 80.7%). LCMS =Calculated for C$_{28}$H$_{28}$N$_2$O$_4$ 456.54, Observed=457.5.

Step 8:Synthesis of 1-(1-hydroxy-3-(4-((4-(morpholinomethyl) phenyl)ethynyl)phenyl)propan-2-yl)-3-methoxypyridin-2(1H)-one (9)

To a solution of 8 (0.22 g, 0.48 mmol) in methanol (1 mL) Sodium borohydride (36 mg, 0.96 mmol) was added and stirred at 25° C. for 10 min. After completion of the reaction, the reaction mixture was quenched with sat. NH$_4$Cl solution and extracted with EtOAc. The organic layer was washed with brine solution and dried over Na$_2$SO$_4$, filtered and concentrated under reduced pressure to get 9 (21 mg, 95.2%). UPLC=Calculated for C$_{28}$H$_{30}$N$_2$O$_4$ 458.56, Observed =459.5.

Step 9:Synthesis of 3-hydroxy-1-(1-hydroxy-3-(4-((4-(morpholinomethyl) phenyl) ethynyl)phenyl) propan-2-yl)pyridin-2(1H)-one, Compound 114

To a solution of 9 (0.1 g, 0.218 mmol) in pyridine (1 mL), Lithium iodide (0.173g, 1.5 mmol) was added and irradiated under microwave for 1h at 140° C. After completion of the reaction, pyridine was removed and the crude product was dissolved in water and extracted with EtOAc and the organic layer was washed with water and brine solution and dried over Na$_2$SO$_4$, filtered and concentrated under reduced pressure. The crude product was purified by column chromatography on silica gel (5-10% of methanol in DCM) to get Compound 114 (0.016 g, 16.6%). LCMS=Calculated for C$_{27}$H$_{28}$N$_2$O$_4$ 444.53, Observed =445.0.

Example 2

In vitro Assays to Screen Compounds and Metalloprotein Modulators Bacterial Susceptibility Testing Minimal inhibitory concentrations (MIC) were determined by the broth microdilution method in accordance with the Clinical and Laboratory Standards Institute (CLSI) guidelines. In brief, organism suspensions were adjusted to a 0.5 McFarland standard to yield a final inoculum between $3 \times 10^5$ and $7 \times 10^5$ colony-forming units (CFU)/mL. Drug dilutions and inocula were made in sterile, cation adjusted Mueller-Hinton Broth (Beckton Dickinson). An inoculum volume of 100 μL was added to wells containing 100 μL of broth with 2-fold serial dilutions of drug. All inoculated microdilution trays were incubated in ambient air at 35° C. for 18-24 h. Following incubation, the lowest concentration of the drug that prevented visible growth (OD600 nm <0.05) was recorded as the MIC. Performance of the assay was monitored by the use of laboratory quality-control strains and levofloxacin, a compound with a defined MIC spectrum, in accordance with CLSI guidelines.

TABLE 4

Exemplary in vitro assay data against select bacteria for compounds in embodiments of the disclosure.

| Compound ID No. | E. coli ATCC 25922 - no FBS | E. coli BW25113- no FBS | E. coli imp mutant | E. coli delta to IC mutant | S. aureus ATCC 29213 | P. aeruginosa 209 | P. aeruginosa 210 delta mexAB-OprM |
|---|---|---|---|---|---|---|---|
| 72 | A | A | A | A | D | D | D |
| 93 | D | D | D | D | D | D | D |
| 107 | D | N.D. | D | C | N.D. | N.D. | N.D. |
| 83 | D | D | B | C | D | D | D |
| 113 | D | N.D. | D | D | N.D. | N.D. | N.D. |
| 91 | D | D | D | C | C | D | D |
| 78 | D | B | A | A | D | D | D |
| 92 | D | N.D. | N.D. | N.D. | D | D | N.D. |
| 70 | D | D | B | C | C | D | D |
| 94 | D | D | D | D | D | D | D |
| 71 | D | D | D | D | D | D | D |
| 90 | D | D | B | C | D | D | D |
| 106 | D | N.D. | C | A | N.D. | N.D. | N.D. |
| 84 | D | D | D | D | D | D | D |
| 103 | D | D | D | B | D | D | D |
| 87 | B | B | B | A | D | D | D |
| 100 | B | B | A | A | D | D | D |
| 96 | D | D | D | D | D | D | D |
| 76 | C | B | B | A | D | D | D |
| 114 | C | N.D. | B | B | N.D. | N.D. | N.D. |
| 86 | A | A | A | A | D | D | D |
| 99 | D | B | A | A | D | D | D |
| 108 | D | N.D. | C | C | N.D. | N.D. | N.D. |
| 101 | D | D | D | B | D | D | D |
| 82 | D | D | B | C | D | D | D |
| 98 | B | A | B | A | D | D | D |
| 102 | C | C | C | C | D | D | C |
| 74 | C | B | B | A | D | D | D |
| 89 | D | D | C | D | C | D | D |
| 105 | C | N.D. | B | B | N.D. | N.D. | N.D. |
| 95 | D | D | C | D | D | D | D |
| 104 | C | N.D. | C | B | N.D. | N.D. | N.D. |
| 97 | B | A | A | A | D | D | D |
| 75 | C | B | B | A | D | D | D |
| 112 | C | N.D. | B | A | N.D. | N.D. | N.D. |
| 88 | A | A | A | A | D | D | D |
| 73 | C | B | B | B | D | D | D |

The MIC values in the table are as follows: A = less than 1 μg/mL; B = 1 to 8 μg/mL; C = greater than 8 to 32 μg/mL; D = greater than 32 μg/mL; and N.D. means no data.
FBS = fetal bovine serum.

Inhibition Assay against *Klebsiella pneumoniae* LpxC

LpxC inhibition assays were performed using liquid chromatography with tandem mass spectrometry. Assays were performed, in duplicate, in opaque, 96-well microplates in a total assay volume of 50 μL. The incubation mixture contained: LpxC (0.2 nM Kpn), 0.8 μM UDP-3-O-[(R)-3-hydroxymyristoyl]-N-acetyl-glucosamine, 40 mM Bis-Tris/HCl buffer (pH 5.9), 5 mM sodium phosphate buffer (NaH$_2$PO$_4$/Na$_2$HPO$_4$, pH 7.0), 1 mM DTT, 0.1% (w/v) fatty-acid free BSA, 10% DMSO (v/v, with or without compound). The reactions were incubated at 22° C. for 60 minutes (with mild shaking), then terminated by the addition of 25 μL 0.25 N HCl. Samples were analyzed using a LC-MS system to measure native LpxC substrate and reaction product. IC$_{50}$ analysis was done using GeneData Screener and a four parameter variable slope normalized to controls. Test compounds were prepared as 8-point dose-response curves (factor dilution 2) in triplicate, starting at 1 μM final concentration. Each assay plate included 6 wells used for the Z' factor calculation, 3 as a positive control for the assay and 3 as a negative control. The robustness was calculated as the median Z' factor for 5 plates. Chir-90, a well-known inhibitor of LpxC activity was used as inhibitor control standard.

The dose response curves for a known LpxC inhibitor Chir-90 and exemplary compounds of the disclosure are shown in FIGS. 9-11.

The RZ' factor obtained for this experiment (0.8324) indicates excellent assay quality in terms of signal dynamic range and data variation. The IC$_{50}$ value of 0.47 nM calculated for the Chir-90 inhibitor is consistent with previously reported values.

TABLE 5

Exemplary in vitro assay data against *Klebsiella pneumoniae* for compounds in embodiments of the disclosure.

| Compound ID No. | IC$_{50}$ (nM) |
|---|---|
| 97 | C |
| 98 | C |
| ChIR-090 | A |

For the enzyme potency, IC$_{50}$ values against *Klebsiella pneumoniae* in the table are as follows: A=less than 1 nM; B=1 to less than 10 nM; C=10 to 100 nM; D=greater than 100 nM; and N/D means no data.

Example 3

Treatment for Bacterial Infection

Human Clinical Trial of the Safety and/or Efficacy of Compounds for Treating Patients with cUTI, cIAI, HAP, or VAP Objective: To compare the safety of administered composition comprising compound 72, 88, 86, 97, or 98.

Study Design: This will be an observational, cohort study from medical chart review of adult hospitalized patients for each of the three conditions of interest (complicated urinary tract infection (cUTI), complicated intra-abdominal infection (cIAI) and nosocomial pneumonia (NP) including hospital acquired pneumonia (HAP) and ventilator-associated pneumonia (VAP)). For this study, the proposed patient selection period extends for 12 months. Patients selected during this period will be followed from diagnosis (i.e., diagnosis of cUTI, cIAI or NP) until symptom resolution, discharge or 30-days post discharge [based on data availability to assess readmission and outpatient visits], death while hospitalized, loss to follow-up or the end of study period if not yet discharged from index hospitalization.

Study Population: Adult (18 years or older) patients with diagnosis of at least one of the following conditions: urinary tract infection, intra abdominal infection, hospital acquired pneumonia, or ventilator associated pneumonia.

Phase I: Patients receive pharmaceutical compositions of compound 72, 88, 86, 97, or 98, each day of a 28-day cycle. Doses of compound 72, 88, 86, 97, or 98 may be held or modified for toxicity based on medical assessment. Treatment repeats every 28 days in the absence of unacceptable toxicity. Cohorts of 3-6 patients receive escalating doses of the compound until the maximum tolerated dose (MTD) for the compound is determined. The MTD is defined as the dose preceding that at which 2 of 3 or 2 of 6 patients experience dose-limiting toxicity.

Phase II: Patients receive compound 72, 88, 86, 97, or 98 as in phase I at the MTD determined in phase I. Treatment repeats every 4 weeks for 2-6 courses in the absence of infection progression or unacceptable toxicity. After completion of 2 courses of study therapy, patients who achieve a complete or partial response may receive an additional 4 courses. Patients who maintain stable infections for more than 2 months after completion of 6 courses of study therapy may receive an additional 6 courses at the time of infection progression, provided they meet original eligibility criteria.

Testing: Tests that will be used to monitor the effectiveness of the treated medical device include: physical exam, X-ray, urinalysis, blood work and other clinical laboratory methodologies used to detect pathogens in the patients.

Equivalents and Scope

It is, therefore, to be understood that the foregoing embodiments are presented by way of example only and that, within the scope of the appended claims and equivalents thereto, the present teachings may be practiced otherwise than as specifically described and claimed using no more than routine experimentation. The present teachings are directed to each individual feature and method described herein. In addition, any combination of two or more such features and methods, if such features and methods are not mutually inconsistent, is included within the scope of the present teachings. Such equivalents are intended to be encompassed by the scope of the following claims.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise. All cited sources, for example, references, publications, databases, database entries, and art cited herein, are incorporated into this application by reference, even if not expressly stated in the citation. In case of conflicting statements of a cited source and the instant application, the statement in the instant application shall control.

What is claimed is:

1. A compound of Formula IV:

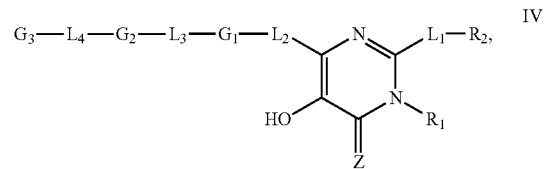

or a pharmaceutically acceptable salt thereof,
wherein:

$R_1$ is H or $C_{1-6}$ alkyl;

$R_2$ is H, —$OR^a$, —$N(R^a)_2$, $C_{1-6}$ alkyl, or $C_{1-6}$ alkoxy;

$L_1$ is a bivalent radical selected from a bond, —C(=O)—, —(C(=O)O)—, —OC(=O)—, —(C(=O)NR$^b$)—, —N(R$^b$)C(=O)—, —N(R$^b$)—, —S(=O)$_2$—, —(C$_{1-4}$ alkylene)-, —(C$_{1-4}$ alkylene)-O—, —(C$_{1-4}$ alkylene)-N(R$^b$)—, —(C$_{1-4}$ alkylene)-S—, and —(C$_{1-4}$ alkylene)-S(=O)$_2$—;

$L_2$ is a bivalent radical selected from —(C(R$_4$)(R$_5$))$_n$—(C$_{0-3}$ alkylene)-, —(C(R$_4$)(R$_5$))$_n$-C$_{0-3}$ alkylene)-(CH—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-C(=N—OH)—, —(C(R$_4$)(R$_5$))$_n$—(C$_{0-3}$ alkylene)-(C(=O)NR$_5$)—, —(C(R$_4$)(R$_5$))$_n$—(C$_{0-3}$ alkylene)-N(R$_5$)C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, —(C(R$_4$)(R$_5$))$_n$—(C$_{0-3}$ alkylene)-S(=O)$_2$—, —(C(R$_4$)(R$_5$))$_n$—(C$_{0-3}$ alkylene)-S(=O)$_2$N(R$_5$)—, and —(C(R$_4$)(R$_5$))$_n$—(C$_{0-3}$ alkylene)-N(R$_5$)S(=O)$_2$—;

each $R_4$ is H or $C_{1-6}$ alkyl; wherein the alkyl is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, $C_{1-6}$alkyl, $C_{2-6}$ alkenyl, $C_{2-6}$ alkynyl, $C_{3-10}$ cycloalkyl, $C_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$;

each R$_5$ is independently H, C$_{1-6}$ alkyl, C$_{1-6}$ heteroalkyl, C$_{2-6}$ alkenyl, C$_{2-6}$ alkynyl, C$_{6-14}$ aryl, 5- to 14-membered heteroaryl, C$_3$-C$_8$ cycloalkyl, —(C$_{0-4}$ alkylene)-OR$^f$, —(C$_{0-4}$ alkylene)-(C$_{2-4}$ alkene), —(C$_{0-4}$ alkylene)-(C$_{2-4}$ alkyne), C$_2$-C$_7$ heterocycle, —(C$_{0-4}$ alkylene)-C(=O)—(C$_1$-C$_6$ alkyl), —(C$_{0-4}$ alkylene)-C(=O)H, —(C$_{0-4}$ alkylene)-C(=O)OR$^f$, —(C$_{0-4}$ alkylene)-CN, —(C$_{0-4}$ alkylene)-halo, —(C$_{0-4}$ alkylene)-NO$_2$, —(C$_{0-4}$ alkylene)-N(R$^f$)$_2$, —(C$_{0-4}$ alkylene)-S(=O)$_2$—(R$^f$), —(C$_{0-4}$ alkylene)-(C$_{6-14}$ aryl), —(C$_{1-4}$ alkylene)-(5- to 14-membered heteroaryl), —(C$_{0-4}$ alkylene)- C(=O)NR$^b$R$^f$ or —(C$_{0-4}$ alkylene)-NR$^b$C(=O)R$^f$; wherein the alkyl, heteroalkyl, alkenyl, alkynyl, aryl, heteroaryl, or cycloalkyl is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$;

each R$^f$ is independently H, alkyl, heteroalkyl, alkenyl, alkynyl, cycloalkyl, heterocyclyl, aryl, heteroaryl, or alkoxy; wherein the alkyl, heteroalkyl, alkenyl, alkynyl, cycloalkyl, heterocyclyl, aryl, heteroaryl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$;

L$_3$ is a bivalent radical selected from —(C$_{2-6}$ alkenylene)- and —(C$_{2-6}$ alkynylene)-;

L$_4$ is a bivalent radical selected from —C(=O)—, —(C(=O)O)—, —(C(=O)NR$^e$)-, —N(R$^e$)C(=O)—, and —(C$_{1-4}$ alkylene)-;

G$_1$ and G$_2$ are each independently, at each occurrence, a bivalent radical selected from —(C$_{6-14}$ arylene)- and -(5- to 14-membered heteroarylene)-;

G$_3$ is H, C$_{3-7}$ cycloalkyl, C$_{3-10}$ heterocycloalkyl, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), alkyl, heteroalkyl, alkenyl, alkynyl, aryl, heteroaryl, or alkoxy; wherein the alkyl, heteroalkyl, alkenyl, alkynyl, cycloalkyl, heterocycloalkyl, aryl, heteroaryl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^{ad}$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$;

R$^a$, R$^b$, R$^c$, R$^d$, and R$^e$ are each independently, at each occurrence, H or C$_{1-6}$ alkyl; and n is 1 or 2.

2. The compound of claim 1, wherein:

L$_1$ is a bivalent radical selected from a bond, —(C(=O)O)—, —(C(=O)NR$^b$)—, —N(R$^b$)C(=O)—, —(C$_{1-4}$ alkylene)-O—, —(C$_{1-4}$ alkylene)-N(R$^b$)—, —(C$_{1-4}$ alkylene)-S—, and —(C$_{1-4}$ alkylene)-S(=O)$_2$—;

L$_2$ is a bivalent radical is selected from —(C(R$_4$)(R$_5$))$_n$— (C$_{0-3}$ alkylene), and —(C(R$_4$)(R$_5$))$_n$—(C$_{0-3}$ alkylene)-N(R$_5$)—;

each R$_5$ is independently H or C$_{1-6}$ alkyl, —C(=O)NR$^b$R$^f$ or —(C$_{1-4}$ alkylene)-NR$^b$C(=O)R$^f$;

each R$^f$ is independently H, C$_{1-6}$ alkyl, C$_{1-6}$ heteroalkyl, C$_{2-6}$ alkenyl, C$_{2-6}$ alkynyl, C$_{6-14}$ aryl, 5 to 14-membered heteroaryl, or C$_{3-8}$cycloalkyl; wherein the alkyl, heteroalkyl, alkenyl, alkynyl, cycloalkyl, aryl, or heteroaryl is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, $_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$; and G$_3$ is H, C$_{3-7}$ cycloalkyl, C$_{3-10}$ heterocycloalkyl, C$_{6-14}$ aryl, 5- to 14-membered heteroaryl, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), alkyl, heteroalkyl, alkenyl, alkynyl, or alkoxy; wherein the alkyl, heteroalkyl, alkenyl, alkynyl, cycloalkyl, heterocycloalkyl, aryl, heteroaryl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^c$(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$.

3. The compound of claim 1, wherein:
each R$_5$ is independently —(C$_{1-4}$ alkylene)-OR$^d$, —(C$_{1-4}$ alkylene)-N(R$^d$)$_2$, —(C$_{1-4}$ alklene)-S(=O)$_2$-(R$^f$), —(C$_{1-4}$ alkylene)-(C$_{6-14}$ aryl), —(C$_{1-4}$ alkylene)-(5- to 14-membered heteroaryl), —C(=O)NR$^b$R$^f$ or —(C$_{1-4}$ alkylene)-NR$^b$C(=O)R$^f$; and
each R$^f$ is independently H, alkyl, heteroalkyl, cycloalkyl, or heterocyclyl; wherein the alkyl, heteroalkyl, cycloalkyl, or heterocyclyl is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$.

4. The compound of claim 1, wherein:
L$_1$ is a bivalent radical selected from a bond, —(C$_{1-4}$ alkylene)-O—, —(C$_{1-4}$ alkylene)-N(R$^b$)—, —(C$_{1-4}$ alkylene)-S—, and —(C$_{1-4}$ alkylene)-S(=O)$_2$—.

5. The compound of claim 1, wherein the compound has the structure of Formula IVA:

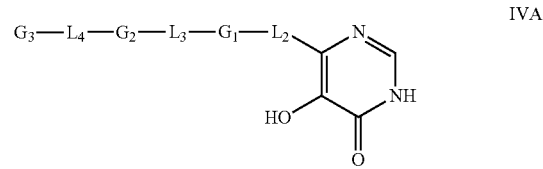

IVA or a pharmaceutically acceptable salt thereof.

6. The compound of claim 5, wherein:
L$_2$ is a bivalent radical selected from —(C(R$_4$)(R$_5$))$_n$—(C$_{0-3}$ alkylene)—, —(C(R$_4$)(R$_5$))$_n$—C$_{0-3}$ alkylene)-(CH—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, and —(C(R$_4$)(R$_5$))$_n$—(C$_{0-3}$ alkylene)-S(=O)$_2$—;
each R$^f$ is independently H, alkyl, cycloalkyl, heterocyclyl, or alkoxy; wherein the alkyl, cycloalkyl, heterocyclyl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$;

L$_3$ is —(C$_{2-6}$ alkynylene)-;
G$_1$ and G$_2$ are each independently, at each occurrence, —(C$_{6-14}$ arylene)-; and
G$_3$ is H, C$_{3-7}$ cycloalkyl, C$_{3-10}$ heterocycloalkyl, C$_{6-14}$ aryl, 5- to 14-membered heteroaryl, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), alkyl, heteroalkyl, alkenyl, alkynyl, or alkoxy; wherein the alkyl, heteroalkyl, alkenyl, alkynyl, cycloalkyl, heterocycloalkyl, aryl, heteroaryl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)

NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)R$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$.

7. The compound of claim 5, wherein:
L$_2$ is a bivalent radical selected from —(C(R$_4$)(R$_5$))$_n$—(C$_{0-3}$ alkylene)-, —(C(R$_4$)(R$_5$))$_n$—(C$_{0-3}$ alkylene)-N(R$_5$)—, and —(C(R$_4$)(R$_5$))$_n$—(C$_{0-3}$ alkylene)-S(=O)$_2$—;
each R$^f$ is independently H, alkyl, cycloalkyl, heterocyclyl, or alkoxy; wherein the alkyl, cycloalkyl, heterocyclyl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$ —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$;
L$_3$ is —(C$_{2-6}$ alkynylene)-;
L$_4$ is —C(=O)—, —(C(=O)O)—, —(C(=O)NR$^e$)—, or —(C$_{1-4}$ alkylene)-;
G$_1$ and G$_2$ are each independently, at each occurrence, —(C$_{6-14}$ arylene)-; and
G$_3$ is H, C$_{3-7}$ cycloalkyl, C$_{3-10}$ heterocycloalkyl, C$_{6-14}$ aryl, 5- to 14-membered heteroaryl, (C$_{1-4}$ alkylene)-(C$_{1-4}$ heteroalkyl), (C$_{1-4}$ alkylene)-(C$_{1-4}$ heterocycloalkyl), (C$_{3-10}$ heterocycloalkylene)-(C$_{1-4}$ alkyl), (C$_{3-10}$ heterocycloalkylene)-(C$_{1-4}$ heteroalkyl), (C$_{3-10}$ heterocycloalkylene)-(C$_{3-10}$ heterocycloalkyl), C$_{1-6}$ alkyl, or (C$_{3-10}$ heterocycloalkylene)-hydroxy.

8. The compound of claim 5, wherein G$_3$ is H, C$_{3-10}$ heterocycloalkyl, (C$_{1-4}$ alkylene)-(C$_{1-4}$ heteroalkyl), (C$_{1-4}$ alkylene)-(C$_{1-4}$ heterocycloalkyl), (C$_{3-10}$ heterocycloalkylene)-(C$_{1-4}$ heteroalkyl), (C$_{3-10}$ heterocycloalkylene)-(C$_{3-10}$ heterocycloalkyl), C$_{1-6}$ alkyl, (C$_{3-10}$ heterocycloalkylene)-hydroxy, or tetrazolyl.

9. The compound of claim 1, wherein the compound has the structure of Formula IVB:

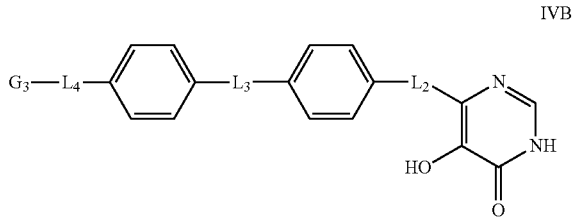

IVB or a pharmaceutically acceptable salt thereof.

10. The compound of claim 9, wherein:
L$_2$ is a bivalent radical selected from —(C(R$_4$)(R$_5$))$_n$—(C$_{0-3}$ alkylene)-, —(C(R$_4$)(R$_5$))$_0$—C$_{0-3}$ alkylene)-(CH—OR$^c$)—, —(C(R$_4$)(R$_5$))$_n$—(C$_{0-3}$ alkylene)-C(=O)—, —(C(R$_4$)(R$_5$))$_n$—(C$_{0-3}$ alkylene)-O—, —(C(R$_4$)(R$_5$))$_n$—(C$_{0-3}$ alkylene)-N(R$_5$)—, and —(C(R$_4$)(R$_5$))$_n$—(C$_{0-3}$ alkylene)-S(=O)$_2$—;
each R$^f$ is independently H, alkyl, cycloalkyl, heterocyclyl, or alkoxy; wherein the alkyl, cycloalkyl, heterocyclyl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-4}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$;
L$_3$ is —(C$_{2-6}$ alkynylene)-; and
G$_3$ is H, C$_{3-7}$ cycloalkyl, C$_{3-10}$ heterocycloalkyl, C$_{6-14}$ aryl, 5- to 14-membered heteroaryl, (C$_{1-4}$ alkylene)-(C$_{1-4}$ heteroalkyl), (C$_{3-10}$ heterocycloalkylene)-(C$_{1-4}$ alkyl), (C$_{3-10}$ heterocycloalkylene)-(C$_{1-4}$ heteroalkyl), alkyl, heteroalkyl, alkenyl, alkynyl, or alkoxy; wherein the alkyl, heteroalkyl, alkenyl, alkynyl, cycloalkyl, heterocycloalkyl, aryl, heteroaryl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, —S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$.

11. The compound of claim 9, wherein:

L$_2$ is a bivalent radical selected from —(C(R$_4$)(R$_5$))$_n$—(C$_{0-3}$ alkylene)-, —(C(R$_4$)(R$_5$))$_n$—(C$_{0-3}$ alkylene)-N(R$_5$)—, and —(C(R$_4$)(R$_5$))$_n$—(C$_{0-3}$ alkylene)-S(=O)$_2$—;

each R$^f$ is independently H, alkyl, cycloalkyl, heterocyclyl, or alkoxy; wherein the alkyl, cycloalkyl, heterocyclyl, or alkoxy is unsubstituted or substituted with one or more substituents selected from halogen, —CN, —NO$_2$, —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, S(O)$_2$R$^a$, —S(O)NR$^b$R$^c$, S(O)$_2$NR$^b$R$^c$, C$_{1-6}$ alkyl, C$_{2-6}$ alkenyl, C$_{2-6}$ alkynyl, C$_{3-10}$ cycloalkyl, C$_{6-14}$ aryl, heteroaryl, or heterocyclyl; and wherein the alkyl, alkenyl, alkynyl, cycloalkyl, aryl, heteroaryl, or heterocyclyl substituent is unsubstituted or further substituted with one or more substituents selected from halogen, —CN, —NO$_2$, —C(O)R$^a$, —C(O)OR$^a$, —C(O)NR$^b$R$^c$, —OR$^a$, —OC(O)R$^a$, —OC(O)OR$^a$, —OC(O)NR$^b$R$^c$, —OS(O)$_2$R$^a$, —OS(O)$_2$NR$^b$R$^c$, —NR$^b$R$^c$, —NR$^a$C(O)R$^d$, —NR$^a$C(O)OR$^a$, —NR$^a$C(O)NR$^b$R$^c$, —NR$^a$S(O)$_2$R$^d$, —NR$^a$S(O)$_2$NR$^b$R$^c$, —SR$^a$, —S(O)R$^a$, —S(O)$_2$R$^a$ and —S(O)$_2$NR$^b$R$^c$;

L$_3$ is —(C$_{2-6}$ alkynylene)-;

L$_4$ is —C(=O)—, —(C(=O)O)—, —(C(=O)NR$^e$)—, or —(C$_{1-4}$ alkylene)-; and

G$_3$ is H, C$_{3-7}$ cycloalkyl, C$_{3-10}$ heterocycloalkyl, C$_{6-14}$ aryl, 5- to 14-membered heteroaryl, (C$_{1-4}$ alkylene)-(C$_{1-4}$ heteroalkyl), (C$_{1-4}$ alkylene)-(C$_{1-4}$ heterocycloalkyl), (C$_{3-10}$ heterocycloalkylene)-(C$_{1-4}$ alkyl), (C$_{3-10}$ heterocycloalkylene)-(C$_{1-4}$ heteroalkyl), (C$_{3-10}$ heterocycloalkylene)-(C$_{3-10}$ heterocycloalkyl), C$_{1-6}$ alkyl, or (C$_{3-10}$ heterocycloalkylene)-hydroxyl.

12. The compound of claim 9, wherein G$_3$ is H, C$_{3-10}$ heterocycloalkyl, (C$_{1-4}$ alkylene)-(C$_{1-4}$ heteroalkyl), (C$_{1-4}$ alkylene)-(C$_{1-4}$ heterocycloalkyl), (C$_{3-10}$ heterocycloalkylene)-(C$_{1-4}$ heteroalkyl), (C$_{3-10}$ heterocycloalkylene)-(C$_{3-10}$ heterocycloalkyl), C$_{1-6}$ alkyl, (C$_{3-10}$ heterocycloalkylene)-hydroxy, or tetrazolyl.

13. The compound of claim 9, wherein L$_3$ is —(C$_2$-alkynylene)-.

14. The compound of claim 9, wherein L$_2$ is a bivalent radical selected from —(C(R$_4$)(R$_5$))$_n$—(C$_{0-3}$ alkylene)- and —(C(R$_4$)(R$_5$))$_n$—(C$_{0-3}$ alkylene)-N(R$_5$).

15. The compound of claim 9, wherein:

L$_2$ is a bivalent radical selected from —(C(R$_4$)$_{(R5)}$)$_n$—(C$_{0-3}$ alkylene)- and —(C(R$_4$)(R$_5$))$_n$—(C$_{0-3}$ alkylene)-N(R$_5$)—; and n is 2.

16. The compound of claim 1, wherein the compound is selected from the group consisting of:

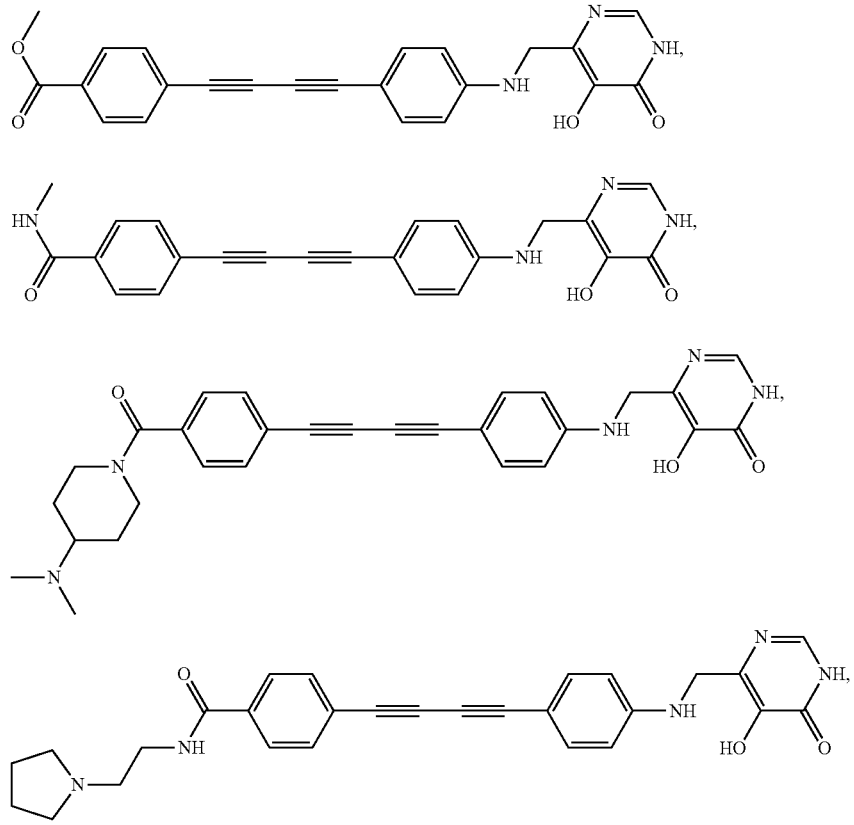

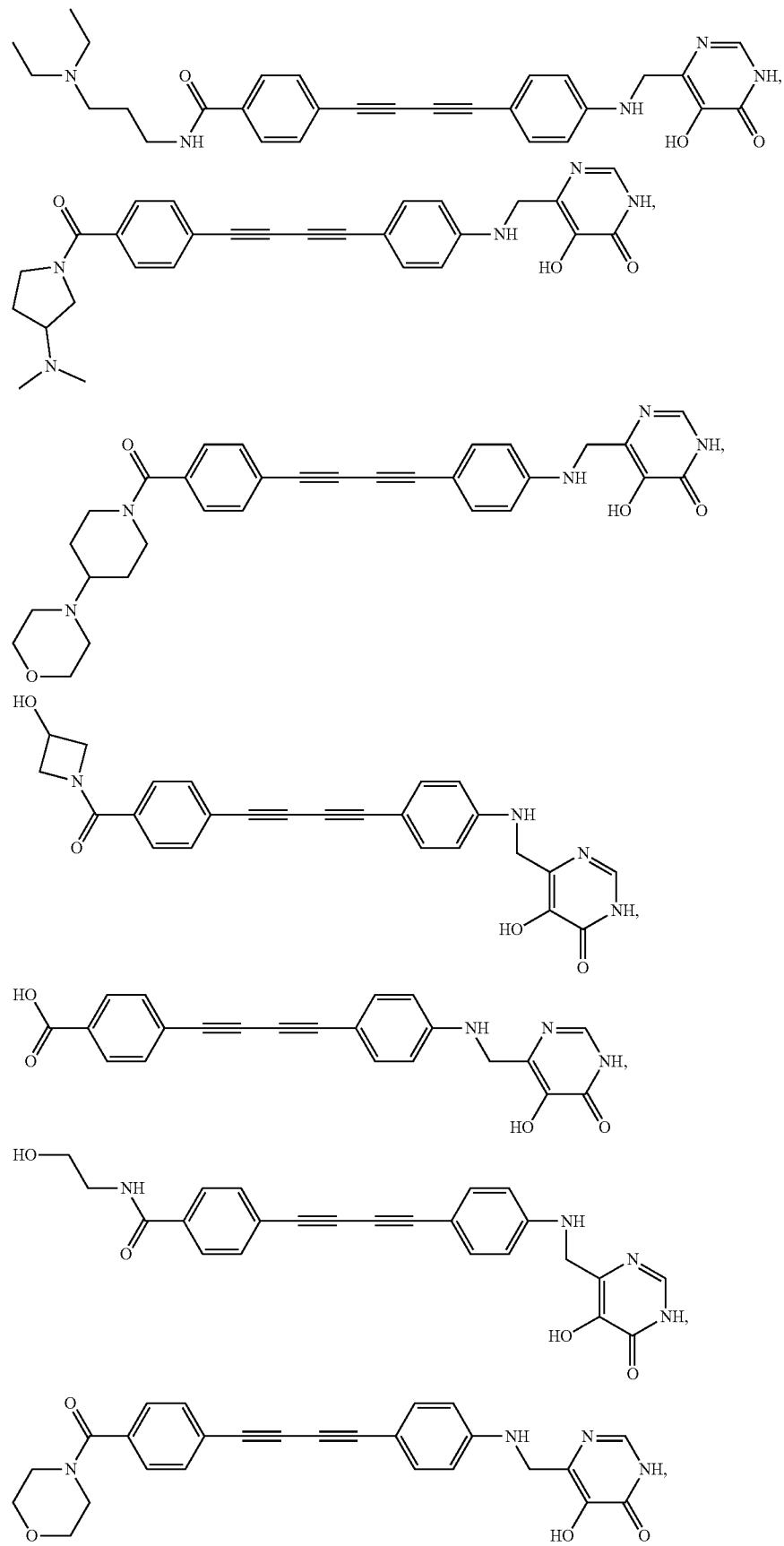

-continued
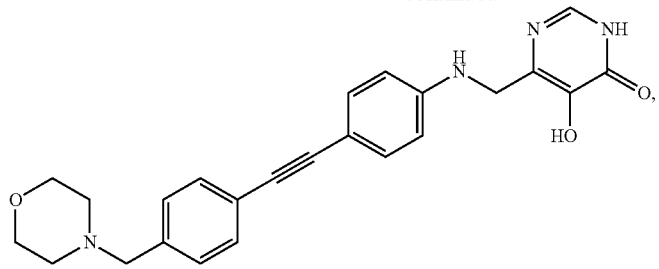
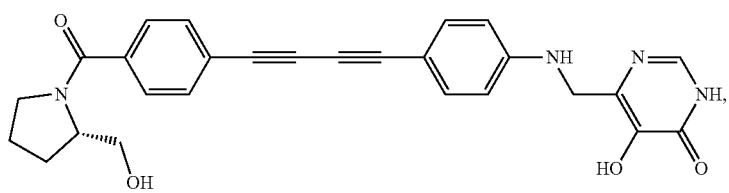
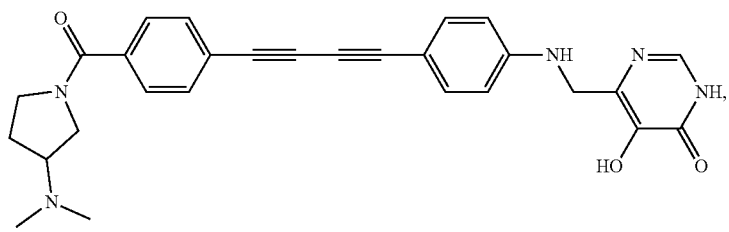
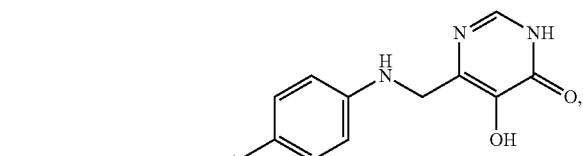
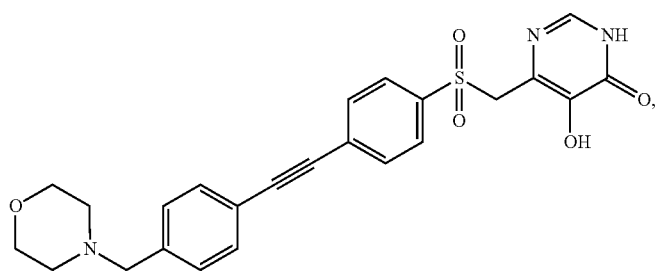
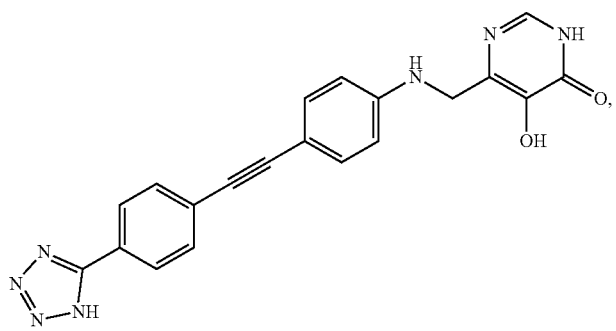

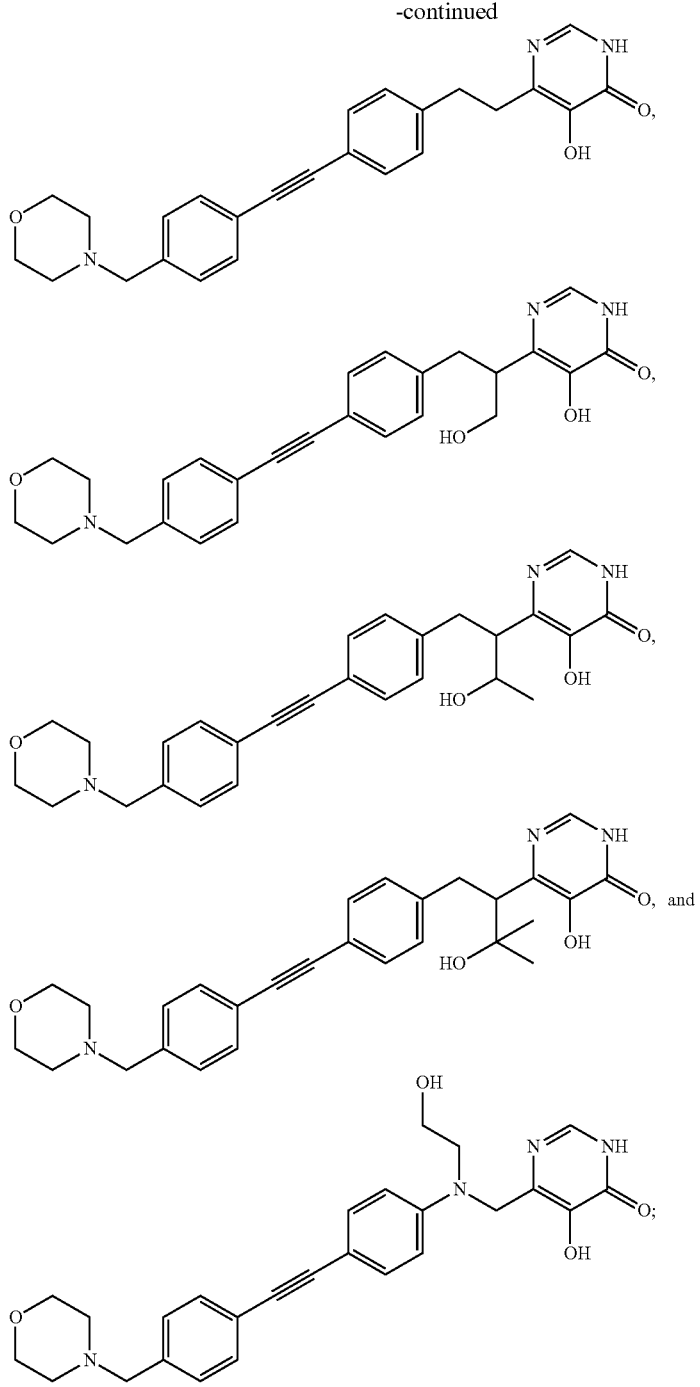

or a pharmaceutically acceptable salt thereof.

17. A pharmaceutical composition comprising a therapeutically effective amount of a compound of claim 1, or a pharmaceutically acceptable salt thereof, and a pharmaceutically acceptable excipient.

18. A method for modulating the activity of UDP-{3-O-[(R)-3-hydroxymyristoyl]}-N-acetylglucosamine deacetylase in a subject, comprising administering to a subject in need thereof a therapeutically effective amount of a compound of claim 1, or a pharmaceutically acceptable salt thereof.

19. A method for treating a gram-negative bacterial infection in a subject, comprising administering to a subject in need thereof a therapeutically effective amount of a pharmaceutical composition of claim 17.

* * * * *